United States Patent
Kale et al.

(10) Patent No.: US 6,420,507 B1
(45) Date of Patent: *Jul. 16, 2002

(54) OLEFIN POLYMERS PREPARED WITH SUBSTITUTED INDENYL CONTAINING METAL COMPLEXES

(75) Inventors: Lawrence T. Kale, Cochrane, CA (US); Daniel D. Vanderlende, Sugar Land, TX (US); Peter N. Nickias; Jasson T. Patton, both of Midland, MI (US); James C. Stevens, Richmond, TX (US); Deepak R. Parikh; Debra J. Mangold, both of Lake Jackson, TX (US)

(73) Assignee: The Dow Chemical Company, Midland, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 35 days.

(21) Appl. No.: 09/070,957

(22) Filed: May 1, 1998

Related U.S. Application Data

(63) Continuation-in-part of application No. 08/949,505, filed on Oct. 14, 1997, now Pat. No. 5,965,756.
(60) Provisional application No. 60/045,410, filed on May 1, 1997, and provisional application No. 60/045,348, filed on May 1, 1997.

(51) Int. Cl.[7] ................. C08F 10/00; C08F 210/00; C08F 4/49
(52) U.S. Cl. ................. 526/348; 526/133; 526/160; 526/161; 526/126; 502/152
(58) Field of Search ................. 526/160, 161, 526/943, 348, 348.6, 133; 502/152

(56) References Cited

U.S. PATENT DOCUMENTS 5,055,438 A    10/1991    Canich et al.

(List continued on next page.)

FOREIGN PATENT DOCUMENTS

EP    286177 A    10/1988

(List continued on next page.)

*Primary Examiner*—David W. Wu
*Assistant Examiner*—R. Harlan

(57) ABSTRACT

The subject invention is directed to an olefin polymer produced by polymerizing at least one α-olefin in the presence of a Group 4 metal complex comprising an indenyl group substituted in the 2 or 3 position with at least one group selected from hydrocarbyl, perfluoro-substituted hydrocarbyl, silyl, germyl and mixtures thereof, said indenyl group further being covalently bonded to the metal by means of a divalent ligand group, wherein the divalent ligand comprises nitrogen or phosphorus having an aliphatic or alicyclic hydrocarby group covalently bonded thereto via a primary or secondary carbon. Preferred olefin polymers of the invention will be characterized as having a high molecular weight, narrow molecular weight distribution, high vinyl content, and a bimodal DSC melting curve or a deconvoluted ATREF or GPC curve which shows at least two distinct narrow peaks. The olefin polymer will have utility in a variety of applications, including but not limited to films, fibers, foams, molded parts, and as components of formulations such as adhesives, sealants, coatings, caulks, and asphalt.

33 Claims, 13 Drawing Sheets

U.S. PATENT DOCUMENTS

| | | |
|---|---|---|
| 5,057,475 A | 10/1991 | Canich et al. |
| 5,064,802 A | 11/1991 | Stevens et al. |
| 5,096,867 A | 3/1992 | Canich |
| 5,132,380 A | 7/1992 | Stevens et al. |
| 5,272,236 A | 12/1993 | Lai et al. |
| 5,278,272 A | 1/1994 | Lai et al. |
| 5,380,810 A | 1/1995 | Lai et al. |
| 5,447,895 A * | 9/1995 | Marks et al. ................ 502/117 |
| 5,470,993 A | 11/1995 | Devore et al. |
| 5,621,126 A | 4/1997 | Canich et al. |
| 5,631,391 A | 5/1997 | Canich |
| 5,962,714 A * | 10/1999 | McCullough et al. ......... 556/11 |
| 5,965,756 A * | 10/1999 | McAdon et al. ............... 556/11 |

FOREIGN PATENT DOCUMENTS

| | | |
|---|---|---|
| EP | 298700 A | 1/1989 |
| EP | 416815 B | 3/1991 |
| EP | 468651 A | 1/1992 |
| EP | 514828 A | 11/1992 |
| EP | 520732 | 12/1992 |
| EP | 619827 | 7/1993 |
| EP | 659773 | 6/1995 |
| EP | 676421 | 10/1995 |
| EP | 749975 A | 12/1996 |
| WO | 93/19104 | 9/1993 |
| WO | 94/07930 | 4/1994 |
| WO | 94/17112 | 8/1994 |
| WO | 95/00526 | 1/1995 |
| WO | 95/14024 | 5/1995 |
| WO | 97/15583 | 5/1997 |
| WO | 98/49212 | 11/1998 |

* cited by examiner

- Example 1(a)
- Example 2(a)
- Comparative Example C-3a

- Example 1(a)
- Example 2(a)
- Comparative Example C-3a

Fits to GPC 220231 (lines)
$M_{n1} = 78776$
$M_{w1}/M_{n1} = 2.2377$
Split = 60.0%($M_{n1}$)
$M_{n2} = 32152$
$M_{w2}/M_{n2} = 2.0000$ Measured (symbols)
GPC $M_w$ = 132500
GPC $M_n$ = 52900
GPC $M_w/M_n$ = 2.505

Fits to GPC 22026 (lines)
$M_{n1} = 65455$
$M_{w1}/M_{n1} = 2.3827$
Split = 81.51%($M_{n1}$)
$M_{n2} = 31459$
$M_{w2}/M_{n2} = 2.0002$ Measured (symbols)
GPC $M_w$ = 136300
GPC $M_n$ = 54100
GPC $M_w/M_n$ = 2.5194

Fits to GPC 220191 (lines)
$M_{n1}$ = 68670
$M_{w1}/M_{n1}$ = 2.3172
Split = 95.54%($M_{n1}$)
$M_{n2}$ = 47558
$M_{w2}/M_{n2}$ = 2.0004

Measured (symbols)
GPC $M_w$ = 159700
GPC $M_n$ = 77000
GPC $M_w/M_n$ = 2.074

—— Viscosity 2a Continuous
········ Viscosity c-2a Batch
—·—·— Tan δ 2a Continuous
— — — Tan δ c-2a Batch

OLEFIN POLYMERS PREPARED WITH SUBSTITUTED INDENYL CONTAINING METAL COMPLEXES

CROSS REFERENCE TO RELATED APPLICATIONS

This application claims priority from provisional applications No. 60/045,410 filed May 1, 1997 and U.S. Ser. No. 60/045,348 filed May 1, 1997. This application is also a continuation-in-part application of U.S. Ser. No. 08/949,505, filed Oct. 14, 1997, now U.S. Pat. No. 5,965,756, which claims priority from U.S. Ser. No. 60/034,817 filed Dec. 19, 1996.

FIELD OF THE INVENTION

This invention relates to a class of Group 4 metal complexes and to olefin polymerization catalysts derived therefrom that are particularly suitable for use in a polymerization process for preparing polymers by polymerization of α-olefins and mixtures of α-olefins, and to the α-olefins and mixtures of α-olefins resulting therefrom.

BACKGROUND OF THE INVENTION

Constrained geometry metal complexes and methods for their preparation are disclosed in EP-A416,815; EP-A-468,651; EP-A-514,828; EP-A-520,732 and WO93/19104, as well as U.S. Pat. No. 5,055,438, U.S. Pat. No. 5,057,475, U.S. Pat. No. 5,096,867, U.S. Pat. No. 5,064,802, U.S. Pat. No. 5,132,380, U.S. Pat. No. 5,470,993, WO95/00526, and US Provisional Application 60-005913. Variously substituted indenyl containing metal complexes have been taught in U.S. Ser. No. 592,756, filed Jan. 26, 1996, as well as WO 95/14024. The teachings of all of the foregoing patents or the corresponding U.S. patent applications are incorporated herein by reference in their entirety.

Constrained geometry catalysts and other single site or metallocene catalysts are useful to prepare homogeneous olefin polymers. The term "homogeneous olefin polymers" refers to homopolymers or interpolymers of one or more α-olefins which are characterized as having a narrow polydispersity, i.e., an $M_w/M_n$ of from 1.5 to 3.0, and, in the case of interpolymers, a homogeneous short chain branching distribution, i.e., wherein each molecule has substantially the same number of short chain branches. Homogeneous olefin polymers are advantageous over Ziegler Natta produced polymers, in that they lack a low molecular weight tail fraction, which translates to improved strength and toughness. Homogeneous olefin polymers are further advantageous over Ziegler Natta produced polymers, in that the catalysts useful to prepare such polymers, particularly the constrained geometry catalysts, readily and efficiently incorporate comonomer, which permits the cost-effective production of polymers having a density of less than 0.910 g/cm³ which accords good elastomeric properties.

Despite their advantageous features, homogeneous polymers are typically more difficult to process than their Ziegler Natta counterparts, in part due to the absence of the low molecular weight fraction and in part due to the narrowness of the melting region.

One preferred class of homogeneous olefin polymers is the class of substantially linear polymers, which are characterized as having a narrow polydispersity, a homogeneous short chain branching distribution, and the presence of sufficient long chain branching to provide improved rheological properties and resistance to melt fracture. Substantially linear polymers are disclosed and claimed in U.S. Pat. Nos. 5,272,236; 5,278,272; 5,380,810; and EP 659,773; EP 676,421; and WO 94/07930.

An alternate approach to utilizing the preferred substantially linear olefin polymers has been to incorporate into homogeneous olefin polymers effective amounts of polymer processing aids prior to fabrication into films or articles. This is disadvantageous, in that it requires an additional processing step and adds cost to the finished product.

While homogeneous olefin-based elastomers, and particularly substantially linear olefin polymers, have found significant commercial utility, the low density of the elastomers, coupled with the absence of a higher crystallinity non-short chain branched fraction renders such polymers relatively poor in terms of upper service temperature and susceptible to deformation under heat, such as in a clothes dryer.

To improve the upper service temperature of homogeneous olefin polymers which are elastomers, one can blend such polymers with higher crystallinity homogeneous or heterogeneous olefin polymers, either via a physical blend or via an in-reactor mixture produced in a dual reactor system, such as is disclosed in U.S. Ser. No. 510,527, filed on Aug. 2, 1995 (WO 94/171112) and U.S. Ser. No. 208,068, filed on Mar. 8,1994 (EP 619827), each of which is incorporated herein by reference in its entirety.

However, industry would find great advantage in a polymer having elastomeric properties which exhibits a resistance to deformation under heat which is greater than that of a physical or in-reactor blend of the same overally density. Industry would find particular advantage in those of such polymers which have an overall polydispersity of from 1.5 to 3.0, but which have excellent processability, as evidenced by resistance to melt fracture and/or an $I_{10}/I_2$ of at least 10. Industry would find especially particular advantage in those of such polymers which may be produced in a single reactor using a highly efficient catalyst which is resistant to degradation at elevated temperature.

It is noted that U.S. Pat. No. 5,621,126 to Exxon Chemical Patents, Inc., discloses the use of mono(cyclopentadienyl) Group IV B metal compounds to produce ethylene/α-olefin copolymers. U.S. Pat. No. 5,621,126 asserts that catalysts containing an amido group having a hydrocarbyl ligand R' which is aliphatic or alicyclic and which is bonded to the nitrogen atom through a primary or secondary carbon produce copolymers having a greater degree of α-olefin incorporation than catalysts wherein the hydrocarbyl ligand R' is bonded to the nitrogen atom through a tertiary carbon atom or wherein R' bears aromatic carbon atoms. U.S. Pat. No. 5,621,126 asserts that when the R' ligand is bonded to the nitrogen atom through a secondary carbon atom, the activity of the catalyst is greater when R' is alicyclic than when R' is bonded to the nitrogen through a primary carbon atom of an aliphatic group of identical carbon number. U.S. Pat. No. 5,621,126 asserts that as the number of carbon atoms of R' thereof increases, the productivity of the catalyst system and the molecular weight of the ethylene/α-olefin copolymer increase while the amount of α-olefin comonomer incorporated remains about the same or increases. U.S. Pat. No. 5,621,126 asserts that the more preferred R' ligand is cyclododecyl.

The compositions of U.S. Pat. No. 5,621,126 are disadvantageous, in that they are believed to lack long chain branching, making them susceptible to melt fracture, and thus, less commercially desirable.

Further, while mono(cyclopentadienyl) Group IV B metal compounds may indeed find great commercial advantage in the polymerization of ethylene/α-olefin interpolymers, those in industry are continually seeking improvements and, in particular, would find advantage in catalysts which withstand higher reaction temperatures than are characteristic of bmono(cyclopentadienyl) catalysts. Such higher reaction temperatures would translate to polymers exhibiting a high degree of vinyl unsaturation, making them especially useful as precursors to functionalized polymers, and enhancing long chain branch incorporation when appropriate polymerization conditions are employed.

SUMMARY OF THE INVENTION

According to the present invention there is provided a product produced by a process for preparing polymers of olefin monomers comprising contacting one or more such monomers with a catalyst comprising:

1) a metal complex corresponding to the formula:

wherein:
M is titanium, zirconium or hafnium in the +2, +3 or +4 formal oxidation state;
A' is a substituted indenyl group substituted in at least the 2 or 3 position with a group selected from hydrocarbyl, fluoro-substituted hydrocarbyl, hydrocarbyloxy-substituted hydrocarbyl, dialkylamino-substituted hydrocarbyl, silyl, germyl and mixtures thereof, said group containing up to 40 nonhydrogen atoms, and said A' further being covalently bonded to M by means of a divalent Z group;
Z is a divalent moiety bound to both A' and M via σ-bonds, said Z comprising boron, or a member of Group 14 of the Periodic Table of the Elements, and also comprising nitrogen, phosphorus, sulfur or oxygen, wherein Z preferably has covalently bonded thereto an aliphatic or cycloaliphatic hydrocarbyl or substituted hydrocarbyl group, such that the hydrocarbyl group is covalently bonded to Z via a primary or secondary carbon;
X is an anionic or dianionic ligand group having up to 60 atoms exclusive of the class of ligands that are cyclic, delocalized, π-bound ligand groups;
X' independently each occurrence is a neutral ligating compound, having up to 20 atoms;
p is 0, 1 or 2, and is two less than the formal oxidation state of M, with the proviso that when X is a dianionic ligand group, p is 1; and
q is 0, 1 or 2; and
2) an activating cocatalyst
the molar ratio of 1) to 2) being from 1:10,000 to 100:1, or
the reaction product formed by converting 1) to an active catalyst by use of an activating technique.

Also disclosed is a product produced by a process comprising reacting one or more α-olefins in the presence of a catalyst which in turn comprises a metal complex corresponding to the formula:

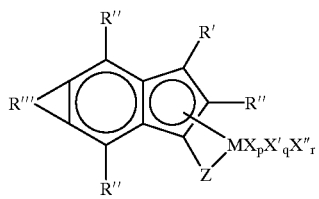

where M is titanium, zirconium or hafnium in the +2, +3 or +4 formal oxidation state;
R' and R" are independently each occurrence hydride, hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylene-phosphino-substituted hydrocarbyl, or hydrocarbylsulfido-substituted hydrocarbyl, said R' or R" group having up to 40 nonhydrogen atoms, and optionally two or more of the foregoing groups may together form a divalent derivative;
R'" is a divalent hydrocarbylene- or substituted hydrocarbylene group forming a fused system with the remainder of the metal complex, said R'" containing from 1 to 30 nonhydrogen atoms;
Z is a divalent moiety, or a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;
X is a monovalent anionic ligand group having up to 60 atoms exclusive of the class of ligands that are cyclic, delocalized, π-bound ligand groups;
X' independently each occurrence is a neutral ligating compound having up to 20 atoms;
X" is a divalent anionic ligand group having up to 60 atoms;
p is zero, 1, 2, or 3;
q is zero, 1 or 2, and
r is zero or 1; and
2) an activating cocatalyst
the molar ratio of 1) to 2) being from 1:10,000 to 100:1, or
the reaction product formed by converting 1) to an active catalyst by use of an activating technique.

The present catalysts and process employed in the polymerization of the polymers of the invention, preferably by means of a solution polymerization process, result in the highly efficient production of high molecular weight olefin polymers, particularly ethylene/α-olefin interpolymers, ethylene/propylene/diene interpolymers (EPDM), wherein the diene is ethylidenenorbornene, 1,4-hexadiene, or a similar nonconjugated diene, or is piperylene, over a wide range of polymerization conditions, and especially at elevated temperatures. The use of elevated temperatures dramatically increases the productivity of such process due to the fact that increased polymer solubility at elevated temperatures allows the use of increased conversions (higher concentration of polymer product) without exceeding solution viscosity limitations of the polymerization equipment as well as reduced energy costs needed to devolatilize the reaction product.

The subject invention further provides an olefin interpolymer, preferably an interpolymer of ethylene and at least one $C_3$–$C_{20}$ α-olefin, characterized as satisfying at least four of the following criteria, especially all five of the following criteria:

a) an $I_2 \leq 100$ g/10 min, b) an $M_w/M_n$ of from 1.5 to 3.0, c) at least 0.03 vinyls/1000 carbons, as determined by FTIR, and d) at least two distinct ATREF peaks, each of which satisfies the following inequality:

ATREF Shape Factor $\leq 0.90 - 0.00626$ (Average Elution Temperature).

The use of the indenyl and indecenyl catalysts as disclosed herein leads to the production of polymers having a high degree of vinyl termination. The resultant high level of vinyls/1000 carbons makes the polymers of the invention especially useful in applications wherein the polymers are subsequently functionalized. The resultant high level of vinyls/1000 carbons further makes the polymers able to achieve higher levels of long chain branching when appropriate polymerization conditions are employed.

Preferably, the polymers of the invention will be characterized as having an $I_{10}/I_2$ of at least 10, preferably at least 12, and most preferably at least 15.

As further qualitative indicia of long chain branching, the polymers of the invention will preferably further be characterized as exhibiting a critical shear rate at the onset of surface melt fracture which is at least 50 percent greater than the critical shear rate at the onset of surface melt fracture for a linear interpolymer, wherein the substantially linear interpolymer and the linear interpolymer comprise the same comonomer or comonomers, the linear interpolymer has an $I_2$, $M_w/M_n$ and density within ten percent of that of the substantially linear interpolymer, and wherein the respective critical shear rates of the substantially linear interpolymer and the linear interpolymer are measured at the same melt temperature using a gas extrusion rheometer.

The olefin interpolymers of the invention are uniquely characterized as being bimodal with respect to the short chain branching distribution and molecular weight, as evidenced by the differential scanning calorimetry and ATREF curves, as well as the deconvoluted gel permeation chromatographs. This effect is particularly true for interpolymers having a density of no more than 0.910 g/cm³.

It has been found that interpolymers of the invention having a density less than 0.890 g/cm³, particularly having a density of no more than 0.880 g/cm³, and more particularly having a density of less than 0.870 g/cm³ have a particularly superior and highly unique balance of properties. In particular, such polymers have improved elastomeric properties, such as a compression set of less than 90 percent, preferably less than 85 percent, more preferably less than 80 percent, coupled with an upper service temperature which exceeds that of a physical blend of interpolymers corresponding to the components of the interpolymers of the invention as discerned by the deconvolution of the representative gel permeation chromatograph. The uniqueness of the interpolymers of the invention is evident in micrographs obtained by transmission electron microscropy, which clearly show the presence of lamella in interpolymers whose density would suggest should be wholly amorphous.

The olefin interpolymers of the invention are expected to have great utility in a variety of applications, including but not limited to films, fibers, foams, injection molded parts, rotational molded parts, and as components of formulations such as adhesives, sealants, coatings, caulks, asphalt, etc.

These and other embodiments are more fully described in the following Detailed Description, wherein.

Figure 8A:
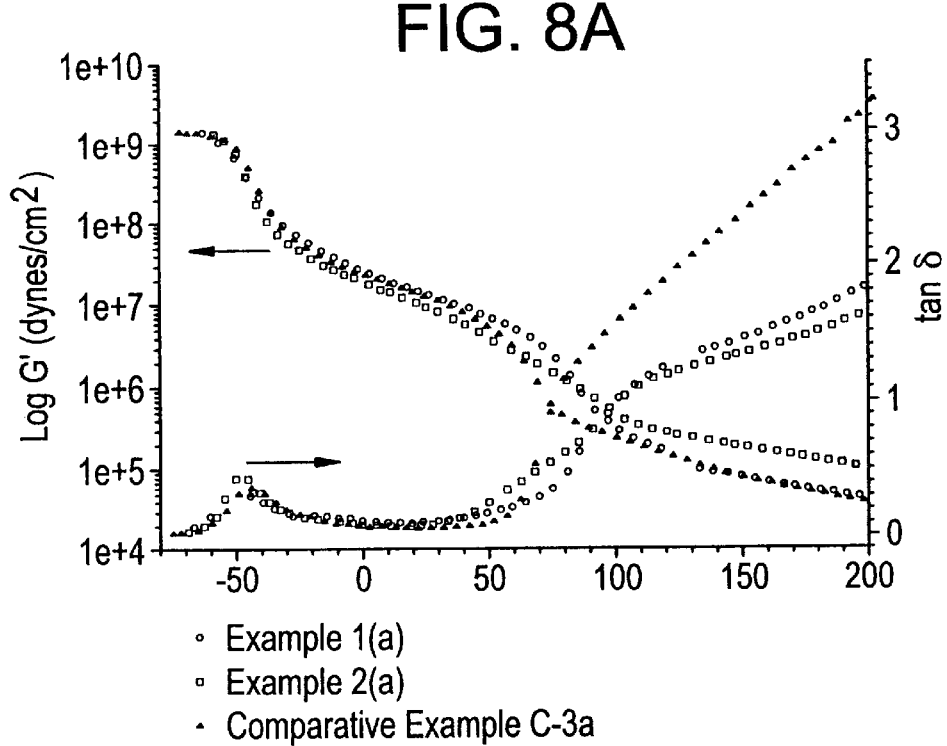
Figure 8B:
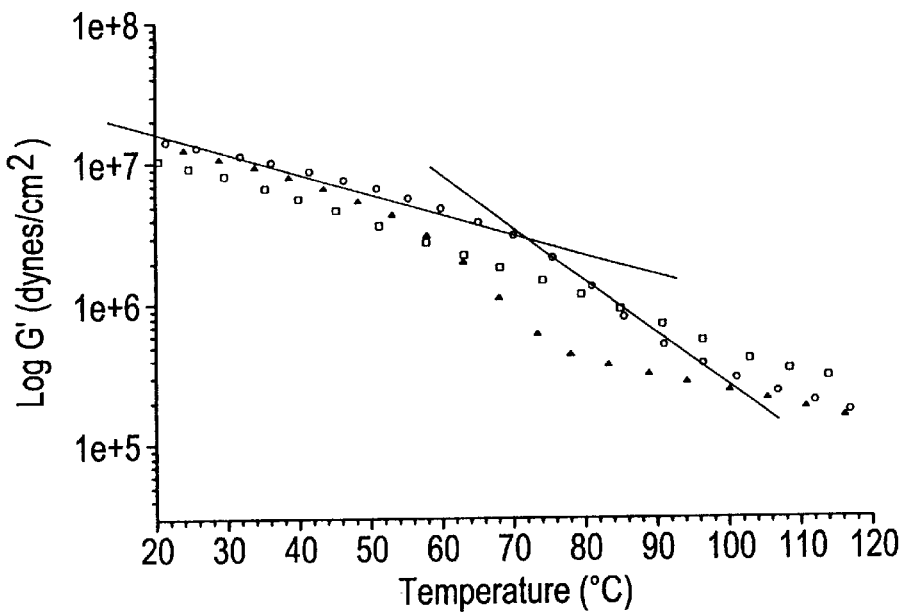

FIGS. 8a and 8b provide dynamic mechanical data for ethylene/octene interpolymers prepared with Catalysts One (Example 1a) and Catalyst Two (Example 2a), respectively, and for a ethylene/octene interpolymer of prepared with Catalyst Three. (Comparative Example C-3a).

Figure 9A:
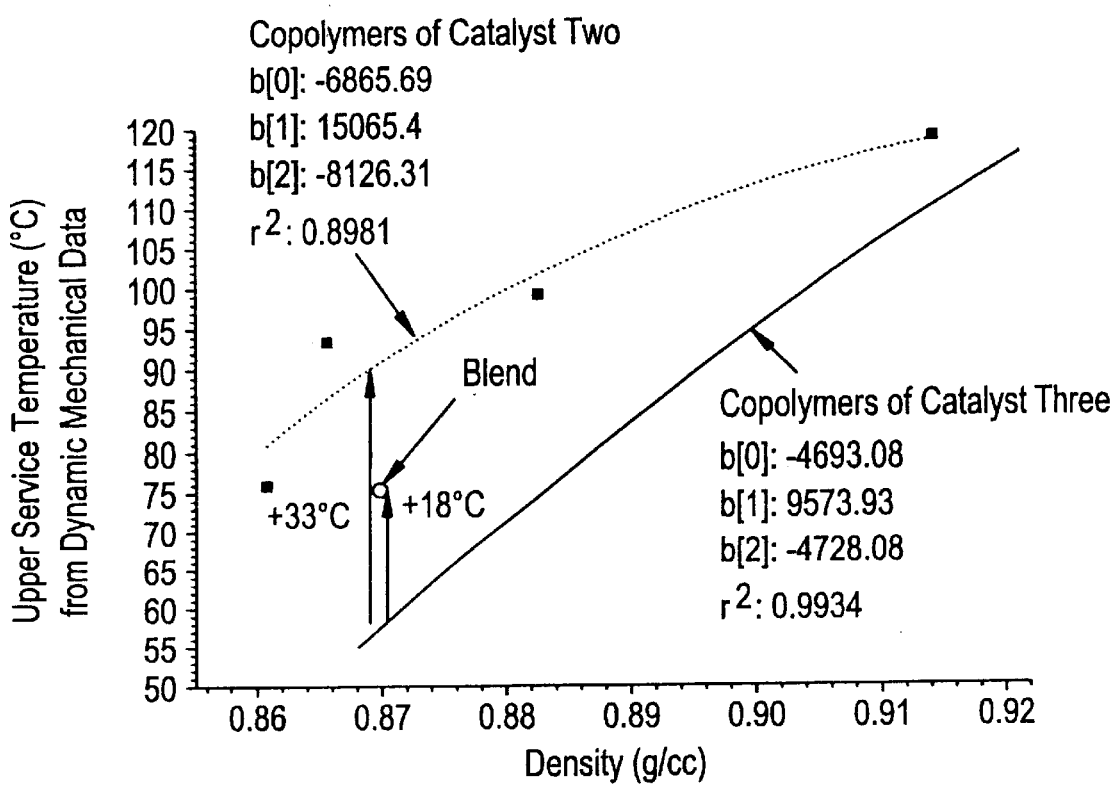

FIG. 9a is a plot of the upper service temperature (UST) of ethylene/octene interpolymers prepared with Catalyst Two and of comparative ethylene/octene interpolymers it prepared with Catalyst Three, and of a blend of two ethylene/octene interpolymers prepared with Catalyst Three.

FIG. 9a is a plot of the difference between the UST of various blends of ethylene/octene interpolymers prepared using Catalyst Three with the UST of interpolymers of the invention set forth in FIG. 9.

Figure 9B:
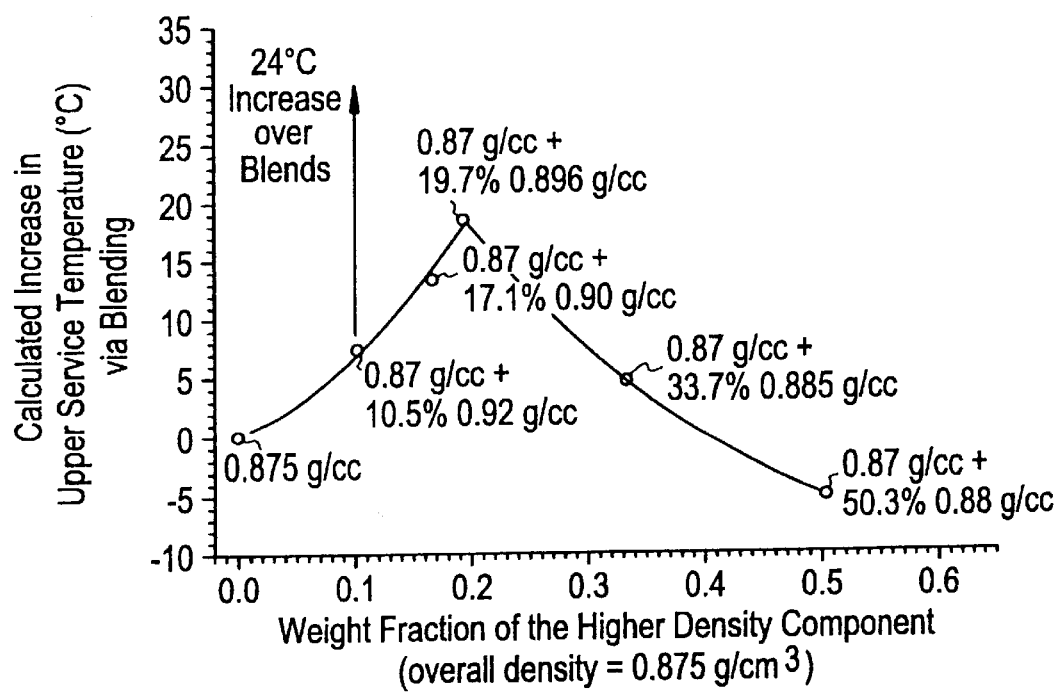

FIG. 9b is a plot of the difference between the UST of various blends of ethylene/octene interpolymers prepared using Catalyst Three with the UST of interpolymers of the invention set forth in FIG. 9a.

Figure 10:
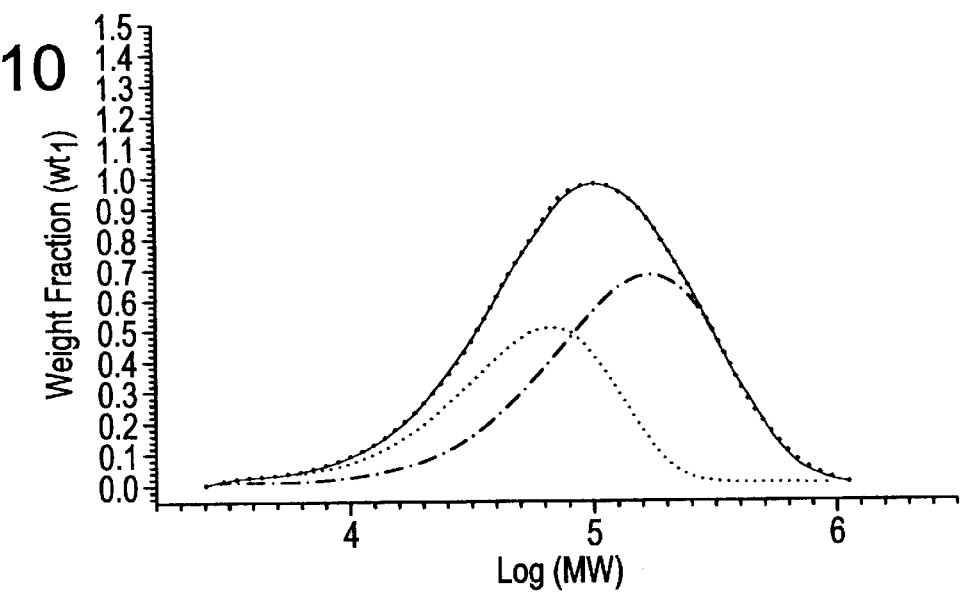

FIG. 10 is a deconvoluted gel permeation chromatogram of the ethylene/octene interpolymer of Example 1b prepared with Catalyst One.

Figure 11:
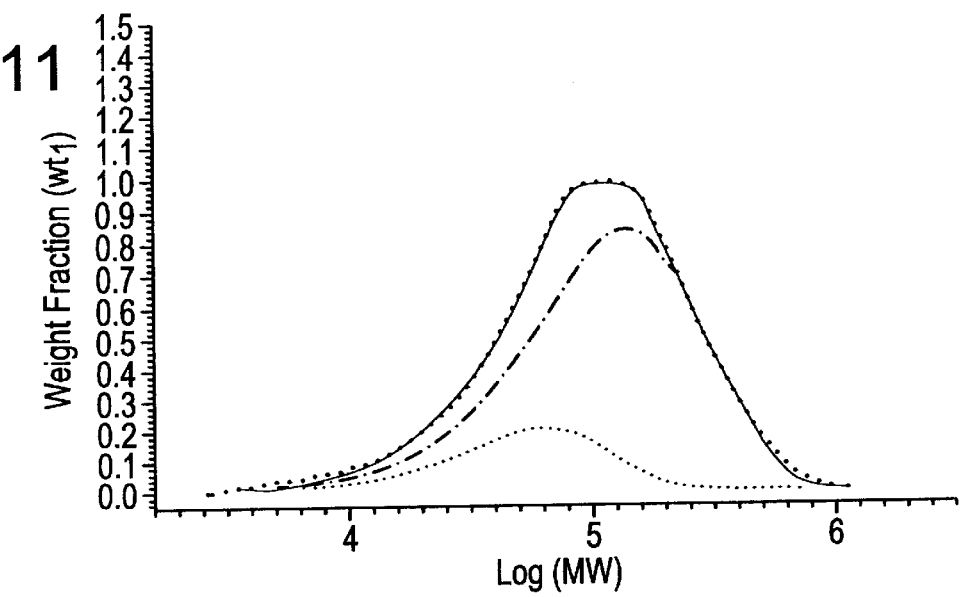

FIG. 11 is a deconvoluted gel permeation chromatogram of the ethylene/octene interpolymer of Example 2b prepared with Catalyst Two.

Figure 12:
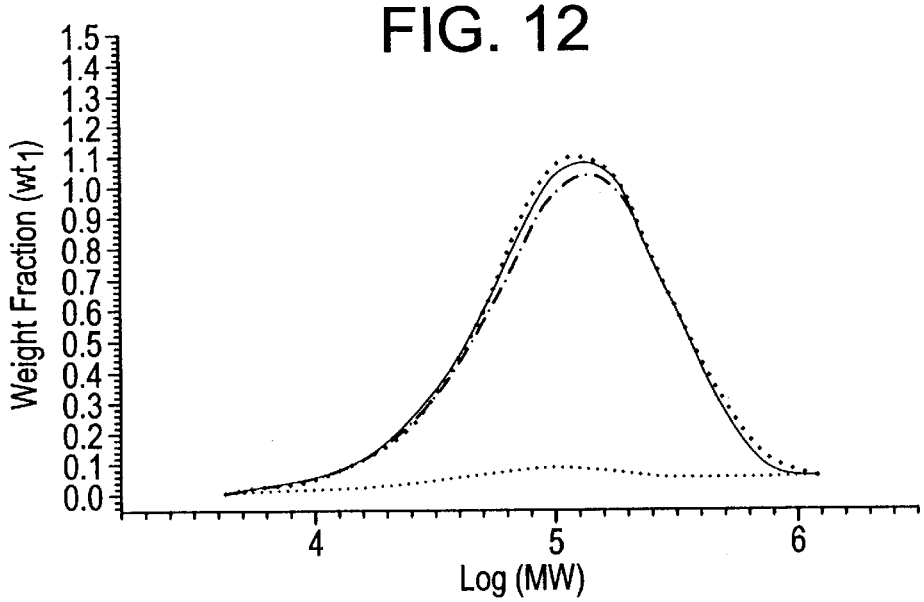

FIG. 12 is a deconvoluted gel permeation chromatogram of the ethylene/octene interpolymer of Comparative Example C-2a prepared with Catalyst Two and using a batch polymerization process.

Figure 13:
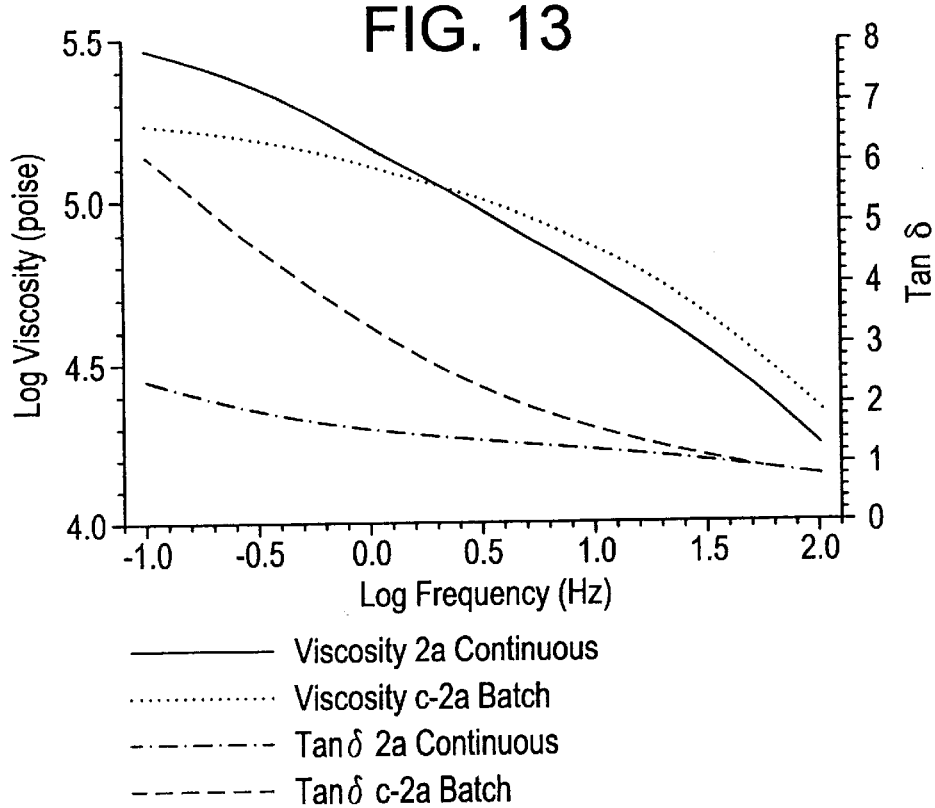

FIG. 13 are viscosity curves for the ethylene/octene interpolymers of Example 2a prepared using Catalyst Two in a continuous solution polymerization process and of Comparative Example C-2a prepared using Catalyst Three in a solution batch polymerization process.

Figure 14:
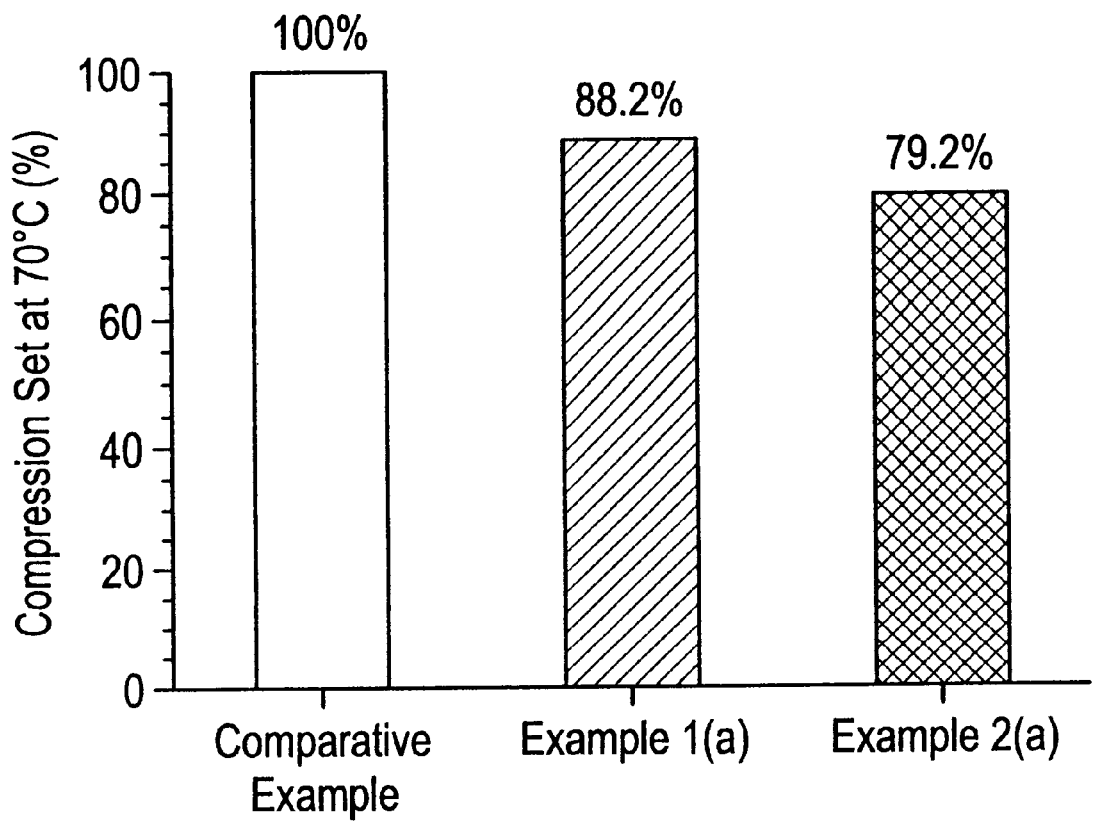

FIG. 14 is a depiction of the compression set of ethylene/octene interpolymers prepared using Catalysts One and Two, respectively, and of an ethylene/octene interpolymer prepared using Catalyst Three.

Figure 15:
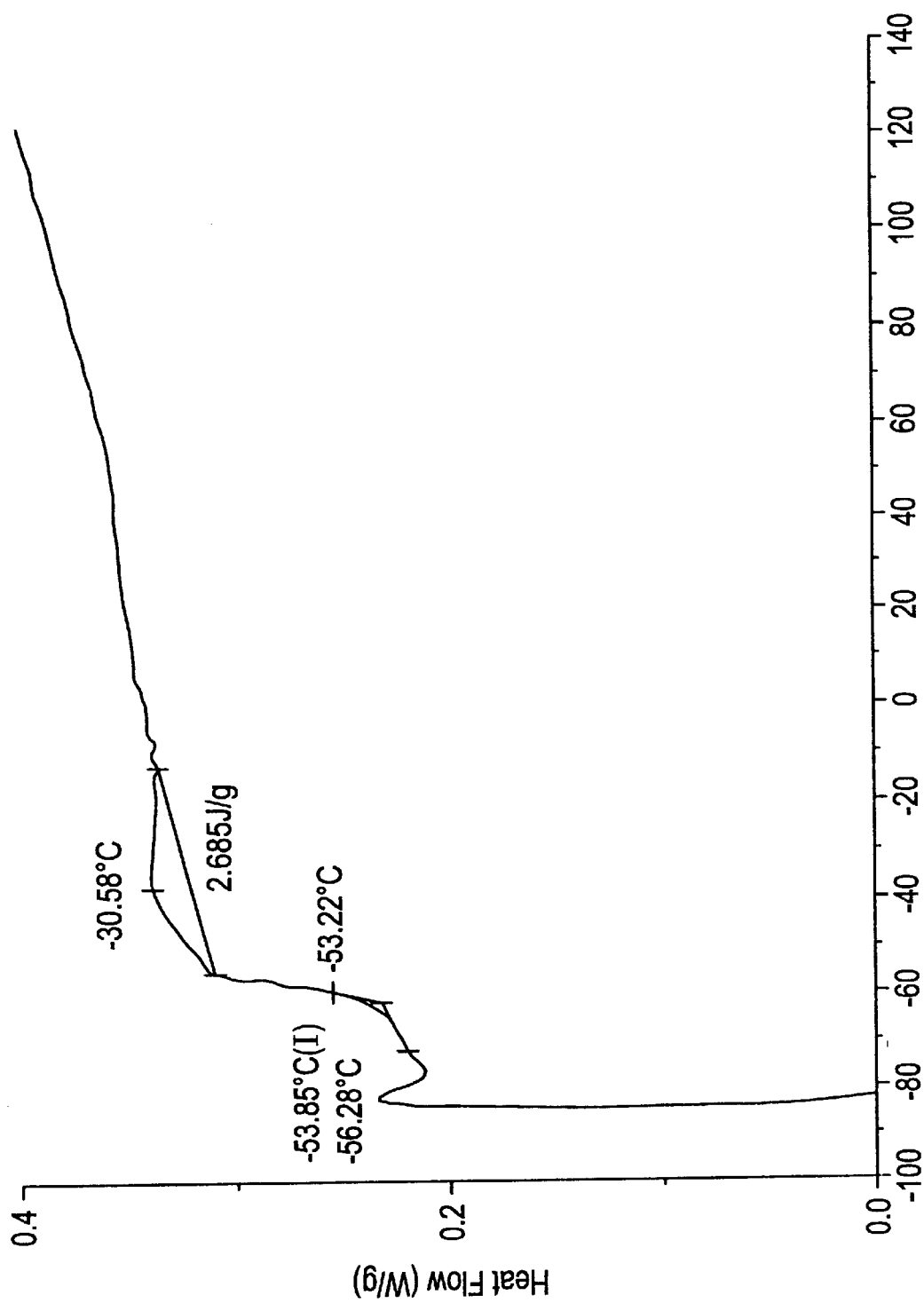
Figure 16:
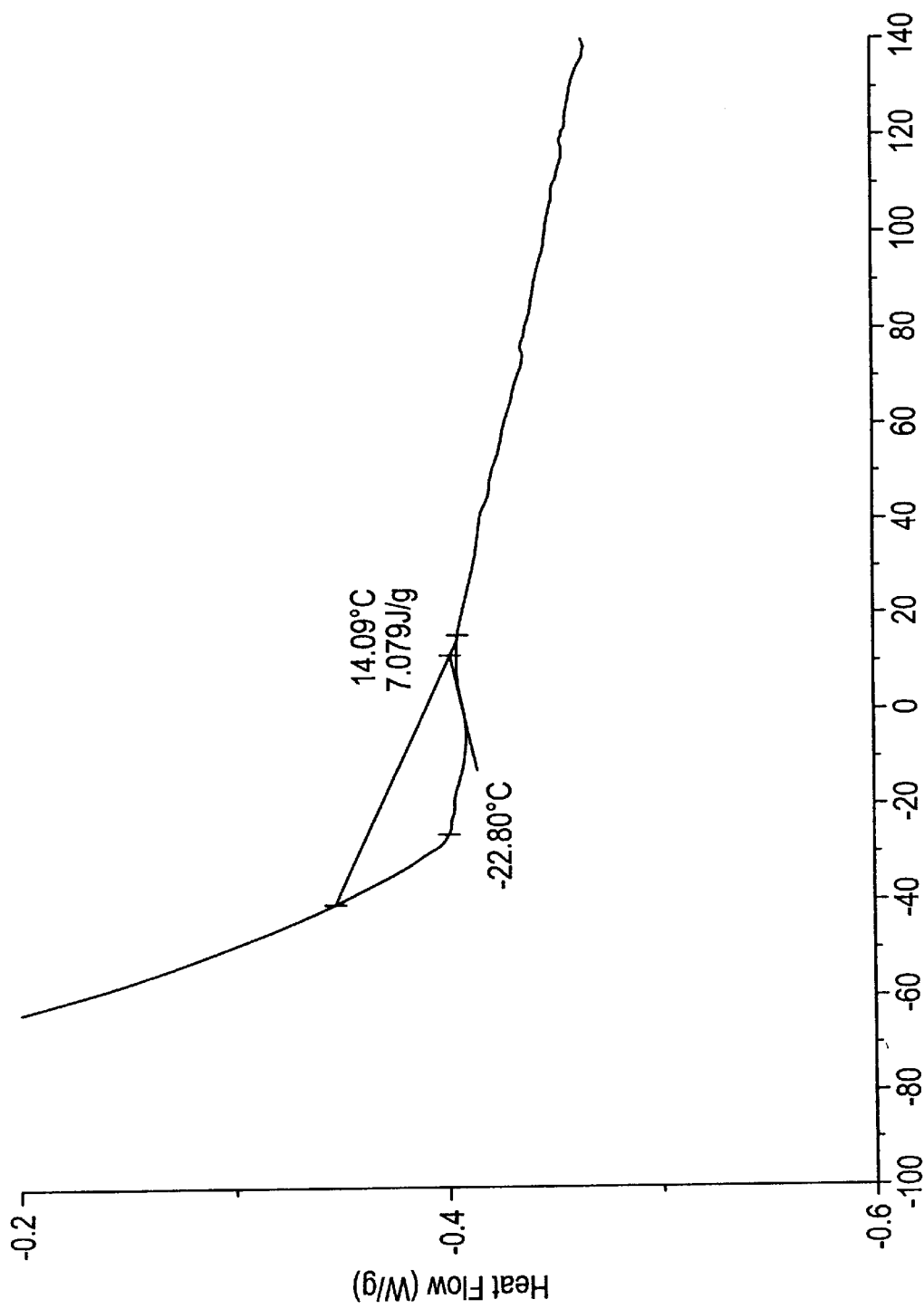

FIGS. 15 and 16 are DSC curves for an EPDM of the invention.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

Unless otherwise indicated, the following procedures are employed:

Density is measured in accordance with ASTM D-792. The samples are annealed at ambient conditions for 24 hours before the measurement is taken.

Melt index ($I_2$) is measured in accordance with ASTM D-1238, condition 190° C./2.16 kg (formally known as "Condition (E)").

$I_{10}$, is measured in accordance with ASTM D-1238, Condition 190° C./10 kg (formerly known as "Condition N").

Molecular weight is determined using gel permeation chromatography (GPC) on a Waters 150° C. high temperature chromatographic unit equipped with three mixed porosity columns (Polymer Laboratories 103, 104, 105, and 106), operating at a system temperature of 140° C. The solvent is 1,2,4-trichlorobenzene, from which 0.3 percent by weight solutions of the samples are prepared for injection. The flow rate is 1.0 mL/min. and the injection size is 100 microliters.

The molecular weight determination is deduced by using narrow molecular weight distribution polystyrene standards (from Polymer Laboratories) in conjunction with their elution volumes. The equivalent polyethylene molecular weights are determined by using appropriate Mark-Houwink coefficients for polyethylene and polystyrene (as described by Williams and Word in Journal of Polymer Science, Polymer Letters, Vol. 6, (621) 1968, incorporated herein by reference) to derive the following equation:

$$M_{polyethylene} = a*(M_{polystyrene})b.$$

In this equation, a=0.4316 and b=1.0. Weight average molecular weight, $M_w$, is calculated in the usual manner according to the following formula: $M_w = \Sigma w_i * M_i$, where $w_i$ and $M_i$ are the weight fraction and molecular weight, respectively, of the with fraction eluting from the GPC column.

Percent crystallinity is calculated with the equation:

$$\% C = (A/292 \text{ J/g}) \times 100,$$

in which % C represents the percent crystallinity and A represents the heat of fusion of the ethylene in Joules per gram (J/g) as determined by differential scanning calorimetry (DSC).

Differential scanning calorimetry (DSC) data was generated by placing each sample (5 mg) in an aluminum pan, the sample was heated to 160° C., cooled at 10° C./min and the endotherm was recorded by scanning from −30° C. to 140° C. at 10° C./min using a Perkin Elmer DSC 7. The DSC exotherm (cooling curve) was also recorded by scanning from 140 to −30 at 10° C./min.

The morphology of the copolymers were investigated by transmission electron microscopy (TEM). Samples were stained with ruthenium chloride-hypochlorite and then thin slices were prepared with a glass knife on a microtome at room temperature. Micrographs were recorded at 150000-fold magnification on a JEOL 2000FX microscope.

Analytical temperature rising elution fractionation (ATREF) data were generated using the standard equipment within Polyolefins Research. The polymer sample (dissolved in hot trichlorobenzene) was crystallized in a column containing an inert support (steel shot) by slowly reducing the temperature. An ATREF chromatogram was then generated by eluting the crystallized sample from the column by slowly increasing the temperature of the eluting solvent, trichlorobenzene. The ATREF curve illustrated several key structural features of the resin. For example, the response from the refractive index detector gives the short chain branching distribution; while the response from the differential viscometer detector provides an estimate of the viscosity average molecular weight.

Dynamic mechanical spectroscopy measurements were made on the RMS-800 dynamic mechanical spectrometer using 25 mm diameter parallel plates (gap 2 mm) in the oscillatory shear mode. Frequency sweeps were performed over the shear rate ranges of 0.1 to 100 rad/s at 15% strain in a nitrogen atmosphere at 190° C. Temperature sweeps were also performed on the RDAII dynamic analyzer. In this case 12.5 mm diameter parallel plates (gap 1.5 mm) were used over the temperature range from about −100° C. to 200° C. at a frequency of 1 rad/s in a nitrogen atmosphere. The sample was loaded at room temperature, heated to 60° C. to ensure good contact between the sample and the plates and then cooled to −100° C. prior to beginning the temperature sweep experiment.

Processability was evaluated using the gas extrusion rheometer (GER). The resin was packed into a capillary rheometer equipped with a 0.0296-in. diameter and 20 L/D cylindrical die operating at 190° C. Using nitrogen gas to pressurize the rheometer, samples of extrudate were collected as the pressure was decreased from 5500 to 1000 psi (38 to 6.9 MPa), in steps of 250 psi (1.7 MPa), generally, 19 copolymer samples were collected. After solidification, the surface of each extrudate was examined visually for surface flow defects, e.g., the point where each resin lost surface gloss (LSG) and the point where each resin became grossly melt fractured (OGMF) was determined.

Olefins as used herein are $C_{2-20}$ aliphatic or aromatic compounds containing vinylic unsaturation, as well as cyclic compounds such as cyclobutene, cyclopentene, and norbornene, including norbornene substituted in the 5 and 6 position with $C_{1-20}$ hydrocarbyl groups. Also included are mixtures of such olefins as well as mixtures of such olefins with $C_{4-40}$ diolefin compounds. Examples of the latter compounds include ethylidene norbornene, 1,4-hexadiene, norbornadiene, and the like. The catalysts and process herein are especially suited for use in preparation of ethylene/propylene, ethylene/1-butene, ethylene/1-pentene, ethylene/4-methyl-1-pentene, ethylene/1-hexene, ethylene/1-octene, and ethylene/styrene interpolymers as well as terpolymers of ethylene, propylene and a nonconjugated diene, that is EPDM terpolymers, with interpolymers of ethylene and a $C_3$–$C_{20}$ α-olefin, preferably at $C_4$–$C_{20}$ α-olefin, and more preferably a $C_6$–$C_{10}$ α-olefin, with ethylene/1-octene polymers being especially preferred.

The interpolymers of the invention will preferably be prepared using catalyst systems derived from a metal complex corresponding to the formula:

wherein:

M is titanium, zirconium or hafnium in the +2, +3 or +4 formal oxidation state;

A' is a substituted indenyl group substituted in at least the 2 or 3 position with a group selected from hydrocarbyl, fluoro-substituted hydrocarbyl, hydrocarbyloxy-substituted hydrocarbyl, dialkylamino-substituted hydrocarbyl, silyl, germyl and mixtures thereof, said group containing up to 40 nonhydrogen atoms, and said A' further being covalently bonded to M by means of a divalent Z group;

Z is a divalent moiety bound to both A' and M via σ-bonds, said Z comprising boron, or a member of Group 14 of the Periodic Table of the Elements, and also comprising nitrogen or phosphorus, wherein an aliphatic or alicyclic hydrocarbyl group is covalently bonded to the nitrogen or phosphorus via a primary or secondary carbon;

X is an anionic or dianionic ligand group having up to 60 atoms exclusive of the class of ligands that are cyclic, delocalized, π-bound ligand groups;

X' independently each occurrence is a neutral ligating compound, having up to 20 atoms;

p is 0, 1 or 2, and is two less than the formal oxidation state of M, with the proviso that when X is a dianionic ligand group, p is 1; and q is 0, 1 or 2.

Preferred X' groups are carbon monoxide; phosphines, especially trimethylphosphine, triethylphosphine, triphenylphosphine and bis(1,2-dimethylphosphino)ethane; $P(OR)_3$, wherein R is as previously defined; ethers, especially tetrahydrofuran; amines, especially pyridine, bipyridine, tetramethylethylenediamine (TMEDA), and triethylamine; olefins; and conjugated dienes having from 4 to 40 carbon atoms. Complexes including the latter X' groups include those wherein the metal is in the +2 formal oxidation state.

In the case of the above metal complexes, as well as in the case of the other metal complexes disclosed herein, M is preferably zirconium or titanium, and is more preferably titanium.

Preferred substituted indenyl coordination complexes used according to the present invention are complexes corresponding to the formula:

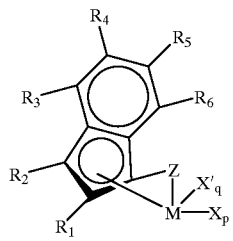

wherein:

$R_1$ and $R_2$, independently are groups selected from hydrogen, hydrocarbyl, perfluoro substituted hydrocarbyl, silyl, germyl and mixtures thereof, said group containing up to 20 nonhydrogen atoms, with the proviso that at least one of $R_1$ or $R_2$ is not hydrogen;

$R_3$, $R_4$, $R_5$, and $R_6$ independently are groups selected from hydrogen, hydrocarbyl, perfluoro substituted hydrocarbyl, silyl, germyl and mixtures thereof, said group containing up to 20 nonhydrogen atoms;

M is titanium, zirconium or hafnium;

Z is a divalent moiety comprising boron, or a member of Group 14 of the Periodic Table of the Elements, and also comprising nitrogen or phosphorus, said moiety having up to 60 non-hydrogen atoms, wherein an aliphatic or alicyclic hydrocarbyl group is covalently bonded to the nitrogen or phosphorus via a primary or secondary carbon;

p is 0, 1 or 2;

q is zero or one;

with the proviso that:
when p is 2, q is zero, M is in the +4 formal oxidation state, and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy- and di(hydrocarbyl)phosphino-substituted derivatives thereof, said X group having up to 20 nonhydrogen atoms, when p is 1, q is zero, M is in the +3 formal oxidation state, and X is a stabilizing anionic ligand group selected from the group consisting of allyl, 2-(N,N-dimethylaminomethyl)phenyl, and 2-(N,N-dimethyl)-aminobenzyl, or M is in the +4 formal oxidation state, and X is a divalent derivative of a conjugated diene, M and X together forming a metallocyclopentene group, and when p is 0, q is 1, M is in the +2 formal oxidation state, and X' is a neutral, conjugated or nonconjugated diene, optionally substituted with one or more hydrocarbyl groups, said X' having up to 40 carbon atoms and forming a π-complex with M.

More preferred coordination complexes used according to the present invention are complexes corresponding to the formula:

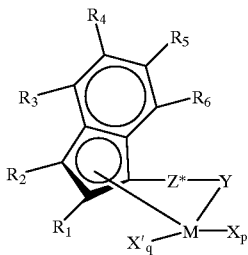

wherein:

$R_1$ and $R_2$ are hydrogen or $C_{1-6}$ alkyl, with the proviso that at least one of $R_1$ or $R_2$ is not hydrogen;

$R_3$, $R_4$, $R_5$, and $R_6$ independently are hydrogen or $C_{1-6}$ alkyl;

M is titanium;

Y is —NR—, —PR—;

Z* is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$;

R* each occurrence is independently hydrogen, or a member selected from hydrocarbyl, hydrocarbyloxy, silyl, halogenated alkyl, halogenated aryl, and combinations thereof, said R* having up to 20 non-hydrogen atoms, and optionally, two R* groups from Z (when R* is not hydrogen), or an R* group from Z and an R* group from Y form a ring system;

R** is a aliphatic or alicyclic hydrocarbyl group covalently bonded to the nitrogen or phosphorus of Y via a primary or secondary carbon;

p is 0, 1 or 2;

q is zero or one;

with the proviso that:
when p is 2, q is zero, M is in the +4 formal oxidation state, and X is independently at each occurrence methyl or benzyl, when p is 1, q is zero, M is in the +3 formal oxidation state, and X is 2-(N,N-dimethyl)aminobenzyl; or M is in the +4 formal oxidation state and X is 1,4-butadienyl, and when p is 0, q is 1, M is in the +2 formal oxidation state, and X' is 1,4-diphenyl-1,3-butadiene or 1,3-pentadiene. The latter diene is illustrative of unsymetrical diene groups that result in production of metal complexes that are actually mixtures of the respective geometrical isomers.

Preferred substituted indenecyl metal complexes correspond to the following formula:

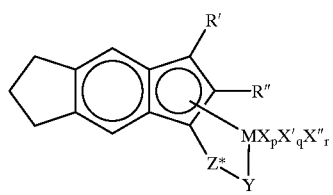

(II)

or

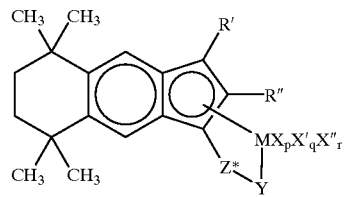

(III)

wherein:

R' is hydrocarbyl, di(hydrocarbylamino), or a hydrocarbyleneamino group, said R' having up to 20 carbon atoms, R" is $C_{1-20}$ hydrocarbyl or hydrogen;

M is titanium;

Y is —O—, —S—, —NR*—, —PR*—; —NR$_2$*, or —PR$_2$*;

Z* is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$;

R* each occurrence is independently hydrogen, or a member selected from hydrocarbyl, hydrocarbyloxy, silyl, halogenated alkyl, halogenated aryl, and combinations thereof, said R* having up to 20 non-hydrogen atoms, and optionally, two R* groups from Z (when R* is not hydrogen), or an R* group from Z and an R* group from Y form a ring system;

X, X' and X" are as previously defined;

p is 0, 1 or 2;

q is zero or 1; and r is zero or 1;

with the proviso that:
when p is 2, q and r are zero, M is in the +4 formal oxidation state (or M is in the +3 formal oxidation state if Y is —NR*$_2$ or —PR*$_2$), and X is an anionic ligand selected from the group consisting of halide, hydrocarbyl, hydrocarbyloxy, di(hydrocarbyl) amido, di(hydrocarbyl)phosphido, hydrocarbylsulfido, and silyl groups, as well as halo-, di(hydrocarbyl)amino-, hydrocarbyloxy-, and di(hydrocarbyl)phosphino-substituted derivatives thereof, said X group having up to 30 nonhydrogen atoms, when r is 1, p and q are zero, M is in the +4 formal oxidation state, and X' is a dianionic ligand selected from the group consisting of hydrocarbadiyl, oxyhydrocarbyl, and hydrocarbylenedioxy groups, said X group having up to 30 nonhydrogen atoms, when p is 1, q and r are zero, M is in the +3 formal oxidation state, and X is a stabilizing anionic ligand group selected from the group consisting of allyl, 2-(N,N-dimethylamino)phenyl, 2-(N,N-dimethylaminomethyl)phenyl, and 2-(N,N-dimethylamino)benzyl, and when p and r are zero, q is 1, M is in the +2 formal oxidation state, and X' is a neutral, conjugated or nonconjugated diene, optionally substituted with one or more hydrocarbyl groups, said X' having up to 40 carbon atoms and forming a π-complex with M.

Most preferred metal complexes are those according to the previous formula (II) or (III), wherein M, X, X', X", R' R", Z*, Y, p, q and r are as previously defined, with the proviso that:

when p is 2, q and r are zero, M is in the +4 formal oxidation state, and X is independently each occurrence methyl, benzyl, or halide;

when p and q are zero, r is one, and M is in the +4 formal oxidation state, X" is a 1,4-butadienyl group that forms a metallocyclopentene ring with M, when p is 1, q and r are zero, M is in the +3 formal oxidation state, and X is 2-(N,N-dimethylamino) benzyl; and when p and r are 0, q is 1, M is in the +2 formal oxidation state, and X' is 1,4-diphenyl-1,3-butadiene or 1,3-pentadiene.

Especially preferred coordination complexes corresponding to the previous formulas (II) and (III) are uniquely substituted depending on the particular end use thereof. In particular, highly useful metal complexes for use in catalyst compositions for the copolymerization of ethylene, one or more monovinyl aromatic monomers, and optionally an α-olefin or diolefin comprise the foregoing complexes (II) or (III) wherein R' is $C_{6-20}$ aryl, especially phenyl, biphenyl or naphthyl, and R" is hydrogen or methyl, especially hydrogen.

Highly useful metal complexes for use in catalyst compositions for the homopolymerization of ethylene or the copolymerization of ethylene and one or more α-olefins, especially 1-butene, 1-hexene or 1-octene, comprise the foregoing complexes (II) or (III) wherein R' is $C_{1-4}$ alkyl, N,N-dimethylamino or 1-pyrrolidinyl, and R" is hydrogen or $C_{1-4}$ alkyl. Moreover, in such complexes, Y is preferably a cyclohexylamido group, X is methyl, p is two, and both q and r are zero. Most preferably such complexes are 2,3-dimethyl-substituted s-indecenyl complexes corresponding to the formulas:

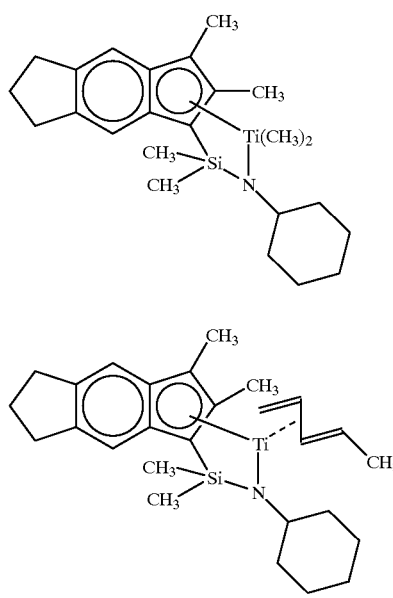

Finally, highly useful metal complexes for use in catalyst compositions for the copolymerization of ethylene, an α-olefin and a diene, especially ethylene, propylene and a nonconjugated diene, such as ethylidenenorbornene or 1,4-hexadiene, or the conjugated diene piperylene comprise the foregoing complexes (II) or (III) wherein R' is hydrogen, and R" is $C_{1-4}$ alkyl, especially methyl.

Highly preferred metal complexes are:
2-methylindenyl complexes:
(n-butylamido)dimethyl($\eta^5$-2-methylindenyl) silanetitanium (II) 1,4-diphenyl-1,3-butadiene, (n-butylamido)dimethyl($\eta^5$-2-methylindenyl) silanetitanium (II) 1,3-pentadiene,
(n-butylamido)dimethyl($\eta^5$-2-methylindenyl) silanetitanium (III) 2-(N,N-dimethylamino)benzyl,
(n-butylamido)dimethyl($\eta^5$-2-methylindenyl) silanetitanium (IV) dimethyl,
(n-butylamido)dimethyl($\eta^5$-2-methylindenyl) silanetitanium (IV) dibenzyl,
(cyclohexylamido)dimethyl($\eta^5$-2-methylindenyl) silanetitanium (II) 1,4-diphenyl-1,3-butadiene,
(cyclohexylamido)dimethyl($\eta^5$-2-methylindenyl) silanetitanium (II) 1,3-pentadiene,
(cyclohexylamido)dimethyl($\eta^5$-2-methylindenyl) silanetitanium (III) 2-(N,N-dimethylamino)benzyl,
(cyclohexylamido)dimethyl($\eta^5$-2-methylindenyl) silanetitanium (IV) dimethyl,
(cyclohexylamido)dimethyl($\eta^5$-2-methylindenyl) silanetitanium (IV) dibenzyl,
(isopropylamido)dimethyl($\eta^5$-2-methylindenyl) silanetitanium (II) 1,4-diphenyl-1,3-butadiene,
(isopropylamido)dimethyl($\eta^5$-2-methylindenyl) silanetitanium (II) 1,3-pentadiene,
(isopropylamido)dimethyl($\eta^5$-2-methylindenyl) silanetitanium (III) 2-(N,N-dimethylamino)benzyl,
(isopropylamido)dimethyl($\eta^5$-2-methylindenyl) silanetitanium (IV) dimethyl,
(isopropylamido)dimethyl($\eta^5$-2-methylindenyl) silanetitanium (IV) dibenzyl,
(cyclopentylamido)dimethyl($\eta^5$-2-methylindenyl) silanetitanium (II) 1,4-diphenyl-1,3-butadiene,
(cyclopentylamido)dimethyl($\eta^5$-2-methylindenyl) silanetitanium (II) 1,3-pentadiene,
(cyclopentylamido)dimethyl($\eta^5$-2-methylindenyl) silanetitanium (III) 2-(N,N-dimethylamino)benzyl,
(cyclopentylamido)dimethyl($\eta^5$-2-methylindenyl) silanetitanium (IV) dimethyl,
(cyclopentylamido)dimethyl($\eta^5$-2-methylindenyl) silanetitanium (IV) dibenzyl,
(cyclododecylamido)dimethyl($\eta^5$-2-methylindenyl) silanetitanium (II) 1,4-diphenyl-1,3-butadiene,
(cyclododecylamido)dimethyl($\eta^5$-2-methylindenyl) silanetitanium (II) 1,3-pentadiene,
(cyclododecylamido)dimethyl($\eta^5$-2-methylindenyl) silanetitanium (III) 2-(N,N-dimethylamino)benzyl,
(cyclododecylamido)dimethyl($\eta^5$-2-methylindenyl) silanetitanium (IV) dimethyl,
(cyclododecylamido)dimethyl($\eta^5$-2-methylindenyl) silanetitanium (IV) dibenzyl,
(isobutylamido)dimethyl($\eta^5$-2-methylindenyl) silanetitanium (II) 1,4-diphenyl-1,3-butadiene,
(isobutylamido)dimethyl($\eta^5$-2-methylindenyl) silanetitanium (II) 1,3-pentadiene,
(isobutylamido)dimethyl($\eta^5$-2-methylindenyl) silanetitanium (III) 2-(N,N-dimethylamino)benzyl,
(isobutylamido)dimethyl($\eta^5$-2-methylindenyl) sianetitanium (IV) dimethyl,
(isobutylamido)dimethyl($\eta^5$-2-methylindenyl) silanetitanium (IV) dibenzyl,
(n-butylamido)diisopropoxy($\eta^5$-2-methylindenyl) silanetitanium (II) 1,4-diphenyl-1,3-butadiene,
(n-butylamido)diisopropoxy($\eta^5$-2-methylindenyl) silanetitanium (II) 1,3-pentadiene, (n-butylamido)diisopropoxy($\eta^5$-2-methylindenyl)
silanetitanium (III) 2-(N,N-dimethylamino)benzyl,
(n-butylamido)diisopropoxy($\eta^5$-2-methylindenyl)
silanetitanium (IV) dimethyl,
(n-butylamido)diisopropoxy($\eta^5$-2-methylindenyl)
sianetitanium (IV) dibenzyl,
(n-butylamido)dimethoxy($\eta^5$-2-methylindenyl)
silanetitanium (II) 1,4-diphenyl-1,3-butadiene,
(n-butylamido)dimethoxy($\eta^5$-2-methylndenyl)
silanetitanium (II) 1,3-pentadiene,
(n-butylamido)dimethoxy($\eta^5$-2-methylindenyl)
silanetitanium (III) 2-(N,N-dimethylamino)benzyl,
(n-butylamido)dimethoxy($\eta^5$-2-methylindenyl)
silanetitanium (IV) dimethyl,
(n-butylamido)dimethoxy($\eta^5$-2-methylindenyl)
silanetitanium (IV) dibenzyl,
(cyclododecylamido)dimethoxy($\eta^5$-2-methylindenyl)
silanetitanium (II) 1,4-diphenyl-1,3-butadiene,
(cyclododecylamido)dimethoxy($\eta^5$-2-methylindenyl)
silanetitanium (II) 1,3-pentadiene,
(cyclododecylamido)dimethoxy($\eta^5$-2-methylindenyl)
silanetitanium (III) 2-(N,N-dimethylamino)benzyl,
(cyclododecylamido)dimethoxy($\eta^5$-2-methylindenyl)
silanetitanium (IV) dimethyl,
(cyclododecylamido)dimethoxy($\eta^5$-2-methylindenyl)
silanetitanium (IV) dibenzyl,
(n-butylamido)ethoxymethyl($\eta^5$-2-methylindenyl)
silanetitanium (II) 1,4-diphenyl-1,3-butadiene,
(n-butylamido)ethoxymethyl($\eta^5$-2-methylindenyl)
silanetitanium (II) 1,3-pentadiene,
(n-butylamido)ethoxymethyl($\eta^5$-2-methylindenyl)
silanetitanium (III) 2-(N,N-dimethylamino)benzyl,
(n-butylamido)ethoxymethyl($\eta^5$-2-methylindenyl)
silanetitanium (IV) dimethyl,
(n-butylamido)ethoxymethyl($\eta^5$-2-methylindenyl)
silanetitanium (IV) dibenzyl,
(cyclododecylamido)ethoxymethyl($\eta^5$-2-methylindenyl)
silanetitanium (II) 1,4-diphenyl-1,3-butadiene,
(cyclododecylamido)ethoxymethyl($\eta^5$-2-methylindenyl)
silanetitanium (II) 1,3-pentadiene,
(cyclododecylamido)ethoxymethyl($\eta^5$-2-methylindenyl)
silanetitanium (III) 2-(N,N-dimethylamino)benzyl,
(cyclododecylamido)ethoxymethyl($\eta^5$-2-methylindenyl)
silanetitanium (IV) dimethyl,
(cyclododecylamido)ethoxymethyl($\eta^5$-2-methylindenyl)
silanetitanium (IV) dibenzyl,
2,3-dimethylindenyl complexes:
(n-butylamido)dimethyl($\eta^5$-2,3-dimethylindenyl)-
silanetitanium (II) 1,4-diphenyl-1,3-butadiene,
(n-butylamido)dimethyl($\eta^5$-2,3-dimethylindenyl)
silanetitanium (II) 1,3-pentadiene,
(n-butylamido)dimethyl($\eta^5$-2,3-dimethylindenyl)-
silanetitanium (III) 2-(N,N-dimethylamino)benzyl,
(n-butylamido)dimethyl($\eta^5$-2,3-dimethylindenyl)
silanetitanium (IV) dimethyl,
(n-butylamido)dimethyl($\eta^5$-2,3-dimethylindenyl)
silanetitanium (IV) dibenzyl,
(cyclohexylamido)dimethyl($\eta^5$-2,3-dimethylindenyl)
silanetitanium (II) 1,4-diphenyl-1,3-butadiene,
(cyclohexylamido)dimethyl($\eta^5$-2,3-dimethylindenyl)
silanetitanium (II) 1,3-pentadiene,
(cyclohexylamido)dimethyl($\eta^5$-2,3-dimethylindenyl)
silanetitanium (III) 2-(N,N-dimethylamino)benzyl,
(cyclohexylamido)dimethyl($\eta^5$-2,3-dimethylindenyl)
silanetitanium (IV) dimethyl,
(cyclohexylamido)dimethyl($\eta^5$-2,3-dimethylindenyl)
silanetitanium (IV) dibenzyl,
(isopropylamido)dimethyl($\eta^5$-2,3-dimethylindenyl)
silanetitanium (II) 1,4-diphenyl-1,3-butadiene,
(isopropylamido)dimethyl($\eta^5$-2,3-dimethylindenyl)
silanetitanium (II) 1,3-pentadiene,
(isopropylamido)dimethyl($\eta^5$-2,3-dimethylindenyl)
silanetitanium (III) 2-(N,N-dimethylamino)benzyl,
(isopropylamido)dimethyl($\eta^5$-2,3-dimethylindenyl)
silanetitanium (IV) dimethyl,
(isopropylamido)dimethyl($\eta^5$-2,3-dimethylindenyl)
silanetitanium (IV) dibenzyl,
(cyclopentylamido)dimethyl($\eta^5$-2,3-dimethylindenyl)
silanetitanium (II) 1,4-diphenyl-1,3-butadiene,
(cyclopentylamido)dimethyl($\eta^5$-2,3-dimethylindenyl)
silanetitanium (II) 1,3-pentadiene,
(cyclopentylamido)dimethyl($\eta^5$-2,3-dimethylindenyl)
silanetitanium (III) 2-(N,N-dimethylamino)benzyl,
(cyclopentylamido)dimethyl($\eta^5$-2,3-dimethylindenyl)
silanetitanium (IV) dimethyl,
(cyclopentylamido)dimethyl($\eta^5$-2,3-dimethylindenyl)
silanefitanium (IV) dibenzyl,
(cyclododecylamido)dimethyl($\eta^5$-2,3-dimethylindenyl)
silanetitanium (II) 1,4-diphenyl-1,3-butadiene,
(cyclododecylamido)dimethyl($\eta^5$-2,3-dimethylindenyl)
silanetitanium (II) 1,3-pentadiene,
(cyclododecylamido)dimethyl($\eta^5$-2,3-dimethylindenyl)
silanetitanium (III) 2-(N,N-dimethylamino)benzyl,
(cyclododecylamido)dimethyl($\eta^5$-2,3-dimethylindenyl)
silanetitanium (IV) dimethyl,
(cyclododecylamido)dimethyl($\eta^5$-2,3-dimethylindenyl)
silanetitanium (IV) dibenzyl,
(isobutylamido)dimethyl($\eta^5$-2,3-dimethylindenyl)
silanetitanium (II) 1,4-diphenyl-1,3-butadiene,
(isobutylamido)dimethyl($\eta^5$-2,3-dimethylindenyl)
silanetitanium (II) 1,3-pentadiene,
(isobutylamido)dimethyl($\eta^5$-2,3-dimethylindenyl)
silanetitanium (III) 2-(N,N-dimethylamino)benzyl,
(isobutylamido)dimethyl($\eta^5$-2,3-dimethylindenyl)
silanetitanium (IV) dimethyl,
(isobutylamido)dimethyl($\eta^5$-2,3-dimethylindenyl)
silanetitanium (IV) dibenzyl,
(n-butylamido)diisopropoxy($\eta^5$-2,3-dimethylindenyl)
silanetitanium (II) 1,4-diphenyl-1,3-butadiene,
(n-butylamido)diisopropoxy($\eta^5$-2,3-dimethylindenyl)
silanetitanium (II) 1,3-pentadiene,
(n-butylamido)diisopropoxy($\eta^5$-2,3-dimethylindenyl)
silanetitanium (III) 2-(N,N-dimethylamino)benzyl,
(n-butylamido)diisopropoxy($\eta^5$-2,3-dimethylindenyl)
silanetitanium (IV) dimethyl,
(n-butylamido)diisopropoxy($\eta^5$-2,3-dimethylindenyl)
silanetitanium (IV) dibenzyl,
(cyclododecylamido)diisopropoxy($\eta^5$-2,3-
dimethylindenyl)-silanetitanium (II) 1,4-diphenyl-1,3-
butadiene,
(cyclododecylamido)diisopropoxy($\eta^5$-2,3-
dimethylindenyl)-silanetitanium (II) 1,3-pentadiene,
(cyclododecylamido)diisopropoxy($\eta^5$-2,3-
dimethylindenyl)-silanetitanium (III) 2-(N,N-
dimethylamino)benzyl, (cyclododecylamido)diisopropoxy($\eta^5$-2,3-dimethylindenyl)-silanetitanium (IV) dimethyl,
(cyclododecylamido)diisopropoxy($\eta^5$-2,3-dimethylindenyl)-silanefitanium (IV) dibenzyl,
(n-butylamido)dimethoxy($\eta^5$-2,3-dimethylindenyl) silanetitanium (II) 1,4-diphenyl-1,3-butadiene,
(n-butylamido)dimethoxy($\eta^5$-2,3-dimethylindenyl) silanefitanium (II) 1,3-pentadiene,
(n-butylamido)dimethoxy($\eta^5$-2,3-dimethylindenyl) silanetitanium (III) 2-(N,N-dimethylamino)benzyl,
(n-butylamido)dimethoxy($\eta^5$-2,3-dimethylindenyl) silanetitanium (IV) dimethyl,
(n-butylamido)dimethoxy($\eta^5$-2,3-dimethylindenyl) silanetitanium (IV) dibenzyl,
(cyclododecylamido)dimethoxy($\eta^5$-2,3-dimethylindenyl) silanetitanium (II) 1,4-diphenyl-1,3-butadiene,
(cyclododecylamido)dimethoxy($\eta^5$-2,3-dimethylindenyl) silanetitanium (II) 1,3-pentadiene,
(cyclododecylamido)dimethoxy($\eta^5$-2,3-dimethylindenyl) silanetitanium (III) 2-(N,N-dimethylamino)benzyl,
(cyclododecylamido)dimethoxy($\eta^5$-2,3-dimethylindenyl) silanetitanium (IV) dimethyl,
(cyclododecylamido)dimethoxy($\eta^5$-2,3-dimethylindenyl) silanetitanium (IV) dibenzyl,
(n-butylamido)ethoxymethyl($\eta^5$-2,3-dimethylindenyl) silanetitanium (II) 1,4-diphenyl-1,3-butadiene,
(n-butylamido)ethoxymethyl($\eta^5$-2,3-dimethylindenyl) silanetitanium (II) 1,3-pentadiene,
(n-butylamido)ethoxymethyl($\eta^5$-2,3-dimethylindenyl) silanetitanium (III) 2-(N,N-dimethylamino)benzyl,
(n-butylamido)ethoxymethyl($\eta^5$-2,3-dimethylindenyl) silanettanium (IV) dimethyl,
(n-butylamido)ethoxymethyl($\eta^5$-2,3-dimethylindenyl) silanetitanium (IV) dibenzyl,
(cyclododecylamido)ethoxymethyl($\eta^5$-2,3-dimethylindenyl)silanetitanium (II) 1,4-diphenyl-1,3-butadiene,
(cyclododecylamido)ethoxymethyl($\eta^5$-2,3-dimethylindenyl)silanetitanium (II) 1,3-pentadiene,
(cyclododecylamido)ethoxymethyl($\eta^5$-2,3-dimethylindenyl)silanefitanium (III) 2-(N,N-dimethylamino)benzyl,
(cyclododecylamido)ethoxymethyl($\eta^5$-2,3-dimethylindenyl)silanetitanium (IV) dimethyl,
(cyclododecylamido)ethoxymethyl($\eta^5$-2,3-dimethylindenyl)silanetitanium (IV) dibenzyl,
3-methylindenyl complexes:
(n-butylamido)dimethyl($\eta^5$-3-methylindenyl) silanetitanium (II) 1,4-diphenyl-1,3-butadiene,
(n-butylamido)dimethyl($\eta^5$-3-methylindenyl) silanetitanium (II) 1,3-pentadiene,
(n-butylamido)dimethyl($\eta^5$-3-methylindenyl) silanetitanium (III) 2-(N,N-dimethylamino)benzyl,
(n-butylamido)dimethyl($\eta^5$-3-methylindenyl) silanetitanium (IV) dimethyl,
(n-butylamido)dimethyl($\eta^5$-3-methylindenyl) silanetitanium (IV) dibenzyl,
(cyclohexylamido)dimethyl($\eta^5$-3-methylindenyl) silanetitanium (II) 1,4-diphenyl-1,3-butadiene,
(cyclohexylamido)dimethyl($\eta^5$-3-methylindenyl) silanetitanium (II) 1,3-pentadiene,
(cyclohexylamido)dimethyl($\eta^5$-3-methylindenyl) silanetitanium (III) 2-(N,N-dimethylamino)benzyl,
(cyclohexylamido)dimethyl($\eta^5$-3-methylindenyl) silanetitanium (IV) dimethyl,
(cyclohexylamido)dimethyl($\eta^5$-3-methylindenyl) silanetitanium (IV) dibenzyl,
(isopropylamido)dimethyl($\eta^5$-3-methylindenyl) silanetitanium (II) 1,4-diphenyl-1,3-butadiene,
(isopropylamido)dimethyl($\eta^5$-3-methylindenyl) silanetitanium (II) 1,3-pentadiene,
(isopropylamido)dimethyl($\eta^5$-3-methylindenyl) silanetitanium (III) 2-(N,N-dimethylamino)benzyl,
(isopropylamido)dimethyl($\eta^5$-3-methylindenyl) silanetitanium (IV) dimethyl,
(isopropylamido)dimethyl($\eta^5$-3-methylindenyl) silanetitanium (IV) dibenzyl,
(cyclopentylamido)dimethyl($\eta^5$-3-methylindenyl) silanetitanium (II) 1,4-diphenyl-1,3-butadiene,
(cyclopentylamido)dimethyl($\eta^5$-3-methylindenyl) silanetitanium (II) 1,3-pentadiene,
(cyclopentylamido)dimethyl($\eta^5$-3-methylindenyl) silanetitanium (III) 2-(N,N-dimethylamino)benzyl,
(cyclopentylamido)dimethyl($\eta^5$-3-methylindenyl) silanetitanium (IV) dimethyl,
(cyclopentylamido)dimethyl($\eta^5$-3-methylindenyl) silanetitanium (IV) dibenzyl,
(cyclododecylamido)dimethyl($\eta^5$-3-methylindenyl) silanetitanium (II) 1,4-diphenyl-1,3-butadiene,
(cyclododecylamido)dimethyl($\eta^5$-3-methylindenyl) silanetitanium (II) 1,3-pentadiene,
(cyclododecylamido)dimethyl($\eta^5$-3-methylindenyl) silanetitanium (III) 2-(N,N-dimethylamino)benzyl,
(cyclododecylamido)dimethyl($\eta^5$-3-methylindenyl) silanetitanium (IV) dimethyl,
(cyclododecylamido)dimethyl($\eta^5$-3-methylindenyl) silanetitanium (IV) dibenzyl,
(isobutylamido)dimethyl($\eta^5$-3-methylindenyl) silanetitanium (II) 1,4-diphenyl-1,3-butadiene,
(isobutylamido)dimethyl($\eta^5$-3-methylindenyl) silanetitanium (II) 1,3-pentadiene,
(isobutylamido)dimethyl($\eta^5$-3-methylindenyl) silanetitanium (III) 2-(N,N-dimethylamino)benzyl,
(isobutylamido)dimethyl($\eta^5$-3-methylindenyl) silanetitanium (IV) dimethyl,
(isobutylamido)dimethyl($\eta^5$-3-methylindenyl) silanetitanium (IV) dibenzyl,
(n-butylamido)diisopropoxy($\eta^5$-3-methylindenyl) silanetitanium (II) 1,4-diphenyl-1,3-butadiene,
(n-butylamido)diisopropoxy($\eta^5$-3-methylindenyl) silanetitanium (II) 1,3-pentadiene,
(n-butylamido)diisopropoxy($\eta^5$-3-methylindenyl) silanetitanium (III) 2-(N,N-dimethylamino)benzyl,
(n-butylamido)diisopropoxy($\eta^5$-3-methylindenyl) silanetitanium (IV) dimethyl,
(n-butylamido)diisopropoxy($\eta^5$-3-methylindenyl) silanetitanium (IV) dibenzyl,
(cyclododecylamido)diisopropoxy($\eta^5$-3-methylindenyl)-silanetitanium (II) 1,4-diphenyl-1,3-butadiene,
(cyclododecylamido)diisopropoxy($\eta^5$-3-methylindenyl)-silanetitanium (II) 1,3-pentadiene,
(cyclododecylamido)diisopropoxy($\eta^5$-3-methylindenyl)-silanetitanium (III) 2-(N,N-dimethylamino)benzyl,
(cyclododecylamido)diisopropoxy($\eta^5$-3-methylindenyl)-silanetitanium (IV) dimethyl, (cyclododecylamido)diisopropoxy($\eta^5$-3-methylindenyl)-silanetitanium (IV) dibenzyl,
(n-butylamido)dimethoxy($\eta^5$-3-methylindenyl) silanetitanium (II) 1,4-diphenyl-1,3-butadiene,
(n-butylamido)dimethoxy($\eta^5$-3-methylindenyl) silanefitanium (II) 1,3-pentadiene,
(n-butylamido)dimethoxy($\eta^5$-3-methylindenyl) silanetitanium (III) 2-(N,N-dimethylamino)benzyl,
(n-butylamido)dimethoxy($\eta^5$-3-methylindenyl) silanetitanium (IV) dimethyl,
(n-butylamido)dimethoxy($\eta^5$-3-methylindenyl) silanetitanium (IV) dibenzyl,
(cyclododecylamido)dimethoxy($\eta^5$-3-methylindenyl) silanetitanium (II) 1,4-diphenyl-1,3-butadiene,
(cyclododecylamido)dimethoxy($\eta^5$-3-methylindenyl) silanetitanium (II) 1,3-pentadiene,
(cyclododecylamido)dimethoxy($\eta^5$-3-methylindenyl) silanetitanium (III) 2-(N,N-dimethylamino)benzyl,
(cyclododecylamido)dimethoxy($\eta^5$-3-methylindenyl) silanetitanium (IV) dimethyl,
(cyclododecylamido)dimethoxy($\eta^5$-3-methylindenyl) silanetitanium (IV) dibenzyl,
(n-butylamido)ethoxymethyl($\eta^5$-3-methylindenyl) silanetitanium (II) 1,4-diphenyl-1,3-butadiene,
(n-butylamido)ethoxymethyl($\eta^5$-3-methylindenyl) silanetitanium (II) 1,3-pentadiene,
(n-butylamido)ethoxymethyl($\eta^5$-3-methylindenyl) silanetitanium (III) 2-(N,N-dimethylamino)benzyl,
(n-butylamido)ethoxymethyl($\eta^5$-3-methylindenyl) silanetitanium (IV) dimethyl,
(n-butylamido)ethoxymethyl($\eta^5$-3-methylindenyl) silanetitanium (IV) dibenzyl,
(cyclododecylamido)ethoxymethyl($\eta^5$-3-methylindenyl) silanetitanium (II) 1,4-diphenyl-1,3-butadiene,
(cyclododecylamido)ethoxymethyl($\eta^5$-3-methylindenyl) silanetitanium (II) 1,3-pentadiene,
(cyclododecylamido)ethoxymethyl($\eta^5$-3-methylindenyl) silanetitanium (III) 2-(N,N-dimethylamino)benzyl,
(cyclododecylamido)ethoxymethyl($\eta^5$-3-methylindenyl) silanetitanium (IV) dimethyl,
(cyclododecylamido)ethoxymethyl($\eta^5$-3-methylindenyl) silanetitanium (IV) dibenzyl, 2-methyl-3-ethylindenyl complexes:
(n-butylamido)dimethyl($\eta^5$-2-methyl-3-ethylindenyl)-silanetitanium (II) 1,4-diphenyl-1,3-butadiene,
(n-butylamido)dimethyl($\eta^5$-2-methyl-3-ethylindenyl) silanetitanium (II) 1,3-pentadiene,
(n-butylamido)dimethyl($\eta^5$-2-methyl-3-ethylindenyl)-silanetitanium (III) 2-(N,N-dimethylamino)benzyl,
(n-butylamido)dimethyl($\eta^5$-2-methyl-3-ethylindenyl) silanetitanium (IV) dimethyl,
(n-butylamido)dimethyl($\eta^5$-2-methyl-3-ethylindenyl) silanetitanium (IV) dibenzyl,
(cyclohexylamido)dimethyl($\eta^5$-2-methyl-3-ethylindenyl) silanetitanium (II) 1,4-diphenyl-1,3-butadiene,
(cyclohexylamido)dimethyl($\eta^5$-2-methyl-3-ethylindenyl) silanetitanium (II) 1,3-pentadiene,
(cyclohexylamido)dimethyl($\eta^5$-2-methyl-3-ethylindenyl) silanetitanium (III) 2-(N,N-dimethylamino)benzyl,
(cyclohexylamido)dimethyl($\eta^5$-2-methyl-3-ethylindenyl) silanetitanium (IV) dimethyl,
(cyclohexylamido)dimethyl($\eta^5$-2-methyl-3-ethylindenyl) silanetitanium (IV) dibenzyl,
(isopropylamido)dimethyl($\eta^5$-2-methyl-3-ethylindenyl) silanetitanium (II) 1,4-diphenyl-1,3-butadiene,
(isopropylamido)dimethyl($\eta^5$-2-methyl-3-ethylindenyl) silanetitanium (II) 1,3-pentadiene,
(isopropylamido)dimethyl($\eta^5$-2-methyl-3-ethylindenyl) silanetitanium (III) 2-(N,N-dimethylamino)benzyl,
(isopropylamido)dimethyl($\eta^5$-2-methyl-3-ethylindenyl) silanetitanium (IV) dimethyl,
(isopropylamido)dimethyl($\eta^5$-2-methyl-3-ethylindenyl) silanetitanium (IV) dibenzyl,
(cyclopentylamido)dimethyl($\eta^5$-2-methyl-3-ethylindenyl)silanetitanium (II) 1,4-diphenyl-1,3-butadiene,
(cyclopentylamido)dimethyl($\eta^5$-2-methyl-3-ethylindenyl)silanetitanium (II) 1,3-pentadiene,
(cyclopentylamido)dimethyl($\eta^5$-2-methyl-3-ethylindenyl)silanetitanium (III) 2-(N,N-dimethylamino)benzyl,
(cyclopentylamido)dimethyl($\eta^5$-2-methyl-3-ethylindenyl)silanetitanium (IV) dimethyl,
(cyclopentylamido)dimethyl($\eta^5$-2-methyl-3-ethylindenyl)silanetitanium (IV) dibenzyl,
(cyclododecylamido)dimethyl($\eta^5$-2-methyl-3-ethylindenyl)silanetitanium (II) 1,4-diphenyl-1,3-butadiene,
(cyclododecylamido)dimethyl($\eta^5$-2-methyl-3-ethylindenyl)silanetitanium (II) 1,3-pentadiene,
(cyclododecylamido)dimethyl($\eta^5$-2-methyl-3-ethylindenyl)silanetitanium (III) 2-(N,N-dimethylamino)benzyl,
(cyclododecylamido)dimethyl($\eta^5$-2-methyl-3-ethylindenyl)silanetitanium (IV) dimethyl,
(cyclododecylamido)dimethyl($\eta^5$-2-methyl-3-ethylindenyl)silanetitanium (IV) dibenzyl,
(isobutylamido)dimethyl($\eta^5$-2-methyl-3-ethylindenyl) silanetitanium (II) 1,4-diphenyl-1,3-butadiene,
(isobutylamido)dimethyl($\eta^5$-2-methyl-3-ethylindenyl) silanetitanium (II) 1,3-pentadiene,
(isobutylamido)dimethyl($\eta^5$-2-methyl-3-ethylindenyl) silanetitanium (III) 2-(N,N-dimethylamino)benzyl,
(isobutylamido)dimethyl($\eta^5$-2-methyl-3-ethylindenyl) silanetitanium (IV) dimethyl,
(isobutylamido)dimethyl($\eta^5$-2-methyl-3-ethylindenyl) silanetitanium (IV) dibenzyl,
(n-butylamido)diisopropoxy($\eta^5$-2-methyl-3-ethylindenyl)silanetitanium (II) 1,4-diphenyl-1,3-butadiene,
(n-butylamido)diisopropoxy($\eta^5$-2-methyl-3-ethylindenyl)silanetitanium (II) 1,3-pentadiene,
(n-butylamido)diisopropoxy($\eta^5$-2-methyl-3-ethylindenyl)silanetitanium (III) 2-(N,N-dimethylamino)benzyl,
(n-butylamido)diisopropoxy($\eta^5$-2-methyl-3-ethylindenyl)silanetitanium (IV) dimethyl,
(n-butylamido)diisopropoxy($\eta^5$-2-methyl-3-ethylindenyl)silanetitanium (IV) dibenzyl,
(cyclododecylamido)diisopropoxy($\eta^5$-2-methyl-3-ethylindenyl)silanetitanium (II) 1,4-diphenyl-1,3-butadiene,
(cyclododecylamido)diisopropoxy($\eta^5$-2-methyl-3-ethylindenyl)-silanetitanium (II) 1,3-pentadiene,
(cyclododecylamido)diisopropoxy($\eta^5$-2-methyl-3-ethylindenyl)-silanefitanium (III) 2-(N,N-dimethylamino)benzyl, (cyclododecylamido)diisopropoxy($\eta^5$-2-methyl-3-ethylindenyl)-silanetitanium (IV) dimethyl,
(cyclododecylamido)diisopropoxy($\eta^5$-2-methyl-3-ethylindenyl)-silanetitanium (IV) dibenzyl,
(n-butylamido)dimethoxy($\eta^5$-2-methyl-3-ethylindenyl) silanetitanium (II) 1,4-diphenyl-1,3-butadiene,
(n-butylamido)dimethoxy($\eta^5$-2-methyl-3-ethylindenyl) silanetitanium (II) 1,3-pentadiene,
(n-butylamido)dimethoxy($\eta^5$-2-methyl-3-ethylindenyl) silanetitanium (III) 2-(N,N-dimethylamino)benzyl,
(n-butylamido)dimethoxy($\eta^5$-2-methyl-3-ethylindenyl) silanetitanium (IV) dimethyl,
(n-butylamido)dimethoxy($\eta^5$-2-methyl-3-ethylindenyl) silanetitanium (IV) dibenzyl,
(cyclododecylamido)dimethoxy($\eta^5$-2-methyl-3-ethyl-indenyl)silanetitanium (II) 1,4-diphenyl-1,3-butadiene,
(cyclododecylamido)dimethoxy($\eta^5$-2-methyl-3-ethylindenyl)silanetitanium (II) 1,3-pentadiene,
(cyclododecylamido)dimethoxy($\eta^5$-2-methyl-3-ethylindenyl)silanetitanium (III) 2-(N,N-dimethylamino)benzyl,
(cyclododecylamido)dimethoxy($\eta^5$-2-methyl-3-ethylindenyl)silanetitanium (IV) dimethyl,
(cyclododecylamido)dimethoxy($\eta^5$-2-methyl-3-ethylindenyl)silanetitanium (IV) dibenzyl,
(n-butylamido)ethoxymethyl($\eta^5$-2-methyl-3-ethyl-indenyl)silanetitanium (II) 1,4-diphenyl-1,3-butadiene,
(n-butylamido)ethoxymethyl($\eta^5$-2-methyl-3-ethylindenyl)silanetitanium (II) 1,3-pentadiene,
(n-butylamido)ethoxymethyl($\eta^5$-2-methyl-3-ethylindenyl)silanetitanium (III) 2-(N,N-dimethylamino)benzyl,
(n-butylamido)ethoxymethyl($\eta^5$-2-methyl-3-ethylindenyl)silanetitanium (IV) dimethyl,
(n-butylamido)ethoxymethyl($\eta^5$-2-methyl-3-ethylindenyl)silanetitanium (IV) dibenzyl,
(cyclododecylamido)ethoxymethyl($\eta^5$-2-methyl-3-ethyl-indenyl)silane-titanium (II) 1,4-diphenyl-1,3-butadiene,
(cyclododecylamido)ethoxymethyl($\eta^5$-2-methyl-3-ethylindenyl)silane-titanium (II) 1,3-pentadiene,
(cyclododecylamido)ethoxymethyl($\eta^5$-2-methyl-3-ethylindenyl)silane-titanium (III) 2-(N,N-dimethylamino)benzyl,
(cyclododecylamido)ethoxymethyl($\eta^5$-2-methyl-3-ethylindenyl)silanetitanium (IV) dimethyl,
(cyclododecylamido)ethoxymethyl($\eta^5$-2-methyl-3-ethylindenyl)silanetitanium (IV) dibenzyl, 2,3,4,6-tetramethylindenyl complexes:

(n-butylamido)dimethyl($\eta^5$-2,3,4,6-tetramethylindenyl) silanetitanium (II) 1,4-diphenyl-1,3-butadiene,
(n-butylamido)dimethyl($\eta^5$-2,3,4,6-tetramethylindenyl) silanetitanium (II) 1,3-pentadiene,
(n-butylamido)dimethyl($\eta^5$-2,3,4,6-tetramethylindenyl)-silanetitanium (III) 2-(N,N-dimethylamino)benzyl,
(n-butylamido)dimethyl($\eta^5$-2,3,4,6-tetramethylindenyl) silanetitanium (IV) dimethyl,
(n-butylamido)dimethyl($\eta^5$-2,3,4,6-tetramethylindenyl) silanetitanium (IV) dibenzyl,
(cyclohexylamido)dimethyl($\eta^5$-2,3,4,6-tetramethylindenyl)silanetitanium (II) 1,4-diphenyl-1,3-butadiene,
(cyclohexylamido)dimethyl($\eta^5$-2,3,4,6-tetramethylindenyl)silanetitanium (II) 1,3-pentadiene,
(cyclohexylamido)dimethyl($\eta^5$-2,3,4,6-tetramethylindenyl)silanetitanium (III) 2-(N,N-dimethylamino)benzyl,
(cyclohexylamido)dimethyl($\eta^5$-2,3,4,6-tetramethylindenyl)silanetitanium (IV) dimethyl,
(cyclohexylamido)dimethyl($\eta^5$-2,3,4,6-tetramethylindenyl)silanetitanium (IV) dibenzyl,
(isopropylamido)dimethyl($\eta^5$-2,3,4,6-tetramethylindenyl)silanetitanium (II) 1,4-diphenyl-1,3-butadiene,
(isopropylamido)dimethyl($\eta^5$-2,3,4,6-tetramethylindenyl)silanetitanium (II) 1,3-pentadiene,
(isopropylamido)dimethyl($\eta^5$-2,3,4,6-tetramethylindenyl)silanetitanium (III) 2-(N,N-dimethylamino)benzyl,
(isopropylamido)dimethyl($\eta^5$-2,3,4,6-tetramethylindenyl)silanetitanium (IV) dimethyl,
(isopropylamido)dimethyl($\eta^5$-2,3,4,6-tetramethylindenyl)silanetitanium (IV) dibenzyl,
(cyclopentylamido)dimethy($\eta^5$-2,3,4,6-tetramethylindenyl)silanetitanium (II) 1,4-diphenyl-1,3-butadiene,
(cyclopentylamido)dimethyl($\eta^5$-2,3,4,6-tetramethylindenyl)silanetitanium (II) 1,3-pentadiene,
(cyclopentylamido)dimethyl($\eta^5$-2,3,4,6-tetramethylindenyl)silanetitanium (III) 2-(N,N-dimethylamino)benzyl,
(cyclopentylamido)dimethyl($\eta^5$-2,3,4,6-tetramethylindenyl)silanetitanium (IV) dimethyl,
(cyclopentylamido)dimethyl($\eta^5$-2,3,4,6-tetramethylindenyl)silanetitanium (IV) dibenzyl,
(cyclododecylamido)dimethyl($\eta^5$-2,3,4,6-tetramethylindenyl)silanetitanium (II) 1,4-diphenyl-1,3-butadiene,
(cyclododecylamido)dimethyl($\eta^5$-2,3,4,6-tetramethylindenyl)silanetitanium (II) 1,3-pentadiene,
(cyclododecylamido)dimethyl($\eta^5$-2,3,4,6-tetramethylindenyl)silanetitanium (III) 2-(N,N-dimethylamino)benzyl,
(cyclododecylamido)dimethyl($\eta^5$-2,3,4,6-tetramethylindenyl)silanetitanium (IV) dimethyl,
(cyclododecylamido)dimethyl($\eta^5$-2,3,4,6-tetramethylindenyl)silanetitanium (IV) dibenzyl,
(isobutylamido)dimethyl($\eta^5$-2,3,4,6-tetramethylindenyl) silanetitanium (II) 1,4-diphenyl-1,3-butadiene,
(isobutylamido)dimethyl($\eta^5$-2,3,4,6-tetramethylindenyl) silanetitanium (II) 1,3-pentadiene,
(isobutylamido)dimethyl($\eta^5$-2,3,4,6-tetramethylindenyl) silanetitanium (III) 2-(N,N-dimethylamino)benzyl,
(isobutylamido)dimethyl($\eta^5$-2,3,4,6-tetramethylindenyl) silanetitanium (IV) dimethyl,
(isobutylamido)dimethyl($\eta^5$-2,3,4,6-tetramethylindenyl) silanetitanium (IV) dibenzyl,
(n-butylamido)diisopropoxy($\eta^5$-2,3,4,6-tetramethylindenyl)silane-titanium (II) 1,4-diphenyl-1,3-butadiene,
(n-butylamido)diisopropoxy($\eta^5$-2,3,4,6-tetramethylindenyl)silane-titanium (II) 1,3-pentadiene,
(n-butylamido)diisopropoxy($\eta^5$-2,3,4,6-tetramethylindenyl)-silanetitanium (III) 2-(N,N-dimethylamino)benzyl, (n-butylamido)diisopropoxy($\eta^5$-2,3,4,6-tetramethylindenyl)silane-titanium (IV) dimethyl,
(n-butylamido)diisopropoxy($\eta^5$-2,3,4,6-tetramethylindenyl)silane-titanium (IV) dibenzyl,
(cyclododecylamido)diisopropoxy($\eta^5$-2,3,4,6-tetramethylindenyl)-silanetitanium (II) 1,4-diphenyl-1,3-butadiene,
(cyclododecylamido)diisopropoxy($\eta^5$-2,3,4,6-tetramethylindenyl)silanetitanium (II) 1,3-pentadiene,
(cyclododecylamido)diisopropoxy($\eta^5$-2,3,4,6-tetramethylindenyl)silanetitanium (III) 2-(N,N-dimethylamino)benzyl,
(cyclododecylamido)diisopropoxy($\eta^5$-2,3,4,6-tetramethylindenyl)silanetitanium (IV) dimethyl,
(cyclododecylamido)diisopropoxy($\eta^5$-2,3,4,6-tetramethylindenyl)silanetitanium (IV) dibenzyl,
(n-butylamido)dimethoxy($\eta^5$-2,3,4,6-tetramethylindenyl)silanetitanium (II) 1,4-diphenyl-1,3-butadiene,
(n-butylamido)dimethoxy($\eta^5$-2,3,4,6-tetramethylindenyl)silanetitanium (II) 1,3-pentadiene,
(n-butylamido)dimethoxy($\eta^5$-2,3,4,6-tetramethylindenyl)silanetitanium (III) 2-(N,N-dimethylamino)benzyl,
(n-butylamido)dimethoxy($\eta^5$-2,3,4,6-tetramethylindenyl)silanetitanium (IV) dimethyl,
(n-butylamido)dimethoxy($\eta^5$-2,3,4,6-tetramethylindenyl)silanetitanium (IV) dibenzyl,
(cyclododecylamido)dimethoxy($\eta^5$-2,3,4,6-tetramethylindenyl)silanetitanium (II) 1,4-diphenyl-1,3-butadiene,
(cyclododecylamido)dimethoxy($\eta^5$-2,3,4,6-tetramethylindenyl)silanetitanium (II) 1,3-pentadiene,
(cyclododecylamido)dimethoxy($\eta^5$-2,3,4,6-tetramethylindenyl)silanetitanium (III) 2-(N,N-dimethylamino)benzyl,
(cyclododecylamido)dimethoxy($\eta^5$-2,3,4,6-tetramethylindenyl)silanetitanium (IV) dimethyl,
(cyclododecylamido)dimethoxy($\eta^5$-2,3,4,6-tetramethylindenyl)silanetitanium (IV) dibenzyl,
(n-butylamido)ethoxymethyl($\eta^5$-2,3,4,6-tetramethylindenyl)silanetitanium (II) 1,4-diphenyl-1,3-butadiene,
(n-butylamido)ethoxymethyl($\eta^5$-2,3,4,6-tetramethylindenyl)silanetitanium (II) 1,3-pentadiene,
(n-butylamido)ethoxymethyl($\eta^5$-2,3,4,6-tetramethylindenyl)silanetitanium (III) 2-(N,N-dimethylamino)benzyl,
(n-butylamido)ethoxymethyl($\eta^5$-2,3,4,6-tetramethylindenyl)silanetitanium (IV) dimethyl,
(n-butylamido)ethoxymethyl($\eta^5$-2,3,4,6-tetramethylindenyl)silanetitanium (IV) dibenzyl,
(cyclododecylamido)ethoxymethyl($\eta^5$-2,3,4,6-tetramethylindenyl)silanetitanium (II) 1,4-diphenyl-1,3-butadiene,
(cyclododecylamido)ethoxymethyl($\eta^5$-2,3,4,6-tetramethylindenyl)silanetitanium (II) 1,3-pentadiene,
(cyclododecylamido)ethoxymethyl($\eta^5$-2,3,4,6-tetramethylindenyl)silanetitanium (III) 2-(N,N-dimethylamino)benzyl,
(cyclododecylamido)ethoxymethyl($\eta^5$-2,3,4,6-tetramethylindenyl)silanetitanium (IV) dimethyl,
(cyclododecylamido)ethoxymethyl($\eta^5$-2,3,4,6-tetramethylindenyl)silanetitanium (IV) dibenzyl, 2,3,4,6,7-pentamethylindenyl complexes:
(n-butylamido)dimethyl($\eta^5$-2,3,4,6,7-pentamethylindenyl)silanetitanium (II) 1,4-diphenyl-1,3-butadiene,
(n-butylamido)dimethyl($\eta^5$-2,3,4,6,7-pentamethylindenyl)silanetitanium (II) 1,3-pentadiene,
(n-butylamido)dimethyl($\eta^5$-2,3,4,6,7-pentamethylindenyl)-silanetitanium (III) 2-(N,N-dimethylamino)benzyl,
(n-butylamido)dimethyl($\eta^5$-2,3,4,6,7-pentamethylindenyl)silanetitanium (IV) dimethyl,
(n-butylamido)dimethyl($\eta^5$-2,3,4,6,7-pentamethylindenyl)silanetitanium (IV) dibenzyl,
(cyclohexylamido)dimethyl($\eta^5$-2,3,4,6,7-pentamethylindenyl)silanetitanium (II) 1,4-diphenyl-1,3-butadiene,
(cyclohexylamido)dimethyl($\eta^5$-2,3,4,6,7-pentamethylindenyl)silanetitanium (II) 1,3-pentadiene,
(cyclohexylamido)dimethyl($\eta^5$-2,3,4,6,7-pentamethylindenyl)silanetitanium (III) 2-(N,N-dimethylamino)benzyl,
(cyclohexylamido)dimethyl($\eta^5$-2,3,4,6,7-pentamethylindenyl)silanetitanium (IV) dimethyl,
(cyclohexylamido)dimethyl($\eta^5$-2,3,4,6,7-pentamethylindenyl)silanetitanium (IV) dibenzyl,
(isopropylamido)dimethyl($\eta^5$-2,3,4,6,7-pentamethylindenyl)silanetitanium (II) 1,4-diphenyl-1,3-butadiene,
(isopropylamido)dimethyl($\eta^5$-2,3,4,6,7-pentamethylindenyl)silanetitanium (II) 1,3-pentadiene,
(isopropylamido)dimethyl($\eta^5$-2,3,4,6,7-pentamethylindenyl)silanetitanium (III) 2-(N,N-dimethylamino)benzyl,
(isopropylamido)dimethyl($\eta^5$-2,3,4,6,7-pentamethylindenyl)silanetitanium (IV) dimethyl,
(isopropylamido)dimethyl($\eta^5$-2,3,4,6,7-pentamethylindenyl)silanetitanium (IV) dibenzyl,
(cyclopentylamido)dimethyl($\eta^5$-2,3,4,6,7-pentamethylindenyl)silanetitanium (II) 1,4-diphenyl-1,3-butadiene,
(cyclopentylamido)dimethyl($\eta^5$-2,3,4,6,7-pentamethylindenyl)silanetitanium (II) 1,3-pentadiene,
(cyclopentylamido)dimethyl($\eta^5$-2,3,4,6,7-pentamethylindenyl)silanetitanium (III) 2-(N,N-dimethylamino)benzyl,
(cyclopentylamido)dimethyl($\eta^5$-2,3,4,6,7-pentamethylindenyl)silanetitanium (IV) dimethyl,
(cyclopentylamido)dimethyl($\eta^5$-2,3,4,6,7-pentamethylindenyl)silanetitanium (IV) dibenzyl,
(cyclododecylamido)dimethyl($\eta^5$-2,3,4,6,7-pentamethylindenyl)silanetitanium (II) 1,4-diphenyl-1,3-butadiene,
(cyclododecylamido)dimethyl($\eta^5$-2,3,4,6,7-pentamethylindenyl)silanetitanium (II) 1,3-pentadiene,
(cyclododecylamido)dimethyl($\eta^5$-2,3,4,6,7-pentamethylindenyl)silanetitanium (III) 2-(N,N-dimethylamino)benzyl,
(cyclododecylamido)dimethyl($\eta^5$-2,3,4,6,7-pentamethylindenyl)silanetitanium (IV) dimethyl,
(cyclododecylamido)dimethyl($\eta^5$-2,3,4,6,7-pentamethylindenyl)silanetitanium (IV) dibenzyl,
(isobutylamido)dimethyl($\eta^5$-2,3,4,6,7-pentamethylindenyl)silanetitanium (II) 1,4-diphenyl-1,3-butadiene, (isobutylamido)dimethyl($\eta^5$-2,3,4,6,7-pentamethylindenyl)silanetitanium (II) 1,3-pentadiene,
(isobutylamido)dimethyl($\eta^5$-2,3,4,6,7-pentamethylindenyl)silanetitanium (III) 2-(N,N-dimethylamino)benzyl,
(isobutylamido)dimethyl($\eta^5$-2,3,4,6,7-pentamethylindenyl)silanetitanium (IV) dimethyl,
(isobutylamido)dimethyl($\eta^5$-2,3,4,6,7-pentamethylindenyl)silanetitanium (IV) dibenzyl,
(n-butylamido)diisopropoxy($\eta^5$-2,3,4,6,7-pentamethyl-indenyl)silane-titanium (II) 1,4-diphenyl-1,3-butadiene,
(n-butylamido)diisopropoxy($\eta^5$-2,3,4,6,7-pentamethylindenyl)silane-titanium (II) 1,3-pentadiene,
(n-butylamido)diisopropoxy($\eta^5$-2,3,4,6,7-pentamethylindenyl)-silanetitanium (III) 2-(N,N-dimethylamino)benzyl,
(n-butylamido)diisopropoxy($\eta^5$-2,3,4,6,7-pentamethylindenyl)silane-titanium (IV) dimethyl,
(n-butylamido)diisopropoxy($\eta^5$-2,3,4,6,7-pentamethylindenyl)silane-titanium (IV) dibenzyl,
(cyclododecylamido)diisopropoxy($\eta^5$-2,3,4,6,7-pentamethyl-indenyl)-silanetitanium (II) 1,4-diphenyl-1,3-butadiene,
(cyclododecylamido)diisopropoxy($\eta^5$-2,3,4,6,7-pentamethylindenyl)silanetitanium (II) 1,3-pentadiene,
(cyclododecylamido)diisopropoxy($\eta^5$-2,3,4,6,7-pentamethylindenyl)silanetitanium (III) 2-(N,N-dimethylamino)benzyl,
(cyclododecylamido)diisopropoxy($\eta^5$-2,3,4,6,7-pentamethylindenyl)silanetitanium (IV) dimethyl,
(cyclododecylamido)diisopropoxy($\eta^5$-2,3,4,6,7-pentamethylindenyl)silanetitanium (IV) dibenzyl,
(n-butylamido)dimethoxy($\eta^5$-2,3,4,6,7-pentamethylindenyl)silanetitanium (II) 1,4-diphenyl-1,3-butadiene,
(n-butylamido)dimethoxy($\eta^5$-2,3,4,6,7-pentamethylindenyl)silanetitanium (II) 1,3-pentadiene,
(n-butylamido)dimethoxy($\eta^5$-2,3,4,6,7-pentamethylindenyl)silanetitanium (III) 2-(N,N-dimethylamino)benzyl,
(n-butylamido)dimethoxy($\eta^5$-2,3,4,6,7-pentamethylindenyl)silanetitanium (IV) dimethyl,
(n-butylamido)dimethoxy($\eta^5$-2,3,4,6,7-pentamethylindenyl)silanetitanium (IV) dibenzyl,
(cyclododecylamido)dimethoxy($\eta^5$-2,3,4,6,7-pentamethylindenyl)silanetitanium (II) 1,4-diphenyl-1,3-butadiene,
(cyclododecylamido)dimethoxy($\eta^5$-2,3,4,6,7-pentamethylindenyl)silanetitanium (II) 1,3-pentadiene,
(cyclododecylamido)dimethoxy($\eta^5$-2,3,4,6,7-pentamethylindenyl)silanetitanium (III) 2-(N,N-dimethylamino)benzyl,
(cyclododecylamido)dimethoxy($\eta^5$-2,3,4,6,7-pentamethylindenyl)silanetitanium (IV) dimethyl,
(cyclododecylamido)dimethoxy($\eta^5$-2,3,4,6,7-pentamethylindenyl)silanetitanium (IV) dibenzyl,
(n-butylamido)ethoxymethyl($\eta^5$-2,3,4,6,7-pentamethyl-indenyl)silanetitanium (II) 1,4-diphenyl-1,3-butadiene,
(n-butylamido)ethoxymethyl($\eta^5$-2,3,4,6,7-pentamethylindenyl)silanetitanium (III) 2-(N,N-dimethylamino)benzyl,
(n-butylamido)ethoxymethyl($\eta^5$-2,3,4,6,7-pentamethylindenyl)silanetitanium (IV) dimethyl,
(n-butylamido)ethoxymethyl($\eta^5$-2,3,4,6,7-pentamethylindenyl)silanetitanium (IV) dibenzyl,
(cyclododecylamido)ethoxymethyl($\eta^5$-2,3,4,6,7-pentamethylindenyl)silanetitanium (II) 1,4-diphenyl-1,3-butadiene,
(cyclododecylamido)ethoxymethyl($\eta^5$-2,3,4,6,7-pentamethylindenyl)silanetitanium (II) 1,3-pentadiene,
(cyclododecylamido)ethoxymethyl($\eta^5$-2,3,4,6,7-pentamethylindenyl)silanetitanium (III) 2-(N,N-dimethylamino)benzyl,
(cyclododecylamido)ethoxymethyl($\eta^5$-2,3,4,6,7-pentamethylindenyl)silanetitanium (IV) dimethyl,
(cyclododecylamido)ethoxymethyl($\eta^5$-2,3,4,6,7-pentamethylindenyl)silanetitanium (IV) dibenzyl, 3-phenyl-s-indacen-1-yl complexes (alternatively referred to as [1,2,3,4,5-$\eta$]-1,5,6,7-tetrahydro-3-phenyl-s-indacen-1-yl]complexes)
(i-propylamido)dimethyl($\eta^5$-3-phenyl-s-indacenyl)silanetitanium (IV) dimethyl,
(cyclohexylamido)dimethyl($\eta^5$-3-phenyl-s-indacenyl)silanetitanium (IV) dimethyl,
(n-butylamido)dimethyl($\eta^5$-3-phenyl-s-indacenyl)silanetitanium (II) 1,4-diphenyl-1,3-butadiene,
(n-butylamido)dimethyl($\eta^5$-3-phenyl-s-indacenyl)silanetitanium (II) 1,3-pentadiene,
(n-butylamido)dimethyl($\eta^5$-3-phenyl-s-indacenyl)silanetitanium (III) 2-(N,N-dimethylamino)benzyl,
(n-butylamido)dimethyl($\eta^5$-3-phenyl-s-indacenyl)silanetitanium (IV) dimethyl,
(n-butylamido)dimethyl($\eta^5$-3-phenyl-s-indacenyl)silanetitanium (IV) dibenzyl,
(cyclododecylamido)dimethyl($\eta^5$-3-phenyl-s-indacenyl)silanetitanium (II) 1,4-diphenyl-1,3-butadiene,
(cyclododecylamido)dimethyl($\eta^5$-3-phenyl-s-indacenyl)silanetitanium (II) 1,3-pentadiene,
(cyclododecylamido)dimethyl($\eta^5$-3-phenyl-s-indacenyl)silanetitanium (III) 2-(N,N-dimethylamino)benzyl,
(cyclododecylamido)dimethyl($\eta^5$-3-phenyl-s-indacenyl)silanetitanium (IV) dimethyl,
(cyclododecylamido)dimethyl($\eta^5$-3-phenyl-s-indacenyl)silanetitanium (IV) dibenzyl, 3-naphthyl-s-indacenyl complexes:
(i-propylamido)dimethyl($\eta^5$-3-naphthyl-s-indacenyl)silanettanium (IV) dimethyl
(cyciohexylamido)dimethyl($\eta^5$-3-naphthyl-s-indacenyl)silanetitanium (IV) dimethyl 3-biphenyl-s-indacenyl complexes:
(i-propylamido)dimethyl($\eta^5$-3-biphenyl-s-indacenyl)silanetitanium (IV) dimethyl, and
(cyclohexylamido)dimethyl($\eta^5$-3-biphenyl-s-indacenyl)silanetitanium (IV) dimethyl 2-methyl-3-biphenyl-s-indacenyl complexes:
(i-propylamido)dimethyl($\eta^5$-2-methyl-3-biphenyl-s-indacenyl)silane-titanium (IV) dimethyl, and
(cyclohexylamido)dimethyl($\eta^5$-2-methyl-3-biphenyl-s-indacenyl)silane-titanium (IV) dimethyl 2-methyl-3-naphthyl-s-indacenyl complexes:
(cyclohexylamido)dimethyl($\eta^5$-2-methyl-3-naphthyl-s-indacenyl)silanetitanium (II) 1,4-diphenyl-1,3-butadiene, (cyclohexylamido)dimethyl($\eta^5$-2-methyl-3-naphthyl-s-indacenyl)silanetitanium (II) 1,3-pentadiene,
(cyclohexylamido)dimethyl($\eta^5$-2-methyl-3-naphthyl-s-indacenyl)silanetitanium (III) 2-(N,N-dimethylamino)benzyl,
(cyclohexylamido)dimethyl($\eta^5$-2-methyl-3-naphthyl-s-indacenyl)silanetitanium (IV) dimethyl, and
(cyclohexylamido)dimethyl($\eta^5$-2-methyl-3-naphthyl-s-indacenyl)silanetitanium (IV) dibenzyl.

3-phenyl-gem-dimethylacenaphthalenyl complexes (also referred to as (1,2,3,4,5-$\eta$)(5,6,7,8-tetrahydro-5,5,8,8-tetramethyl-1H-Benz(f)inde-1-yl) complexes)

(n-butylamido)dimethyl($\eta^5$-3-phenyl-gem-dimethylacenaphth-alenyl)silanetitanium (II) 1,4-diphenyl-1,3-butadiene,
(n-butylamido)dimethyl($\eta^5$-3-phenyl-gem-dimethylacenaphth-alenyl)silanetitanium (II) 1,3-pentadiene,
(n-butylamido)dimethyl($\eta^5$-3-phenyl-gem-dimethylacenaphth-alenyl)silanetitanium (III) 2-(N,N-dimethylamino)benzyl,
(n-butylamido)dimethyl($\eta^5$-3-phenyl-gem-dimethylacenaphth-alenyl)silanetitanium (IV) dimethyl,
(n-butylamido)dimethyl($\eta^5$-3-phenyl-gem-dimethylacenaphth-alenyl)silanetitanium (IV) dibenzyl,
(cyclododecylamido)dimethyl($\eta^5$-3-phenyl-gem-dimethylacenaphth-alenyl)silanetitanium (II) 1,4-diphenyl-1,3-butadiene,
(cyclododecylamido)dimethyl($\eta^5$-3-phenyl-gem-dimethylacenaphth-alenyl)silanetitanium (II) 1,3-pentadiene,
(cyclododecylamido)dimethyl($\eta^5$-3-gem-dimethylacenaphth-alenyl)silanetitanium (III) 2-(N,N-dimethylamino)benzyl,
(cyclododecylamido)dimethyl($\eta^5$-3-phenyl-gem-dimethylacenaphth-alenyl)silanetitanium (IV) dimethyl,
(cyclododecylamido)dimethyl($\eta^5$-3-phenyl-gem-dimethylacenaphth-alenyl)silanetitanium (IV) dibenzyl, 2-methyl-s-indacen-1-yl complexes:
(n-butylamido)dimethyl($\eta^5$-2-methyl-s-indacen-1-yl)silanetitanium (II) 1,4-diphenyl-1,3-butadiene,
(n-butylamido)dimethyl($\eta^5$-2-methyl-s-indacen-1-yl)silanetitanium (II) 1,3-pentadiene,
(n-butylamido)dimethyl($\eta^5$-2-methyl-s-indacen-1-yl)silanetitanium (III) 2-(N,N-dimethylamino)benzyl,
(n-butylamido)dimethyl($\eta^5$-2-methyl-s-indacen-1-yl)silanetitanium (IV) dimethyl,
(n-butylamido)dimethyl($\eta^5$-2-methyl-s-indacen-1-yl)silanetitanium (IV) dibenzyl,
(cyclohexylamido)dimethyl($\eta^5$-2-methyl-s-indacen-1-yl)silanetitanium (II) 1,4-diphenyl-1,3-butadiene,
(cyclohexylamido)dimethyl($\eta^5$-2-methyl-s-indacen-1-yl)silanetitanium (II) 1,3-pentadiene,
(cyclohexylamido)dimethyl($\eta^5$-2-methyl-s-indacen-1-yl)silanetitanium (III) 2-(N,N-dimethylamino)benzyl,
(cyclohexylamido)dimethyl($\eta^5$-2-methyl-s-indacen-1-yl)silanetitanium (IV) dimethyl,
(cyclohexylamido)dimethyl($\eta^5$-2-methyl-s-indacen-1-yl)silanetitanium (IV) dibenzyl,
(isopropylamido)dimethyl($\eta^5$-2-methyl-s-indacen-1-yl)silanetitanium (II) 1,4-diphenyl-1,3-butadiene,
(isopropylamido)dimethyl($\eta^5$-2-methyl-s-indacen-1-yl)silanetitanium (II) 1,3-pentadiene,
(isopropylamido)dimethyl($\eta^5$-2-methyl-s-indacen-1-yl)silanetitanium (III) 2-(N,N-dimethylamino)benzyl,
(isopropylamido)dimethyl($\eta^5$-2-methyl-s-indacen-1-yl)silanetitanium (IV) dimethyl,
(isopropylamido)dimethyl($\eta^5$-2-methyl-s-indacen-1-yl)silanetitanium (IV) dibenzyl,
(cyclopentylamido)dimethyl($\eta^5$-2-methyl-s-indacen-1-yl)silanetitanium (II) 1,4-diphenyl-1,3-butadiene,
(cyclopentylamido)dimethyl($\eta^5$-2-methyl-s-indacen-1-yl)silanetitanium (II) 1,3-pentadiene,
(cyclopentylamido)dimethyl($\eta^5$-2-methyl-s-indacen-1-yl)silanetitanium (III) 2-(N,N-dimethylamino)benzyl,
(cyclopentylamido)dimethyl($\eta^5$-2-methyl-s-indacen-1-yl)silanetitanium (IV) dimethyl,
(cyclopentylamido)dimethyl($\eta^5$-2-methyl-s-indacen-1-yl)silanetitanium (IV) dibenzyl,
(cyclododecylamido)dimethyl($\eta^5$-2-methyl-s-indacen-1-yl)silanetitanium (II) 1,4-diphenyl-1,3-butadiene,
(cyclododecylamido)dimethyl($\eta^5$-2-methyl-s-indacen-1-yl)silanetitanium (II) 1,3-pentadiene,
(cyclododecylamido)dimethyl($\eta^5$-2-methyl-s-indacen-1-yl)silanetitanium (III) 2-(N,N-dimethylamino)benzyl,
(cyclododecylamido)dimethyl($\eta^5$-2-methyl-s-indacen-1-yl)silanetitanium (IV) dimethyl,
(cyclododecylamido)dimethyl($\eta^5$-2-methyl-s-indacen-1-yl)silanetitanium (IV) dibenzyl,
(isobutylamido)dimethyl($\eta^5$-2-methyl-s-indacen-1-yl)silanetitanium (II) 1,4-diphenyl-1,3-butadiene,
(isobutylamido)dimethyl($\eta^5$-2-methyl-s-indacen-1-yl)silanetitanium (II) 1,3-pentadiene,
(isobutylamido)dimethyl($\eta^5$-2-methyl-s-indacen-1-yl)silanetitanium (III) 2-(N,N-dimethylamino)benzyl,
(isobutylamido)dimethyl($\eta^5$-2-methyl-s-indacen-1-yl)silanetitanium (IV) dimethyl,
(isobutylamido)dimethyl($\eta^5$-2-methyl-s-indacen-1-yl)silanetitanium (IV) dibenzyl, 2,3-dimethyl-s-indacen-1-yl complexes:
(n-butylamido)dimethyl($\eta^5$-2,3-dimethyl-s-indacen-1-yl)silanetitanium (II) 1,4-diphenyl-1,3-butadiene,
(n-butylamido)dimethyl($\eta^5$-2,3-dimethyl-s-indacen-1-yl)silanetitanium (II) 1,3-pentadiene,
(n-butylamido)dimethyl($\eta^5$-2,3-dimethyl-s-indacen-1-yl)silanetitanium (III) 2-(N,N-dimethylamino)benzyl,
(n-butylamido)dimethyl($\eta^5$-2,3-dimethyl-s-indacen-1-yl)silanetitanium (IV) dimethyl,
(n-butylamido)dimethyl($\eta^5$-2,3-dimethyl-s-indacen-1-yl)silanetitanium (IV) dibenzyl,
(cyclohexylamido)dimethyl($\eta^5$-2,3-dimethyl-s-indacen-1-yl)silanetitanium (II) 1,4-diphenyl-1,3-butadiene,
(cyclohexylamido)dimethyl($\eta^5$-2,3-dimethyl-s-indacen-1-yl)silanetitanium (II) 1,3-pentadiene,
(cyclohexylamido)dimethyl($\eta^5$-2,3-dimethyl-s-indacen-1-yl)silanetitanium (III) 2-(N,N-dimethylamino)benzyl,
(cyclohexylamido)dimethyl($\eta^5$-2,3-dimethyl-s-indacen-1-yl)silanetitanium (IV) dimethyl,
(cyclohexylamido)dimethyl($\eta^5$-2,3-dimethyl-s-indacen-1-yl)silanetitanium (IV) dibenzyl, (isopropylamido)dimethyl($\eta^5$-2,3-dimethyl-s-indacen-1-yl)silanetitanium (II) 1,4-diphenyl-1,3-butadiene,
(isopropylamido)dimethyl($\eta^5$-2,3-dimethyl-s-indacen-1-yl)silanetitanium (II) 1,3-pentadiene,
(isopropylamido)dimethyl($\eta^5$-2,3-dimethyl-s-indacen-1-yl)silanetitanium (III) 2-(N,N-dimethylamino)benzyl,
(isopropylamido)dimethyl($\eta^5$-2,3-dimethyl-s-indacen-1-yl)silanetitanium (IV) dimethyl,
(isopropylamido)dimethyl($\eta^5$-2,3-dimethyl-s-indacen-1-yl)silanetitanium (IV) dibenzyl,
(cylopentylamido)dimethyl($\eta^5$-2,3-dimethyl-s-indacen-1-yl)silanetitanium (II) 2,4-diphenyl-1,3-butadiene,
(cyclopentylamido)dimethyl($\eta^5$-2,3-dimethyl-s-indacen-1-yl)silanetitanium (II) 1,3-pentadiene,
(cyclopentylamido)dimethyl($\eta^5$-2,3-dimethyl-s-indacen-1-yl)silanetitanium (III) 2-(N,N-dimethylamino)benzyl,
(cyclopentylamido)dimethyl($\eta^5$-2,3-dimethyl-s-indacen-1-yl)silanetitanium (IV) dimethyl,
(cyclopentylamido)dimethyl($\eta^5$-2,3-dimethyl-s-indacen-1-yl)silanetitanium (IV) dibenzyl,
(cyclododecylamido)dimethyl($\eta^5$-2,3-dimethyl-s-indacen-1-yl)silanetitanium (II) 1,4-diphenyl-1,3-butadiene,
(cyclododecylamido)dimethyl($\eta^5$-2,3-dimethyl-s-indacen-1-yl)silanetitanium (II) 1,3-pentadiene,
(cyclododecylamido)dimethyl($\eta^5$-2,3-dimethyl-s-indacen-1-yl)silanetitanium (III) 2-(N,N-dimethylamino)benzyl,
(cyclododecylamido)dimethyl($\eta^5$-2,3-dimethyl-s-indacen-1-yl)silanetitanium (IV) dimethyl,
(cyclododecylamido)dimethyl($\eta^5$-2,3-dimethyl-s-indacen-1-yl)silanetitanium (IV) dibenzyl,
(isobutylamido)dimethyl($\eta^5$-2,3-dimethyl-s-indacen-1-yl)silanetitanium (II) 1,4-diphenyl-1,3-butadiene,
(isobutylamido)dimethyl($\eta^5$-2,3-dimethyl-s-indacen-1-yl)silanetitanium (II) 1,3-pentadiene,
(isobutylamido)dimethyl($\eta^5$-2,3-dimethyl-s-indacen-1-yl)silanetitanium (III) 2-(N,N-dimethylamino)benzyl,
(isobutylamido)dimethyl($\eta^5$-2,3-dimethyl-s-indacen-1-yl)silanetitanium (IV) dimethyl,
(isobutylamido)dimethyl($\eta^5$-2,3-dimethyl-s-indacen-1-yl)silanetitanium (IV) dibenzyl, 3-methyl-s-indacen-1-yl complexes:

(n-butylamido)dimethyl($\eta^5$-3-methyl-s-indacen-1-yl)silanetitanium (II) 1,4-diphenyl-1,3-butadiene,
(n-butylamido)dimethyl($\eta^5$-3-methyl-s-indacen-1-yl)silanetitanium (II) 1,3-pentadiene,
(n-butylamido)dimethyl($\eta^5$-3-methyl-s-indacen-1-yl)silanetitanium (III) 2-(N,N-dimethylamino)benzyl,
(n-butylamido)dimethyl($\eta^5$-3-methyl-s-indacen-1-yl)silanetitanium (IV) dimethyl,
(n-butylamido)dimethyl($\eta^5$-3-methyl-s-indacen-1-yl)silanetitanium (IV) dibenzyl,
(cyclohexylamido)dimethyl($\eta^5$-3-methyl-s-indacen-1-yl)silanetitanium (II) 1,4-diphenyl-1,3-butadiene,
(cyclohexylamido)dimethyl($\eta^5$-3-methyl-s-indacen-1-yl)silanetitanium (II) 1,3-pentadiene,
(cyclohexylamido)dimethyl($\eta^5$-3-methyl-s-indacen-1-yl)silanetitanium (III) 2-(N,N-dimethylamino)benzyl,
(cyclohexylamido)dimethyl($\eta^5$-3-methyl-s-indacen-1-yl)silanetitanium (IV) dimethyl,
(cyclohexylamido)dimethyl($\eta^5$-3-methyl-s-indacen-1-yl)silanetitanium (IV) dibenzyl,
(isopropylamido)dimethyl($\eta^5$-3-methyl-s-indacen-1-yl)silanetitanium (II) 1,4-diphenyl-1,3-butadiene,
(isopropylamido)dimethyl($\eta^5$-3-methyl-s-indacen-1-yl)silanetitanium (II) 1,3-pentadiene,
(isopropylamido)dimethyl($\eta^5$-3-methyl-s-indacen-1-yl)silanetitanium (III) 2-(N,N-dimethylamino)benzyl,
(isopropylamido)dimethyl($\eta^5$-3-methyl-s-indacen-1-yl)silanetitanium (IV) dimethyl,
(isopropylamido)dimethyl($\eta^5$-3-methyl-s-indacen-1-yl)silanetitanium (IV) dibenzyl,
(cyclopentylamido)dimethyl($\eta^5$-3-methyl-s-indacen-1-yl)silanetitanium (II) 1,4-diphenyl-1,3-butadiene,
(cyclopentylamido)dimethyl($\eta^5$-3-methyl-s-indacen-1-yl)silanetitanium (II) 1,3-pentadiene,
(cyclopentylamido)dimethyl($\eta^5$-3-methyl-s-indacen-1-yl)silanetitanium (III) 2-(N,N-dimethylamino)benzyl,
(cyclopentylamido)dimethyl($\eta^5$-3-methyl-s-indacen-1-yl)silanetitanium (IV) dimethyl,
(cyclopentylamido)dimethyl($\eta^5$-3-methyl-s-indacen-1-yl)silanetitanium (IV) dibenzyl,
(cyclododecylamido)dimethyl($\eta^5$-3-methyl-s-indacen-1-yl)silanetitanium (II) 1,4-diphenyl-1,3-butadiene,
(cyclododecylamido)dimethyl($\eta^5$-3-methyl-s-indacen-1-yl)silanetitanium (II) 1,3-pentadiene,
(cyclododecylamido)dimethyl($\eta^5$-3-methyl-s-indacen-1-yl)silanetitanium (III) 2-(N,N-dimethylamino)benzyl,
(cyclododecylamido)dimethyl($\eta^5$-3-methyl-s-indacen-1-yl)silanetitanium (IV) dimethyl,
(cyclododecylamido)dimethyl($\eta^5$-3-methyl-s-indacen-1-yl)silanetitanium (IV) dibenzyl,
(isobutylamido)dimethyl($\eta^5$-3-methyl-s-indacen-1-yl)silanetitanium (II) 1,4-diphenyl-1,3-butadiene,
(isobutylamido)dimethyl($\eta^5$-3-methyl-s-indacen-1-yl)silanetitanium (II) 1,3-pentadiene,
(isobutylamido)dimethyl($\eta^5$-3-methyl-s-indacen-1-yl)silanetitanium (III) 2-(N,N-dimethylamino)benzyl,
(isobutylamido)dimethyl($\eta^5$-3-methyl-s-indacen-1-yl)silanetitanium (IV) dimethyl, and
(isobutylamido)dimethyl($\eta^5$-3-methyl-s-indacen-1-yl)silanetitanium (IV) dibenzyl.

The complexes can be prepared by use of well known synthetic techniques. Optionally a reducing agent can be employed to produce the lower oxidation state complexes. Such a process is disclosed in U.S. Ser. No. 8/241,523, filed May 13, 1994, published as WO95-00526. The reactions are conducted in a suitable noninterfering solvent at a temperature from −100 to 300° C., preferably from −78 to 100° C., most preferably from 0 to 50° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl) borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. No. 5,153,157, U.S. Pat. No. 5,064,802, EP-A-468,651 (equivalent to U.S. Ser. No. 07/547,718), EP-A-520,732 (equivalent to U.S. Ser. No. 07/876,268), and EP-A-520,732 (equivalent to U.S. Ser. Nos. 07/884,966 filed May 1, 1992), each of which is incorporated herein by reference.

Combinations of neutral Lewis acids, especially the combination of a trialkyl aluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. A benefit according to the present invention is the discovery that the most efficient catalyst activation using such a combination of tris(pentafluorophenyl)borane/ alumoxane mixture occurs at reduced levels of alumoxane. Preferred molar ratios of Group 4 metal complex:tris(pentafluoro-phenylborane:alumoxane are from 1:1:1 to 1:5:5, more preferably from 1:1:1.5 to 1:5:3. The surprising efficient use of lower levels of alumoxane with the present invention allows for the production of olefin polymers with high catalytic efficiencies using less of the expensive alumoxane cocatalyst. Additionally, polymers with lower levels of aluminum residue, and hence greater clarity, are obtained.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or a neutral Lewis base such as an ether or nitrile. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

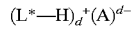

wherein:

L* is a neutral Lewis base;

(L*—H)+ is a Bronsted acid;

$A^{d-}$ is a noncoordinating, compatible anion having a charge of d-, and d is an integer from 1 to 3.

More preferably $A^{d-}$ corresponds to the formula: $[M'Q_4]^-$; wherein:

M' is boron or aluminum in the +3 formal oxidation state; and

Q independently each occurrence is selected from hydride, dialkylamido, halide, hydrocarbyl, hydrocarbyloxide, halosubstituted-hydrocarbyl, halosubstituted hydrocarbyloxy, and halo-substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is $A^-$. Activating cocatalysts comprising boron which are particularly useful in the preparation of catalysts of this invention may be represented by the following general formula:

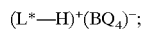

wherein:

L* is as previously defined;

B is boron in a formal oxidation state of 3; and

Q is a hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl.

Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are tri-substituted ammonium salts such as:

trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
 tri(sec-butyl)ammonium tetrakis(pentafluorophenyl)borate,
N,N-dimethylanilinium tetrakis(pentafluorophenyl)borate,
N,N-dimethylanilinium n-butyltris(pentafluorophenyl)borate,
N,N-dimethylanilinium benzyltris(pentafluorophenyl)borate,
N,N-dimethylanilinium tetrakis(4-(t-butyldimethylsilyl)-2,3,5,6-tetrafluorophenyl)borate,
N,N-dimethylanilinium tetrakis(4-(triisopropylsilyl)-2,3,5,6-tetrafluorophenyl)borate,
N,N-dimethylanilinium pentafluorophenoxytris(pentafluorophenyl)borate,
N,N-diethylanilinium tetrakis(pentafluorophenyl)borate,
N,N-dimethyl-2,4,6-trimethylanilinium tetrakis(pentafluorophenyl)borate,
trimethylammonium tetrakis(2,3,4,6-tetrafluorophenyl)borate,
triethylammonium tetrakis(2,3,4,6-tetrafluorophenyl)borate,
tripropylammonium tetrakis(2,3,4,6-tetrafluorophenyl)borate,
tri(n-butyl)ammonium tetrakis(2,3,4,6-tetrafluorophenyl)borate,
dimethyl(t-butyl)ammonium tetrakis(2,3,4,6-tetrafluorophenyl)borate,
N,N-dimethylanilinium tetrakis(2,3,4,6-tetrafluorophenyl)borate,
N,N-diethylanilinium tetrakis(2,3,4,6-tetrafluorophenyl)borate, and
N,N-dimethyl-2,4,6-trimethylanilinium tetrakis(2,3,4,6tetrafluorophenyl)borate;

dialkyl ammonium salts such as:
  di-(i-propyl)ammonium tetrakis(pentafluorophenyl)borate, and
  dicyclohexylammonium tetrakis(pentafluorophenyl)borate;

tri-substituted phosphonium salts such as:
  triphenylphosphonium tetrakis(pentafluorophenyl)borate,
  tri(o-tolyl)phosphonium tetrakis(pentafluorophenyl)borate, and
  tri(2,6-dimethylphenyl)phosphonium tetrakis(pentafluorophenyl)borate;

di-substituted oxonium salts such as:
  diphenyloxonium tetrakis(pentafluorophenyl)borate,
  di(o-tolyl)oxonium tetrakis(pentafluorophenyl)borate, and
  di(2,6-dimethylphenyl)oxonium tetrakis(pentafluorophenyl)borate;

di-substituted sulfonium salts such as:
  diphenylsulfonium tetrakis(pentafluorophenyl)borate,
  di(o-tolyl)sulfonium tetrakis(pentafluorophenyl)borate, and
  bis(2,6-dimethylphenyl)sulfonium tetrakis(pentafluorophenyl)borate.

Preferred $(L^*-H)^+$ cations are N,N-dimethylanilinium and tributylammonium.

Another suitable ion forming, activating cocatalyst comprises a salt of a cationic oxidizing agent and a noncoordinating, compatible anion represented by the formula:

$$(Ox^{e+})_d(A^{d-})_e.$$

wherein:

$Ox^{e+}$ is a cationic oxidizing agent having a charge of e+;

e is an integer from 1 to 3; and $A^{d-}$ and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion and a noncoordinating, compatible anion represented by the formula:

$$\text{\textcircled{c}}^+A^-$$

wherein:

$\text{\textcircled{c}}^+$ is a $C_{1-20}$ carbenium ion; and $A^-$ is as previously defined. A preferred carbenium ion is the trityl cation, that is triphenylmethylium.

A further suitable ion forming, activating cocatalyst comprises a compound which is a salt of a silylium ion and a noncoordinating, compatible anion represented by the formula:

$$R_3Si(X')_q{}^+A^-$$

wherein:

R is $C_{1-10}$ hydrocarbyl, and X', q and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in J. Chem Soc. Chem. Comm., 1993, 383–384, as well as Lambert, J. B., et al., Organometallics, 1994, 13, 2430–2443. The use of the above silylium salts as activating cocatalysts for addition polymerization catalysts is claimed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

Especially preferred cocatalysts will comprise a cation which is a Bronsted acid capable of donating a proton, and an inert, compatible, noncoordinating, anion, characterized by a solubility at 25° C. in hexane, cyclohexane or methylcyclohexane of at least 5 weight percent, preferably at least 7.5 weight percent. By the use of the foregoing catalyst activator, improved catalyst activation is provided. More particularly, increased catalyst efficiency and rate of polymerization are obtained, especially under solution polymerization conditions, most especially continuous, solution polymerization conditions.

Preferred embodiments of such cocatalysts may be represented by the following general formula:

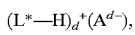

wherein:

L* is a neutral Lewis base;

(L*—H)+ is a Bronsted acid;

$A^{d-}$ is a noncoordinating, compatible anion having charge d-, and d is an integer from 1 to 3.

Examples of suitable anions of the formula $A^{d-}$ include sterically shielded diboron anions corresponding to the formula:

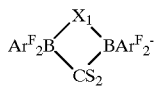

wherein:

S is alkyl, fluoroalkyl, aryl, or fluoroaryl (and where two S groups are present additionally hydrogen), $Ar^F$ is fluoroaryl, and $X^1$ is either hydrogen or halide.

Such diboron anions are disclosed in U.S. Pat. No. 5,447,895, the teachings of which are herein incorporated by reference.

Additional examples of $A^{d-}$ anions are those anions corresponding to the formula:

wherein:

k is an integer from 1 to 3;

n' is an integer from 2 to 6;

n'-k=d;

M' is an element selected from Group 13 of the Periodic Table of the Elements; and Q independently each occurrence is selected from hydride, dialkylamido, halide, alkoxide, aryloxide, hydrocarbyl, and halosubstituted-hydrocarbyl radicals, said Q having up to 20 carbons with the proviso that in not more than one occurrence is Q halide.

In a more preferred embodiment, d is one, that is, the counter ion has a single negative charge and corresponds to the formula, A⁻. Activating cocatalysts comprising boron which are particularly useful in this invention may be represented by the following general formula:

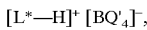

wherein:

L* is a nitrogen, sulfur or phosphorus containing neutral Lewis base;

B is boron in an oxidation state of 3; and

Q' is a fluorinated $C_{1-20}$ hydrocarbyl group.

Most preferably, Q' is in each occurrence a fluorinated aryl group, especially a pentafluorophenyl group.

Generally, solubility of the catalyst activators of the invention in aliphatic compounds is increased by incorporation of one or more oleophilic groups such as long chain alkyl groups; long chain alkenyl groups; or halo-, alkoxy-, amino-, silyl-, or germyl-substituted long chain alkyl groups or long chain alkenyl groups into the Bronsted acid, L. By the term "long chain" are meant groups having from 10 to 50 non-hydrogen atoms in such group, preferably in a non-branched form. Preferably such L groups contain from 1 to 3 $C_{10-40}$ n-alkyl groups with a total of from 12 to 100 carbons, more preferably 2 $C_{10-40}$ alkyl groups and from 21 to 90 total carbons. The presence of such oleophilic groups is believed to render the activator more soluble in aliphatic liquids thereby improving the effectiveness in catalyst activation. It is understood that the catalyst activator may comprise a mixture of oleophilic groups of differing lengths. For example, one suitable activator is the protonated ammonium salt derived from the commercially available long chain amine comprising a mixture of two $C_{14}$, $C_{16}$ or $C_{18}$ alkyl groups and one methyl group. Such amines are available from Witco Corp., under the trade name Kemamine™ T9701, and from Akzo-Nobel under the trade name Armeen™ M2HT. The present cocatalysts may be used in reduced concentrations based on amount of metal complex compared to the amounts of prior known cocatalysts previously required, while retaining equivalent or improved catalyst efficiencies.

Illustrative, but not limiting examples of boron compounds which may be used as ionic activating cocatalysts useful in the preparation of the polymers of this invention are tri-substituted ammonium salts such as:

decyldi(methyl)ammonium tetrakis(pentafluorophenyl) borate, dodecyldi(methyl)ammonium tetrakis (pentafluorophenyl) borate, tetradecyldi(methyl) ammonium tetrakis(pentafluorophenyl) borate, hexaadecyldi(methyl)ammonium tetrakis (pentafluorophenyl) borate, octadecyldi(methyl)ammonium tetrakis (pentafluorophenyl)borate, eicosyldi(methyl) ammonium tetrakis(pentafluorophenyl) borate, methyldi(decyl)ammonium tetrakis (pentafluorophenyl) borate, methyldi(dodecyl) ammonium tetrakis(pentafluorophenyl) borate, methyldi(tetradecyl)ammonium tetrakis (pentafluorophenyl) borate, methyldi(hexadecyl)ammonium tetrakis (pentafluorophenyl) borate, methyldi(octadecyl)ammonium tetrakis (pentafluorophenyl) borate, methyldi(eicosyl) ammonium tetrakis(pentafluorophenyl) borate, tridecylammonium tetrakis(pentafluorophenyl) borate, tridodecylammonium tetrakis(pentafluorophenyl) borate, tritetradecylammonium tetrakis(pentafluorophenyl) borate, trihexadecylammonium tetrakis(pentafluorophenyl) borate, trioctadecylammonium tetrakis(pentafluorophenyl) borate, trieicosylammonium tetrakis(pentafluorophenyl)borate, decyldi(n-butyl)ammonium tetrakis(pentafluorophenyl) borate, dodecyldi(n-butyl)ammonium tetrakis (pentafluorophenyl)borate, octadecyldi(n-butyl)ammonium tetrakis (pentafluorophenyl)borate, N,N-didodecylanilinium tetrakis(pentafluorophenyl)borate, N-methyl-N-dodecylanilinium tetrakis(pentafluorophenyl)borate, N,N-di(octadecyl)(2,4,6-trimethylanilinium)tetrakis(pentafluorophenyl)borate, cyclohexyldi(dodecyl)ammonium tetrakis(pentafluorophenyl)borate, and methyldi(dodecyl)ammonium tetrakis-(2,3,4,6-tetrafluorophenyl)borate.

Suitable similarly substituted sulfonium or phosphonium salts such as, di(decyl)sulfonium tetrakis(pentafluorophenyl)borate, (n-butyl)dodecylsulfonium tetrakis(pentafluorophenyl)borate, tridecylphosphonium tetrakis(pentafluorophenyl)borate, di(octadecyl)methylphosphonium tetrakis(pentafluorophenyl)borate, and tri(tetradecyl)phosphonium tetrakis(pentafluorophenyl)borate, may also be named.

Preferred activators are di(octadecyl)methylammonium tetrakis(pentafluorophenyl)borate and di(octadecyl)(n-butyl)ammonium tetrakis(pentafluorophenyl)borate.

The cocatalysts may also be used in combination with a tri(hydrocarbyl)aluminum compound having from 1 to 10 carbons in each hydrocarbyl group, an oligomeric or polymeric alumoxane compound, a di(hydrocarbyl)(hydrocarbyloxy)aluminum compound having from 1 to 20 carbons in each hydrocarbyl or hydrocarbyloxy group, or a mixture of the foregoing compounds, if desired. These aluminum compounds are usefully employed for their beneficial ability to scavenge impurities such as oxygen, water, and aldehydes from the polymerization mixture.

Suitable di(hydrocarbyl)(hydrocarbyloxy)aluminum compounds correspond to the formula $T^1_2AlOT^2$ wherein $T^1$ is $C_{3-6}$ secondary or tertiary alkyl, most preferably isopropyl, isobutyl or tert-butyl; and $T^2$ is a $C_{12-30}$ alkaryl radical or aralkyl radical, most preferably, 2,6-di(t-butyl)-4-methylphenyl, 2,6-di(t-butyl)-4-methyltolyl, 2,6-di(i-butyl)-4-methylphenyl, or 4-(3',5'-ditertiarybutyltolyl)-2,6-ditertiarybutylphenyl.

Preferred aluminum compounds include $C_{2-6}$ trialkyl aluminum compounds, especially those wherein the alkyl groups are ethyl, propyl, isopropyl, n-butyl, isobutyl, pentyl, neopentyl, or isopentyl, dialkyl(aryloxy)aluminum compounds containing from 1–6 carbons in the alkyl group and from 6 to 18 carbons in the aryl group (especially (3,5-di(t-butyl)-4-methylphenoxy)diisobutylaluminum), methylalumoxane, modified methylalumoxane and diisobutylalumoxane. The molar ratio of aluminum compound to metal complex is preferably from 1:10,000 to 1000:1, more preferably from 1:5000 to 100:1, most preferably from 1:100 to 100:1.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and a compatible, noncoordinating anion, A–. Preferred supporting electrolytes are salts corresponding to the formula

$G^+A^-$;

wherein:

$G^+$ is a cation which is nonreactive towards the starting and resulting complex, and $A^-$ is as previously defined.

Examples of cations, $G^+$, include tetrahydrocarbyl substituted ammonium or phosphonium cations having up to 40 nonhydrogen atoms. Preferred cations are the tetra(n-butylammonium)- and tetraethylammonium-cations.

During activation of the complexes of the present invention by bulk electrolysis the cation of the supporting electrolyte passes to the counter electrode and A-migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl)borates having from 1 to 10 carbons in each hydrocarbyl or perfluoroaryl group, especially tetra(n-butylammonium)tetrakis(pentafluorophenyl)borate.

A further recently discovered electrochemical technique for generation of activating cocatalysts is the electrolysis of a disilane compound in the presence of a source of a noncoordinating compatible anion. This technique is more fully disclosed and claimed in the previously mentioned U.S. Pat. No. 5,625,087.

The foregoing electrochemical activating technique and activating cocatalysts may also be used in combination. An especially preferred combination is a mixture of a tri (hydrocarbyl)aluminum or tri(hydrocarbyl)borane compound having from 1 to 4 carbons in each hydrocarbyl group with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris (pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The process may be used to polymerize ethylenically unsaturated monomers having from 3 to 20 carbon atoms either alone or in combination. Preferred monomers include monovinylidene aromatic monomers, 4-vinylcyclohexene, vinylcyclohexane, norbornadiene and $C_{3-10}$ aliphatic α-olefins (especially ethylene, propylene, isobutylene, 1-butene, 1-hexene, 3-methyl-1-pentene, 4-methyl-1-pentene, and 1-octene), $C_{4-40}$ dienes, and mixtures thereof. Most preferred monomers are ethylene, and mixtures of ethylene, propylene and a nonconjugated diene, especially ethylidenenorbornene.

In general,. the polymerization may be accomplished at conditions well known in the prior art for Ziegler-Natta or Kaminsky-Sinn type polymerization reactions, that is, temperatures from 0 to 250° C., preferably 30 to 200° C. and pressures from atmospheric to 10,000 atmospheres (1000 MPa). Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}$:1 to $10^{-1}$:1, more preferably from $10^{-9}$:1 to $10^{-5}$:1.

Suitable solvents for polymerization are inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and the like and aromatic and alkyl-substituted aromatic compounds such as benzene, toluene, xylene, ethylbenzene and the like. Suitable solvents also include liquid olefins which may act as monomers or comonomers including ethylene, propylene, butadiene, cyclopentene, 1-hexene, 1-hexane, 4-vinylcyclohexene, vinylcyclohexane, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable.

The catalysts may be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770, as well as WO 94/17112, equivalent to U.S. Ser. No. 08/10958, filed Jan. 29, 1993.

Utilizing the catalysts of the present invention copolymers having high comonomer incorporation and correspondingly low density, yet having a low melt index may be readily prepared. That is, high molecular weight polymers are readily attained by use of the present catalysts even at elevated reactor temperatures. This result is highly desirable because the molecular weight of α-olefin copolymers can be readily reduced by the use of hydrogen or similar chain transfer agent, however increasing the molecular weight of α-olefin copolymers is usually only attainable by reducing the polymerization temperature of the reactor. Disadvantageously, operation of a polymerization reactor at reduced temperatures significantly increases the cost of operation since heat must be removed from the reactor to maintain the reduced reaction temperature, while at the same time heat must be added to the reactor effluent to vaporize the solvent. In addition, productivity is increased due to improved polymer solubility, decreased solution viscosity, and a higher polymer concentration. Utilizing the present catalysts, α-olefin homopolymers and copolymers having densities from 0.85 g/cm³ to 0.96 g/cm³, and melt flow rates from 0.001 to 10.0 dg/min are readily attained in a high temperature process.

The polymers of the present invention will preferably have high levels of long chain branching. The use of the catalysts described herein in the production of the polymers of the present invention in continuous polymerization processes, especially continuous, solution polymerization processes, allows for elevated reactor temperatures which favor the formation of vinyl terminated polymer chains that may be incorporated into a growing polymer, thereby giving a long chain branch. The use of the catalysts described herein in the production of the polymers of the present invention advantageously allows for the economical production of ethylene/α-olefin copolymers having processability similar to high pressure, free radical produced low density polyethylene.

The polymers of the present invention will preferably have at least 0.03, more preferably at least 0.04 vinyls/1000 carbons, as determined by FTIR.

The polymers of the invention will preferably be characterized as having long chain branching, preferably from 0.01 to 3.0 long chain branches/1000 carbons. Methods for determining the amount of long chain branching present, both qualitatively and quantitatively, are known in the art.

For qualitative methods for determination, see, e.g., U.S. Pat. Nos. 5,272,236 and 5,278,272, the disclosures of both of which are incorporated herein by reference, which disclose the use of an apparent shear stress versus. apparent shear rate plot to identify melt fracture phenomena. Preferred polymers of the present invention will possess a gas extrusion rheology such that: (a) the critical shear rate at the onset of surface melt fracture for the inventive polymer is at least 50 percent greater than the critical shear rate at the onset of surface melt fracture for a linear polymer having the same comonomer or comonomers and having an $I_2$, $M_w/M_n$ and density within ten percent of that of the inventive polymer, and wherein the respective critical shear rates of the inventive polymer and the linear polymer are measured at the same melt temperature using a gas extrusion rheometer; or (b) the critical shear rate at the onset of gross melt fracture is greater than $4 \times 10^6$ dynes/cm², as determined by gas extrusion rheometry.

For quantitative methods for determination, see, e.g., U.S. Pat. Nos. 5,272,236 and 5,278,272; Randall (Rev. Macromol. Chem. Phys., C29 (2&3), p. 285–297), which discusses the measurement of long chain branching using 13C nuclear magnetic resonance spectroscopy, Zimm, G. H. and Stockmayer, W. H., J. Chem. Phys., 17, 1301 (1949); and Rudin, A., Modern Methods of Polymer Characterization, John Wiley & Sons, New York (1991) pp. 103–112, which discuss the use of gel permeation chromatography coupled with a low angle laser light scattering detector (GPC-LALLS) and gel permeation chromatography coupled with a differential viscometer detector (GPC-DV). Each of these references is incorporated herein by reference.

The inventive polymers are further characterized as having a melt flow ratio ($I_{10}/I_2$) which may be varied independently of the polydispersity index, i.e., the molecular weight distribution $M_w/M_n$. This feature accords the inventive polymers with a high of degree of processability despite a narrow molecular weight distribution. Preferably, the polymers of the invention will have an $I_{10}/I_2$ which is at least 10, preferably at least 15, with $I_{10}/I_2$ values exceeding 20 being possible.

ATREF/DV may be further used to illustrate the fact that the preferred copolymers of the invention are characterized as having a bimedal molecular weight distribution. It is significant to note that the ATREF peaks are quite sharp, and are distinguishable from copolymers which are produced using supported catalyst systems. Specifically, (i) the maximum ATREF peak height is measured, (ii) the width of the total ATREF peak at ½ the maximum peak height is measured, the ATREF shape factor is calculated, that is, the ratio (ii)/(i), and the average ATREF elution temperature is determined, that is, (minimum ATREF elution temp+ maximum ATREF elution temp)/2. The polymers of the invention will be characterized as having an ATREF curve which satisfies the following inequality:

ATREF Shape Factor$\leq$0.90–0.00626 (Average Elution Temperature) which preferably satisfies the following inequality:

ATREF Shape Factor$\leq$0.75–0.00626 (Average Elution Temperature) and which most preferably satisfies the following inequality:

ATREF Shape Factor$\leq$0.70–0.00626 (Average Elution Temperature).

The polymer compositions of the invention are characterized as having a fraction which has a higher crystallinity than the other fraction. The presence of the higher crystallinity fraction translated to an enhancement in the upper service temperature of the polymer compositions of the invention, with respect to the comparative compositions. The uppeer service temperature may be defined as the intersection of a line drawn across the upper non melted plateau region and the descending melting transition region of the log G1 versus temperature plot. Preferably the upper service temperature of the olefin interpolymer (UST (interpolymer)) is greater than the upper service temperature of a physical blend (UST (blend)) of a first homogenous olefin polymer having a density equal to the first density, an $I_2$ equal to the first $I_2$, and which is provided in the first weight percent, and a second homogeneous olefin polymer having a density equal to the second density, an $I_2$ equal to the second $I_2$, and which is provided in the second weight percent, in accordance with the following inequality:

UST (interpolymer)–UST (blend)$\geq$256–275 (density of olefin interpolymer).

The polymers of the present invention will preferably have improved processing properties, whether they result from polymerizing ethylene alone or ethylene/α-olefin mixtures with low levels of a "H" branch inducing diene, such as norbornadiene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processability. Preferably such polymers comprise ethylene, a C3-20 α-olefin and a "H"-branching comonomer. Preferably, such polymers are produced in a solution process, most preferably a continuous solution process.

As previously mentioned, the polymers of the present invention may be prepared via a solution or slurry process both of which are previously known in the art. Kaminsky, J. Poly. Sci., Vol. 23, pp. 2151–64 (1985) reported the use of a soluble bis(cyclopentadienyl) zirconium dimethyl-alumoxane catalyst system for solution polymerization of EP and EPDM elastomers. U.S. Pat. No. 5,229,478 disclosed a slurry polymerization process utilizing similar bis (cyclopentadienyl) zirconium based catalyst systems.

In general terms, it is desirable to produce such EP and EPDM elastomers under conditions of increased reactivity of the diene monomer component. The reason for this was explained in U.S. Pat. No. 5,229,478 in the following manner, which still remains true despite the advances attained in such reference. A major factor affecting production costs and hence the utility of an EPDM is the diene monomer cost. The diene is a more expensive monomer material than ethylene or propylene. Further, the reactivity of diene monomers with previously known metallocene catalysts is lower than that of ethylene and propylene. Consequently, to achieve the requisite degree of diene incorporation to produce an EPDM with an acceptably fast cure rate, it has been necessary to use a diene monomer concentration which, expressed as a percentage of the total concentration of monomers present, is in substantial excess compared to the percentage of diene desired to be incorporated into the final EPDM product. Since substantial amounts of unreacted diene monomer must be recovered from the polymerization reactor effluent for recycle, the cost of production is increased unnecessarily.

Further adding to the cost of producing an EPDM is the fact that, generally, the exposure of an olefin polymerization catalyst to a diene, especially the high concentrations of diene monomer required to produce the requisite level of diene incorporation in the final EPDM product, often reduces the rate or activity at which the catalyst will cause polymerization of ethylene and propylene monomers to proceed. Correspondingly, lower throughputs and longer reaction times have been required, compared to the production of an ethylene-propylene copolymer elastomer or other α-olefin copolymer elastomer.

The present catalyst system advantageously allows for increased diene reactivity thereby preparing EPDM polymers in high yield and productivity. Additionally, the catalyst system of the present invention achieves the economical production of EPDM polymers with diene contents of up to 20 weight percent or higher, which polymers possess highly desirable fast cure rates.

The non-conjugated diene monomer can be a straight chain, branched chain or cyclic hydrocarbon diene having from 6 to 15 carbon atoms. Examples of suitable non-conjugated dienes are straight chain acyclic dienes such as 1,4-hexadiene and 1,6-octadiene: branched chain acyclic dienes such as 5-methyl-1,4-hexadiene; 3,7-dimethyl-1,6-octadiene; 3,7-dimethyl-1,7-octadiene and mixed isomers of dihydromyricene and dihydroocinene: single ring alicyclic dienes such as 1,3-cyclopentadiene; 1,4-cyclohexadiene; 1,5-cyclooctadiene and 1,5-cyclododecadiene: and multiring alicyclic fused and bridged ring dienes such as tetrahydroindene, methyl tetrahydroindene, dicyclopentadiene; bicyclo-(2,2,1)-hepta-2,5-diene; alkenyl, alkylidene, cycloalkenyl and cycloalkylidene norbornenes such as 5-methylene-2-norbornene (MNB); 5-propenyl-2-norbornene,5-isopropylidene-2-norbomene, 5-(4-cyclopentenyl)-2-norbornene, 5-cyclohexylidene-2-norbornene, 5-vinyl-2-norbornene and norbornadiene. Another preferred diene is piperylene.

Of the dienes typically used to prepare EPDMs, the particularly preferred dienes are 1,4-hexadiene (HD), 5-ethylidene-2-norbornene (ENB), 5-vinylidene-2-norbornene (VNB), 5-methylene-2-norbornene (MNB), and dicyclopentadiene (DCPD). The especially preferred dienes are 5-ethylidene-2-norbornene (ENB) and 1,4-hexadiene (HD). Another preferred diene is piperylene.

The preferred EPDM elastomers may contain 20 up to 90 weight percent ethylene, more preferably 30 to 85 weight percent ethylene, most preferably 35 to 80 weight percent ethylene.

The alpha-olefins suitable for use in the preparation of elastomers with ethylene and dienes are preferably $C_{3-16}$ alpha-olefins. Illustrative non-limiting examples of such alpha-olefins are propylene, 1-butene, 1-pentene, 1-hexene, 1-octene, 1-decene, and 1-dodecene. The alpha-olefin is generally incorporated into the EPDM polymer at 10 to 80 weight percent, more preferably at 20 to 65 weight percent. The non-conjugated dienes are generally incorporated into the EPDM at 0.5 to 20 weight percent; more, preferably at 1 to 15 weight percent, and most preferably at 3 to 12 weight percent. If desired, more than one diene may be incorporated simultaneously, for example HD and ENB, with total diene incorporation within the limits specified above.

The catalyst system may be prepared as a homogeneous catalyst by addition of the requisite components to a solvent in which polymerization will be carried out by solution polymerization procedures. The catalyst system may also be prepared and employed as a heterogeneous catalyst by adsorbing the requisite components on a catalyst support material such as silica gel, alumina or other suitable inorganic support material. When prepared in heterogeneous or supported form, it is preferred to use silica as the support material. The heterogeneous form of the catalyst system is employed in a slurry polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise the α-olefin monomer or a mixture of different α-olefin monomers may be used in whole or part as the diluent. Most preferably the diluent comprises in at least major part the α-olefin monomer or monomers to be polymerized.

In contrast, solution polymerization conditions utilize a solvent for the respective components of the reaction, particularly the EP or EPDM polymer. Preferred solvents include mineral oils and the various hydrocarbons which are liquid at reaction temperatures. Illustrative examples of useful solvents include alkanes such as pentane, iso-pentane, hexane, heptane, octane and nonane, as well as mixtures of alkanes including kerosene and Isopar E™, available from Exxon Chemicals Inc.; cycloalkanes such as cyclopentane and cyclohexane; and aromatics such as benzene, toluene, xylenes, ethylbenzene and diethylbenzene.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas such as, for example, nitrogen.

Ethylene is added to the reaction vessel in an amount to maintain a differential pressure in excess of the combined vapor pressure of the α-olefin and diene monomers. The ethylene content of the polymer is determined by the ratio of ethylene differential pressure to the total reactor pressure. Generally the polymerization process is carried out with a differential pressure of ethylene of from 10 to 1000 psi (70 to 7000 kPa), most preferably from 40 to 400 psi (30 to 300 kPa). The polymerization is generally conducted at a temperature of from 25 to 200° C., preferably from 75 to 170° C., and most preferably from greater than 95 to 140° C.

The polymerization may be carried out as a batchwise or a continuous polymerization process A continuous process is preferred, in which event catalyst, ethylene, α-olefin, and optionally solvent and diene are continuously supplied to the reaction zone and polymer product continuously removed therefrom.

Without limiting in any way the scope of the invention, one means for carrying out such a polymerization process is as follows/ In a stirred-tank reactor propylene monomer is introduced continuously together with solvent, diene monomer and ethylene monomer. The reactor contains a liquid phase composed substantially of ethylene, propylene and diene monomers together with any solvent or additional diluent. If desired, a small amount of a "H"-branch inducing diene such as norbornadiene, 1,7-octadiene or 1,9-decadiene may also be added. Catalyst and cocatalyst are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to propylene in the reactor, which is controlled by manipulating the respective feed rates of these components to the reactor. The polymer product molecular weight is controlled, optionally, by controlling other polymerization variables such as the temperature, monomer concentration, or by a stream of hydrogen introduced to the reactor, as is well known in the art. The reactor effluent is contacted with a catalyst kill agent such as water. The polymer solution is optionally heated, and the polymer product is recovered by flashing off gaseous ethylene and propylene as well as residual solvent or diluent at reduced pressure, and, if necessary, conducting further devolatilization in equipment such as a devolatilizing extruder. In a continuous process, the mean residence time of the catalyst and polymer in the reactor generally is from 5 minutes to 8 hours, and preferably from 10 minutes to 6 hours.

In a preferred manner of operation, the polymerization is conducted in a continuous solution polymerization system comprising two reactors connected in series or parallel. In one reactor, a product having a molecular weight (M,) of from 300,000 to 600,000, more preferably 400,000 to 500,000, is formed while in the second reactor a product of a second molecular weight ($M_w$) of 50,000 to 300,000) is formed. The final product is a blend of the two reactor effluents which are combined prior to devolatilization to result in a uniform blend of the two polymer products. Such a dual reactor process allows for the preparation of products having improved properties. In a preferred embodiment the reactors are connected in series, that is effluent from the first reactor is charged to the second reactor and fresh monomer, solvent and hydrogen is added to the second reactor. Reactor conditions are adjusted such that the weight ratio of polymer produced in the first reactor to that produced in the second reactor is from 20:80 to 80:20. In addition the temperature of the second reactor is controlled to produce the lower molecular weight product. This system beneficially allow for production of EPDM products having a large range of Mooney viscosities, as well as excellent strength and processability. Preferably the Mooney viscosity (ASTM D1646-94, ML1+4 at 125° C.) of the resulting product is adjusted to fall in the range from 1 to 200, preferably from 5 to 150, and most preferably from 10 to 110.

EXAMPLES

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis.

$^1$H and $^{13}$C NMR spectra were recorded on a Varian XL (300 MHz) spectrometer. Chemical shifts were determined relative to TMS or through the residual CHCl$_3$ in CDCl$_3$ or the residual C$_6$HD$_5$ in C$_6$D$_6$, relative to TMS. Tetrahydrofuran (THF), diethylether, toluene, and hexane were used following passage through double columns charged with activated alumina and alumina supported mixed metal oxide catalyst (Q-5® catalyst, available from Engelhard Corp.) The compounds n-BuLi, KH, all Grignard reagents, and 1,4-diphenyl-1,3-butadiene were all used as purchased from Aldrich Chemical Company. All syntheses were performed under dry nitrogen atmosphere using a combination of glove box and high vacuum techniques.

Preparation of Catalyst One: [(N-isopropylamido)(dimethyl)(2,3,4,6-tetramethylindenyl)silane] Titanium Dimethyl Preparation of Dimethylsilyl(2,3,4,6-tetramethylindenyl) (isopropylamine):

Dimethylsilyl(2,3,4,6-tetramethylindenyl)Cl (22.29 grams, 84.17 mmol) was stirred in THF as i-PrNH$_2$ (28.68 mL, 336.7 mmol) was added. The mixture was stirred for 16 hours. The volatiles were removed under reduced pressure. The residue was extracted with hexane and filtered through a diatomaceous earth filter aid on a 10–15 mm glass frit. The hexane was removed under reduced pressure to afford the product as a yellow oil. Yield; 17.23 grams, 71 percent.

Preparation of [(N-isopropylamido)(dimethyl)(2,3,4,6-tetramethylindenyl)silane] Titanium Dichloride:

In the drybox, 17.23 grams (59.93 mmol) of dimethylsilyl (2,3,4,6-tetramethylindenyl)(isopropylamine) was dissolved in 350 mL of hexane in a 500 mL round-bottom schlenk flask. Two equivalents of n-BuLi (47.94 mL, 2.5 M in hexanes) were then added via syringe. The reaction was stirred for twelve hours. The solvent was removed under reduced pressure to afford a orange powder. The powder was dissolved in 250 mL of THF. TiCl$_3$(THF)$_3$ (22.2 grams, 59.93 mmol) was added as a solid. After 15 minutes, CH$_2$Cl$_2$ (2.48 mL, 29.97 mmol) was added. After two hours, the solvent was removed under reduced pressure. The residue was extracted with toluene and filtered through a diatomaceous earth filter aid on a 10 to 15 mm glass frit. The toluene was removed under reduced pressure. The residue was slurried in hexane and filtered over a 10–15 mm glass frit. The residue was dried under reduced pressure to afford a red powder. Yield; 12.3 grams, 51 percent.

Preparation of [(N-isopropylamido)(dimethyl)(2,3,4,6-tetramethylindenyl)silane] Titanium Dimethyl:

In the drybox, [(N-isopropylamido)(dimethyl)(2,3,4,6-tetramethylindenyl)silane]titanium dichloride (6.92 grams, 17.12 mmol) was suspended in 150 mL of Et$_2$O in a 250 mL round bottom flask. Two equivalents of a 3.0 M THF solution of MeMgCl (11.41 mL, 34.23 mmol) were added. The mixture was stirred for one hour. The volatiles were removed under reduced pressure. The residue was extracted with hexane and filtered through a diatomaceous earth filter aid on a 10 to 15 mm glass frit. The hexane was removed under reduced pressure to afford a orange powder. Yield; 5.8 grams, 93 percent.

Preparation of Catalyst Composition Two [(N-cyclohexylamido)(dimethyl) (2,3,4,6-tetramethylindenyl)silanel Titanium Dimethyl:

Preparation of Dimethylsilyl(2,3,4,6-tetramethylindenyl) (cyclohexylamine):

Dimethylsilyl(2,3,4,6-tetramethylindenyl)Cl (9.95 g, 37.8 mmol) was stirred in hexane (200 mL) as NEt$_3$ (4.1 g, 40.6 mmol) was added followed by cyclohexylamine (4.05 g, 40.8 mmol). This mixture was allowed to stir for 24 hours at 20° C. After the reaction period the mixture was filtered and the desired product isolated as a pale yellow oil following the removal of the volatiles (10.98 g, 89.3 percent yield).

Preparation of Dilithium (N-cyclohexylamido)(dimethyl) (2,3,4,6-tetramethylindenyl)silane:

In the drybox 4.0 g (12.6 mmol) of (N-cyclohexylamino) (dimethyl) (2,3,4,6-tetramethylindenyl) silane was dissolved in 300 ml of hexane. To this solution 12.6 ml (25.2 mmol) of nBuLi (2.00 M) was added dropwise at 20° C. Upon complete addition of the nBuLi the solution was stirred for 12 hours after which the solvent was removed under reduced pressure to give 4.12 g (96 percent yield) of a yellow-orange powder.

Preparation of [(N-cyclohexylamido)(dimethyl)(2,3,4,6-tetramethylindenyl)silane] Titanium Dichloride:

In the drybox 4.63 g (12.5 mmol) of TiCl$_3$(THF)$_3$ was dissolved in 75 ml of THF. To this solution 4.12 g (12.5 mmol) of dilithium (N-cyclohexylamido) (dimethyl)(2,3,4, 6-tetramethylindenyl)silane was added as a solid while stirring at 20° C. The solution was then stirred for 45 minutes. After this time period 1.73 g of PbCl$_2$ (6.25 mmol) was added and the solution stirred for 45 minutes. The THF was then removed under reduced pressure. The residue was then extracted with toluene, the solution filtered, and the toluene removed under reduced pressure. The residue was then triturated with hexane and the solution volume reduced whereupon a red precipitate was formed and collected via filtration and washed with cold (0° C.) hexane. The solid product was dried under vacuum to yield 1.70 g (31 percent yield) of product.

Preparation of [(N-cyclohexylamido)(dimethyl)(2,3,4,6-tetramethylindenyl)silane] Titanium Dimethyl:

In the drybox 0.300 g of [(N-t-cyclohexylamino) (dimethyl)(2,3,4,6-tetramethylindenyl) silane]titanium dichloride (0.675 mmol) was suspended in 50 ml of $Et_2O$ at 20° C. To this suspension, 0.45 ml of MeMgI (3.0 M) was added dropwise while stirring over a 20 minute period. After the addition MeMgI was completed, the solution was stirred for 40 minutes. Then the $ET_2O$ was removed under reduced pressure and the residue extracted with hexane, the solution filtered, the filtrate evaporated to dryness under reduced pressure to give 0.27 g (100 percent yield) of product.

Preparation of Catalyst Composition Three [(tetramethylcyclopentadienyl) dimethyl(t-butylamido)silane] Titanium 1.3-pentadiene
Preparation of $TiCl_3(DME)_{1.5}$ The apparatus (referred to as R-1) was set-up in the hood and purged with nitrogen; it consisted of a 10 L glass kettle with flush mounted bottom valve, 5-neck head, polytetrafluoroethylene gasket, clamp, and stirrer components (bearing, shaft, and paddle). The necks were equipped as follows: stirrer components were put on the center neck, and the outer necks had a reflux condenser topped with gas inlet/outlet, an inlet for solvent, a thermocouple, and a stopper. Dry, deoxygenated dimethoxyethane (DME) was added to the flask (approx. 5.2 L). In the drybox, 300 g of $TiCl_3$ was weighed into an equalizing powder addition funnel; the funnel was capped, removed from the drybox, and put on the reaction kettle in place of the stopper. The $TiCl_3$ was added over about 10 minutes with stirring. After the addition was completed, additional DME was used to wash the rest of the TiCl3 into the flask. This process was then repeated with 325 g of additional TiCl3, giving a total of 625 g. The addition funnel was replaced with a stopper, and the mixture heated to reflux. The color changed from purple to pale blue. The mixture was heated for about 5 hours, cooled to room temperature, the solid was allowed to settle, and the supernatant was decanted from the solid. The TiCl3(DME)1.5 was left in R-1 as a pale blue solid.
Preparation of [(Me4C5)SiMe2NtBu][MqCl]2

The apparatus (referred to as R-2) was set-up as described for R-1, except that flask size was 30 L. The head was equipped with seven necks; stirrer in the center neck, and the outer necks containing condenser topped with nitrogen inlet/outlet, vacuum adapter, reagent addition tube, thermocouple, and stoppers. The flask was loaded with 7 L of toluene, 3.09 kg of 2.17 M iPrMgCl in ET2O, 250 mL of THF, and 1.03 kg of (Me4C5H)SiMe2NHtBu. The mixture was then heated, and the ether allowed to boil off into a trap cooled to −78° C. After three hours, the temperature of the mixture had reached 80 ° C., at which time a white precipitate formed. The temperature was then increased to 90° C. over 30 minutes and held at this temperature for 2 hours. At the end of this time, the heater was turned off, and 2 L of DME was added to the hot, stirring solution, resulting in the formation of additional precipitate. The solution was allowed to cool to room temperature, the material was allowed to settle, and the supernatant was decanted from the solid. An additional wash was done by adding toluene, stirring for several minutes, allowing the solids to settle, and decanting the toluene solution. The [(Me4C5)SiMe2NtBu][MgCl]2 was left in R-2 as an off-white solid.
Preparation of [(h5-Me4C5)SiMe2NtBulTi(h4−1,3-pentadiene)

The materials in R-1 and R-2 were slurried in DME (the total volumes of the mixtures were approx. 5 L in R-1 and 12 L in R-2). The contents of R-1 were transferred to R-2 using a transfer tube connected to the bottom valve of the 10 L flask and one of the head openings in the 30 L flask. The remaining material in R-1 was washed over using additional DME. The mixture darkened quickly to a deep red/brown color. After 15 minutes, 1050 mL of 1,3-pentadiene and 2.60 kg of 2.03 M nBuMgCl in THF were added simultaneously. The maximum temperature reached in the flask during this addition was 53° C. The mixture was stirred for 2 hours, then approx. 11 L of solvent was removed under vacuum. Hexane was then added to the flask to a total volume of 22 L. The material was allowed to settle, and the liquid layer (12 L) was decanted into another 30 L glass kettle (R-3). An additional 15 liters of product solution was collected by adding hexane to R-2, stirring for 50 minutes, again allowing to settle, and decanting. This material was combined with the first extract in R-3. The solvent in R-3 was removed under vacuum to leave a red/black solid, which was then extracted with toluene. This material was transferred into a storage cylinder. Analysis indicated that the solution (11.75 L) was 0.255 M in titanium; this is equal to 3.0 moles of $[(\eta^5-Me_4C_5)SiMe_2NtBu]Ti(\eta^41,3pentadiene)$ or 1095 g. This is a % yield based on the titanium added as TiCl3.

Preparation of the Soluble Borate Cocatalyst ((bis (hydrogenated-tallowalkyl)methylamine) (B-FABA)

Methylcyclohexane (1200 mL) was placed in a 2L cylindrical flask. While stirring, bis(hydrogenated-tallowalkyl) methylamine (ARMEEN® M2HT, 104 g, ground to a granular form) was added to the flask and stirred until completely dissolved. Aqueous HCl (1M, 200 mL) was added to the flask, and the mixture was stirred for 30 minutes. A white precipitate formed immediately. At the end of this time, $LiB(C_6F_5)_4 \cdot Et_2O \cdot 3$ LiCl (MW=887.3; 177.4 g) was added to the flask. The solution began to turn milky white. The flask was equipped with a 6 inch (15 cm) Vigreux column topped with a distillation apparatus and the mixture was heated (140° C. external wall temperature). A mixture of ether and methylcyclohexane was distilled from the flask. The two-phase solution was now only slightly hazy. The mixture was allowed to cool to room temperature, and the contents were placed in a 4 L separatory funnel. The aqueous layer was removed and discarded, and the organic layer was washed twice with $H_2O$ and the aqueous layers again discarded. The product solution was divided into two equal portions for the evaluation of two workup procedures. These $H_2O$ saturated methylcyclohexane solutions were measured to contain 0.48 wt percent diethylether ($Et_2O$).

The solution (600 mL) was transferred into a 1 L flask, sparged thoroughly with nitrogen, and transferred into the drybox. The solution was passed through a column (1 inch (2.5cm) diameter, 6 inch (15 cm) height) containing 13 times molecular sieves. This reduced a the level of $Et_2O$ from 0.48 weight percent to 0.28 weight percent. The material was then stirred over fresh 13 times sieves (20 g) for four hours. The Et$_2$O level was then measured to be 0.19 weight percent. The mixture was then stirred overnight, resulting in a further reduction in Et$_2$O level to approximately 40 ppm. The mixture was filtered using a funnel equipped with a glass frit having a pore size of 10 to 15 μm to give a clear solution (the molecular sieves were rinsed with additional dry methylcyclohexane). The concentration was measured by gravimetric analysis yielding a value of 16.7 wt percent.

Polymerization of Polymers of the Examples of the Invention and of the Comparative Examples The polymer products of the Examples were produced in a solution polymerization process using a well-mixed recirculating loop reactor. In the case of polymers produced with Catalyst One, the additive package was 1500 ppm calcium stearate, 600 ppm Irganox™ 1076 hindered phenolic antioxidant, and 950 ppm PEPQ (tetrakis(2,4-di-t-butylphenyl)-4,4'-biphenylene diphosphonite) (available from Clariant Corporation). In the case of polymers produced with Catalyst Two, the additive package was 1450 ppm calcium stearate, 600 ppm Irganox™ 1076, and 930 ppm PEPQ. In the case of polymers produced with Catalyst Three, the additive package was 640 ppm calcium stearate, 260 ppm Irganox™ 1076, and 400 ppm PEPQ.

The ethylene and the hydrogen (as well as any ethylene and hydrogen which were recycled from the separator, were combined into one stream before being introduced into the diluent mixture, a mixture of C$_8$–C$_{10}$ saturated hydrocarbons, for example, ISOPAR™-E (available from Exxon Chemical Company) and the comonomer 1-octene.

The metal complex and cocatalysts were combined into a single stream and were also continuously injected into the reactor. In the case of Examples 1a, 1b, and 1c, the catalyst was as prepared in Catalyst Preparation One. In the case of Examples 2a, 2b, 2c, and 2d, the catalyst was as prepared in Catalyst Preparation Two. In the case of the Comparative Examples C-3a and C-3b, the catalyst was as prepared in Catalyst Preparation Three. In each of the Examples and Comparative Examples, the Primary and Secondary cocatalysts were as prepared in Cocatalyst Example One and Cocatalyst Example Two.

Sufficient residence time was allowed for the metal complex and cocatalyst to react prior to introduction into the polymerization reactor. The reactor pressure was held constant at about 450 to 475 psig (3.1 to 3.3 MPa).

After polymerization, the reactor exit stream was introduced into a separator where the molten polymer was separated from the unreacted comonomer(s), unreacted ethylene, unreacted hydrogen, and diluent mixture stream, which was in turn recycled for combination with fresh comonomer, ethylene, hydrogen, and diluent, for introduction into the reactor. The molten polymer was subsequently strand chopped or pelletized, and, after being cooled in a water bath or pelletizer, the solid pellets were collected. Table One describes the polymerization conditions and the resultant polymer properties.

TABLE 1

Run Conditions

| Example Number | Catalyst | solvent feed (kg/hr) | ethylene feed (kg/hr) | octene feed (kg/hr) | Feed temp (° C.) | solvent/ ethylene ratio | R1 temp (° C.) | Oil temp (° C.) | ethylene conv percent | Catalyst conc. (ppm Ti) | Catalyst timer percent | B-FABA timer percent | DIBAL-BOT timer percent | B/Ti (molar) | Al/Ti (molar) ° C. |
|---|---|---|---|---|---|---|---|---|---|---|---|---|---|---|---|
| C-3a | Three | 21.0 | 2.17 | 2.20 | 0.0 | 10.69 | 88.0 | 77 | 84.0 | 37 | | | | | |
| 1a | One | 21.0 | 2.17 | 2.00 | −0.4 | 10.60 | 122.0 | 119 | 85.0 | 47 | 25 | 20 | 25 | 10.4 | 26.0 |
| 1b | One | 21.0 | 2.17 | 2.20 | −0.4 | 10.69 | 122.0 | 119 | 85.6 | 47 | 60 | 175 | 25 | 4.9 | 0.2 |
| 1c | One | 21.0 | 2.17 | 2.20 | −0.4 | 10.69 | 122.0 | 119 | 85.6 | 47 | 60 | 175 | 25 | 4.9 | 0.2 |
| 2a | Two | 21.0 | 2.17 | 1.98 | 0.3 | 10.59 | 129.4 | 136 | 84.4 | 46 | 60 | 175 | 25 | 4.9 | 0.2 |
| 2b | Two | 21.0 | 2.17 | 1.98 | 0.3 | 10.59 | 129.4 | 134 | 84.1 | 46 | 71 | 120 | 50 | 3.0 | 4.9 |
| 2c | Two | 21.0 | 2.17 | 1.98 | 0.3 | 10.59 | 129.5 | 132 | 83.5 | 46 | 71 | 120 | 50 | 2.2 | 3.3 |
| 2d | Two | 21.0 | 2.17 | 1.98 | 0.3 | 10.59 | 129.0 | 136 | 85.1 | 48 | 74 | 120 | 50 | 1.9 | 0.5 |
| C-3b | Three | 21.0 | 2.17 | 2.40 | 0.0 | 10.78 | 122.0 | 118 | 85.0 | 26 | 45 | 100 | 0.9 | 2.5 |

The following Table Two compares the melt index (I$_2$), density and melt flow ratio (I$_{10/I2}$) of the ethylene/octene copolymers produced using Catalyst Composition Three with the polymers of the invention prepared using Catalyst Compositions One and Two. Significantly higher molecular weight copolymers were produced using Catalyst Compositions One and Two than were produced using Catalyst Composition Three. For example, at a reactor temperature of 122° C., Catalyst One produced a polymer having an I$_2$ of 0.7 dg/min, while Catalyst Three produced a polymer having an I$_2$ of 116 dg/min copolymer. The use of Catalysts One and Two is advantageous, in that they permit one to produce a copolymer of a specific molecular weight at a higher reactor temperature, thus reducing solution viscosity, reactor pressure drop, reactor fouling and improving the overall process economics.

As further illustrated in Table two, the copolymers produced using Catalysts One and Two had higher melt flow ratios. Such higher melt flow ratios are desirable, in that copolymers with higher melt flow ratios are easier to process, i.e., significantly lower pressures and amps are observed during the conversion of such copolymers into plastic parts.

solvent. The polymerization was allowed to proceed for 10 minutes while feeding ethylene on demand to maintain a pressure of 445 psig (3.07 MPa). The amount of ethylene consumed during the reaction was monitored using a mass flow meter. The polymer solution was dumped from the reactor into a nitrogen-purged glass kettle containing 10 to 20 mL of isopropanol. An aliquot of the additive solution described below was added to this kettle and the solution stirred thoroughly (the amount of additive used was chosen based on the total ethylene consumed during the

TABLE Two

Characterization Information for Polymers of the Examples and Comparative Examples

| Example | Catalyst | Reaction temperature (° C.) | $I_2$ (g/10 min.) | $I_{10}$ | $I_{10}/I_2$ | Annealed Density (g/cm$^3$) |
|---|---|---|---|---|---|---|
| C-3a | Three | 88.0 | 0.48 | 4.5 | 9.38 | 0.8667 |
| 1a | One | 122.0 | 0.71 | 8.22 | 11.58 | 0.8710 |
| 1b | One | 122.0 | 0.63 | 7.74 | 12.29 | 0.8700 |
| 1c | One | 122.0 | 0.82 | 8.95 | 10.91 | 0.8703 |
| 2a | Two | 129.4 | 0.5 | 7.61 | 15.22 | 0.8606 |
| 2b | Two | 129.4 | 0.43 | 5.84 | 13.58 | 0.8612 |
| 2c | Two | 129.5 | 0.38 | 5.47 | 14.39 | 0.8612 |
| 2d | Two | 129.0 | 0.38 | 3.84 | 10.11 | 0.8615 |
| C-3b | Three | 122.0 | 116 | 650 | 6.00 | 0.8612 |
| C-2a* | Two | | 0.49 | | 6.53 | 0.8635 |

*Sample prepared in a batch reactor.

Batch polymerization experiments were performed using a 1 gallon stirred Autoclave Engineers reactor. The reactor was charged with 1440 g of Isopar E, the designated amounts of 1-octene, and hydrogen, and then heated to the desired temperature and saturated with ethylene to 450 psig (3.1 MPa). The catalyst was prepared in a drybox by springing together the catalyst, cocatalyst, and scavenger solutions with additional solvent to give a total volume of 17 mL. The catalyst solution was then transferred by syringe to a catalyst addition loop and injected into the reactor over approximately 4 minutes using a flow of high pressure polymerization). The polymer solution was dumped into a tray, air dried overnight, then thoroughly dried in a vacuum oven for two days. The weights of the polymers were recorded and the efficiency calculated as grams of polymer per gram of transition metal.

Differential scanning calorimeter (DSC) data for the polymers of the Examples and the Comparative Examples are set forth in the following Table Three:

TABLE Three

Differential scanning calorimetry (DSC) data for the polymer compositions of the invention and of the Comparative Examples

| | | DSC | | | | Calculated | | |
| | | | | | | Tm1 | Tm2 | |
| | Catalyst | Tm1 (° C.) | Tm2 (° C.) | Tc1 (° C.) | Tc2 (° C.) | Density (g/cc) | Density (g/cc) | ASTM Annealed Density (g/cc) |
|---|---|---|---|---|---|---|---|---|
| C-3a | Three | 46.32 | | 30.79 | | 0.866 | | 0.8667 |
| 1a | One | 74.73 | | 63.39 | | 0.884 | | 0.8710 |
| 1b | One | 74.33 | | 63.79 | | 0.884 | | 0.8700 |
| 1c | One | 77.99 | | 65.93 | | 0.886 | | 0.8703 |
| 2a | Two | 24.26 | 91.19 | 10.33 | 67.53 | 0.854 | 0.897 | 0.8606 |
| 2b | Two | 26.85 | 91.19 | 11.66 | 67.59 | 0.855 | 0.897 | 0.8612 |
| 2c | Two | 26.86 | 91.73 | 11.79 | 67.39 | 0.855 | 0.898 | 0.8612 |
| 2d | Two | 29.06 | 91.79 | 13 | 67.6 | 0.856 | 0.898 | 0.8615 |
| C-3b | Three | 61.92 | | 49.8 | | 0.875 | | 0.8712 |
| C-2a* | Two | 41.07 | 91.86 | 24.11 | 75.48 | 0.863 | 0.898 | 0.8635 |

Figure 1A:
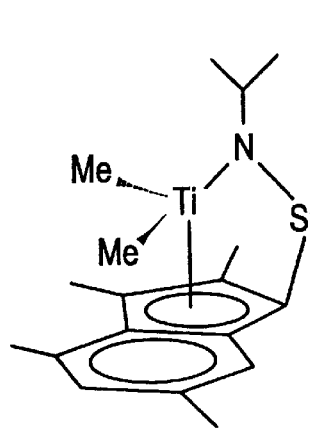
FIG. 1 is an illustration of catalysts, cocatalysts, and scavenging compounds practiced in the examples set forth herein.
Figure 1B:
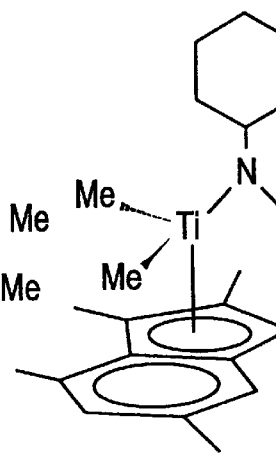
Figure 1C:
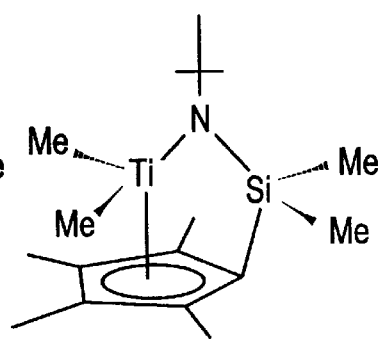
Figure 2:
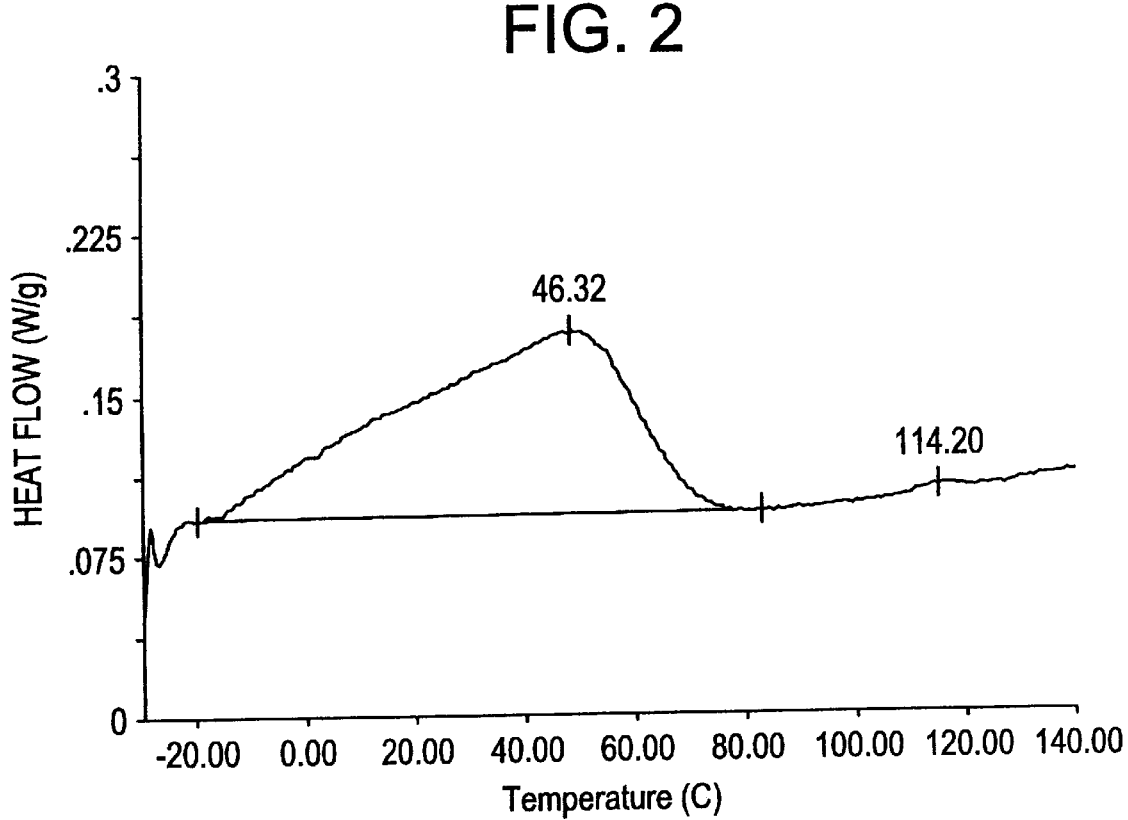
FIG. 2 is a DSC endogram of an ethylene/octene interolymer of a Comparative Example C-3a prepared using Catalyst Three.
Figure 3:
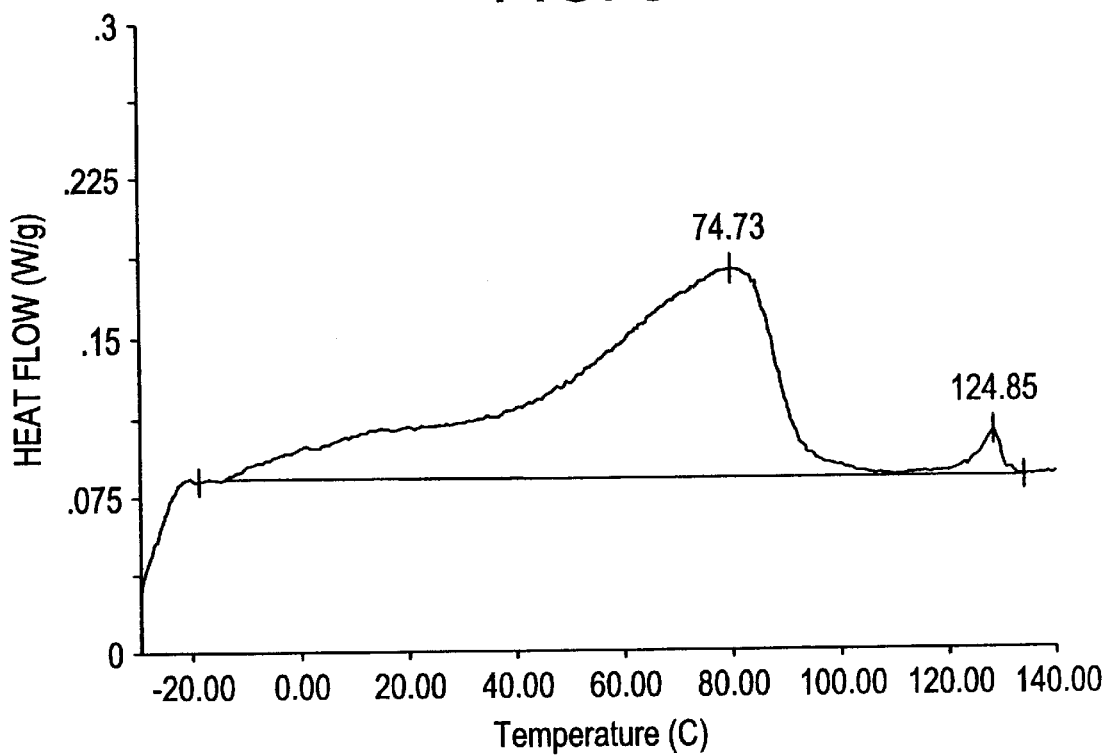
FIG. 3 is a DSC endogram of the ethylene/octene interpolymer of Example 1a prepared using Catalyst One.

Given the overall ASTM densities of the copolymers produced using Catalysts One and Two, the melting points (Tm's) and crystallization points (Tc's) were very different from those of the copolymers of the Comparative Examples prepared using Catalyst Three. This distinction is further exemplified in the DSC endograms of copolymers C-3a (Catalyst Three) and 1a (Catalyst One) are shown in FIGS. 2 and 3.

First, the copolymers of the invention prepared with Catalyst One had a Tm which is at least 10° C. greater than that of the polymers of the Comparative Examples produced using Catalyst Three, which is expected to translate to an enhanced upper service temperature. Such higher upper service temperatures are clearly demonstrated by the dynamic mechanical data discussed below.

Figure 4:
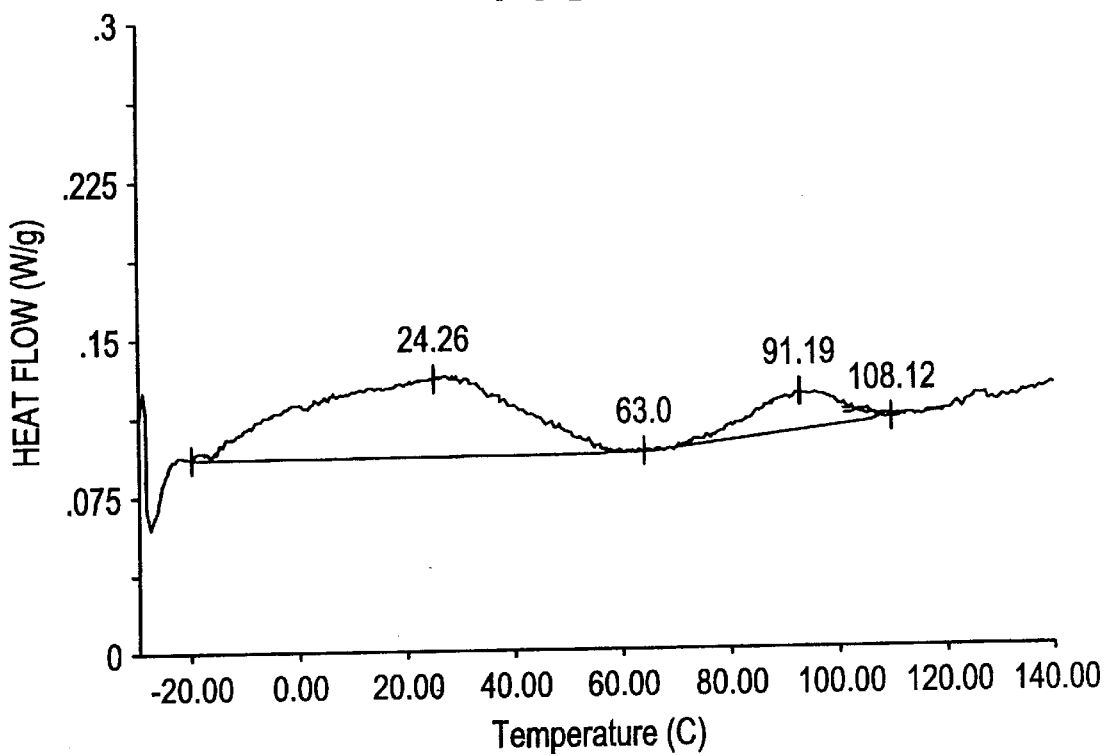
FIG. 4 is a DSC endogram of the ethylene/octene interpolymer of Example 2a prepared using Catalyst Two.

Moreover, as shown FIG. 4 and Table Three, the DSC thermograms of copolymers produced using Catalyst Two have a distinct bimodal character. In fact, the DSC thermogram for such polymer of Example 1a corresponds to a DSC thermogram of a blend of two copolymers having densities of 0.855 and 0.897 g/cm³, respectively.

Figure 5:
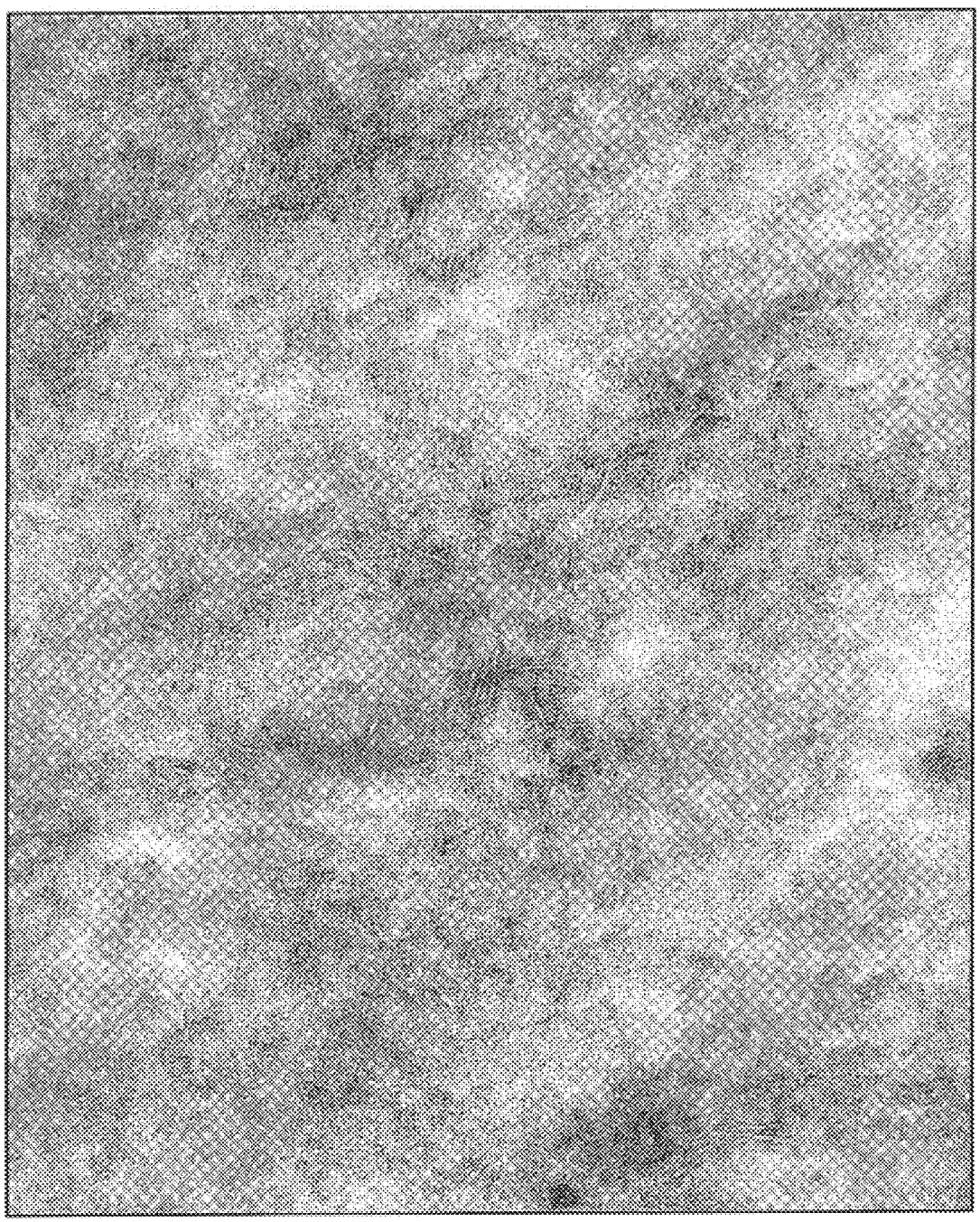
FIG. 5 is a transmission electron micrograph of the ethylene/octene interpolymer of Example 2a prepared using Catalyst Two.
Figure 6:
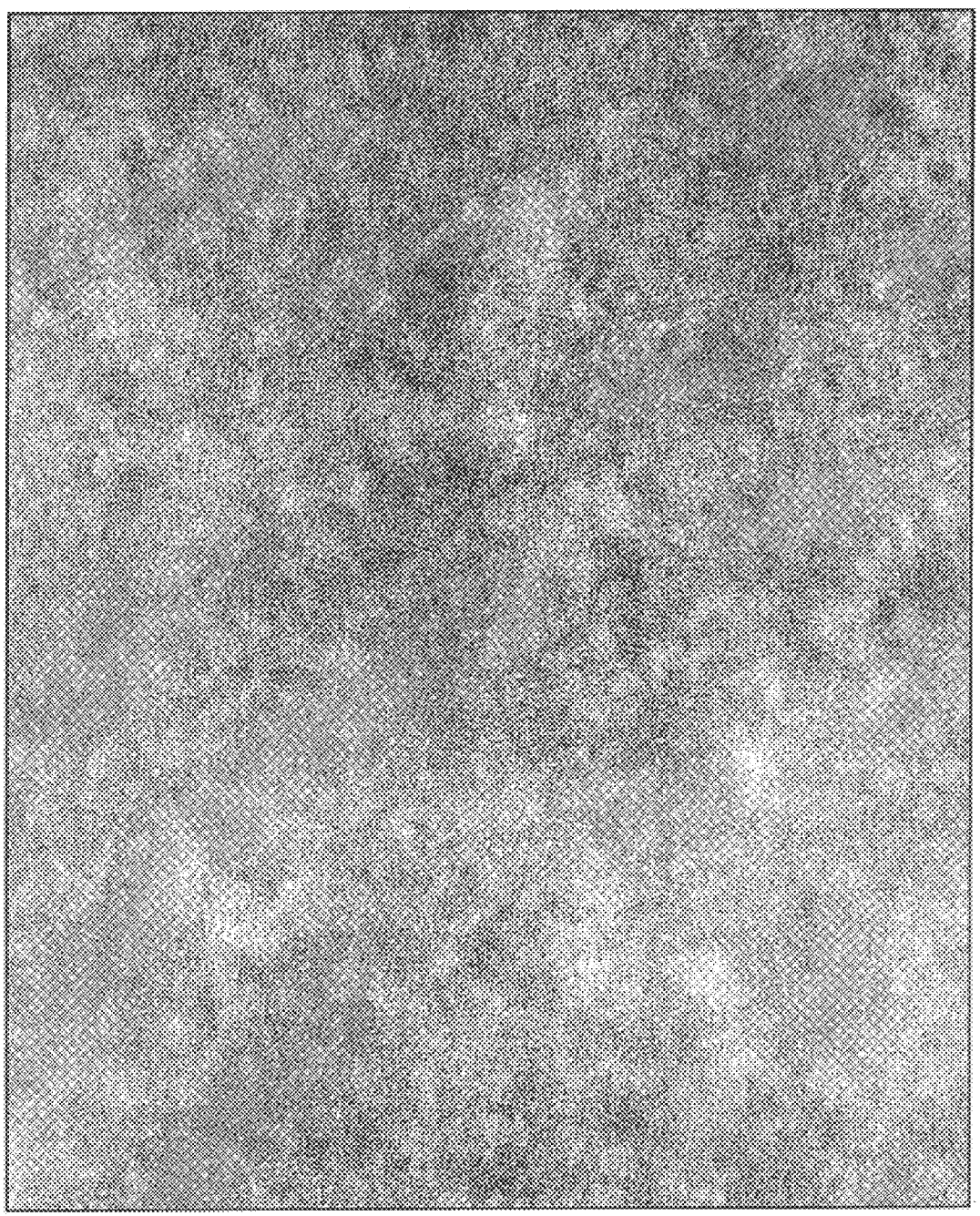
FIG. 6 is a transmission electron micrograph of the ethylene/octene interpolymer of Comparative Example C-3a prepared using Catalyst Three.

The bimodal characteristic of the polymers of the invention prepared using Catalyst Two is further exemplified in a micrograph of polymer 2a produced by transmission electron microscopy (TEM), wherein one can clearly see the lamellae produced by the higher density copolymer fraction. For example, as shown in FIG. 5, well defined lamella were present in the polymer of Example 2a. These ribbon-like structures, with an aspect ratio of about 16 (1120 Å×70 Å), appear relatively isolated in a matrix of granule-like fringed micelle structures, with an aspect ratio close to unity (70 Å). In contrast, well defined lamellae were not present in TEM micrograph prepared for the copolymer of Comparative Example C-3a prepared using Catalyst Three, as shown in FIG. 6 (although it did have some structures having an aspect ratio of about 6). The lack of lamellae existed despite the fact that the copolymer of Comparative Example C-3a had a higher density that that of the copolymer of Example 2a.

Assuming that octene is randomly incorporated into the copolymers of the invention and comparative examples, one can calculate the final density in accordance with the following equation:

$$1/\rho_r = w_1/\rho_1 + w_2/\rho_2$$

wherein $\rho_r$ is the final density, $\rho_1$ and $\rho_2$ are the densities of the first and second component fractions, respectively, and $w_1$ and $w_2$ are the weight fractions of the component fractions.

The polymers of Examples 1b and 2a and Comparative Examples C-3a and C-2a* were analyzed for short chain branching distribution by ATREF. The results are set forth in the following Table Four:

TABLE 4

Measurement of Comonomer Incorporation by ATREF

| | | ATREF | | | Calculated | | |
|---|---|---|---|---|---|---|---|
| Example | Catalyst | % Purge | Elution Temp. (° C.) | Calc'd Density (g/cc) | Tm1 Density (g/cc) | Tm2 Density (g/cc) | ASTM Annealed Density (g/cc) |
| C-3a | Three | 100 | | | 0.866 | | 0.8667 |
| 1b | One | 63.8 | 53.00 | 0.8855 | 0.884 | | 0.8700 |
| 2a | Two | 92.3 | 62.45 | 0.8950 | 0.854 | 0.897 | 0.8606 |
| C-2a* | Two | 90.1 | 60.85 | 0.8934 | 0.863 | 0.898 | 0.8635 |

*Comparative Example C-2a was produced in a batch reactor.

Figure 7A:
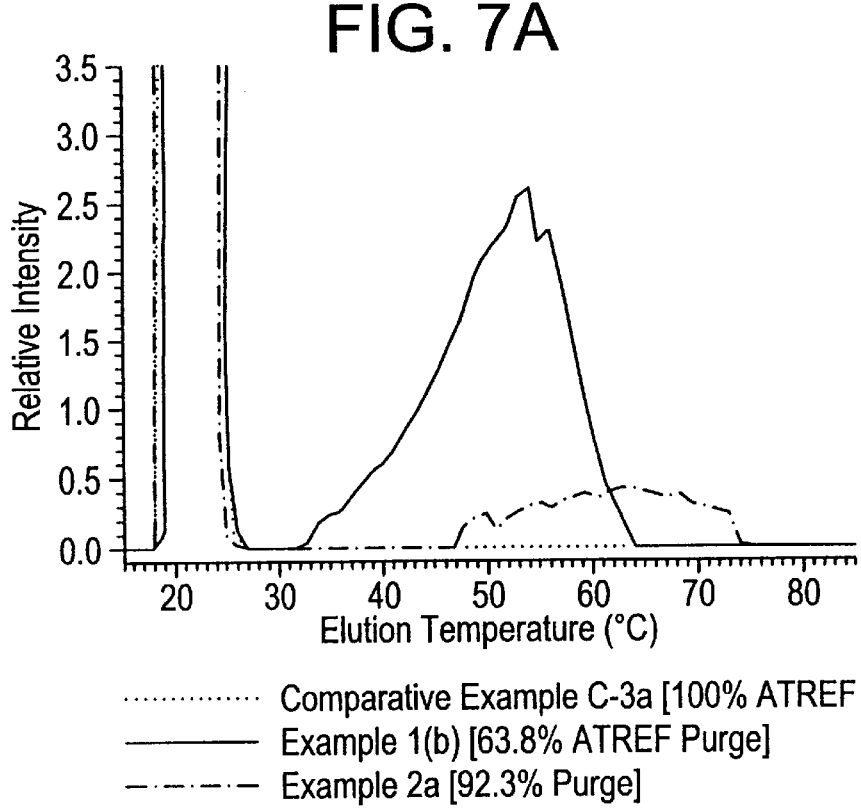
FIG. 7a are ATREF curves of an ethylene/octene interpolymer prepared with Catalyst One (Example 1b) and Catalyst Two (Example 2a)s, respectively, and of the ethylene/octene Interpolymer of Comparative Example C-3a prepared with Catalyst Three.
Figure 7B:
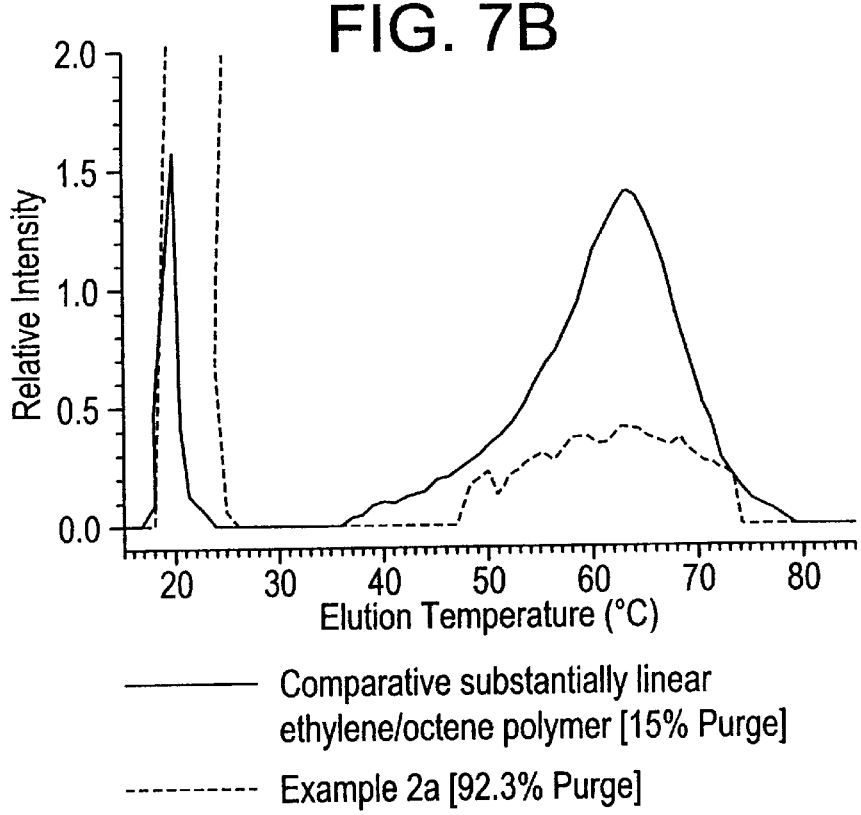
FIG. 7b are ATREF curves of an ethylene/octene interpolymer prepared with Catalyst Two, and of a comparative ethylene/octene interpolymer having a density of 0.895 g/cm³ and a melt index ($I_2$) of 1.6 g/10 minutes prepared with Catalyst Three.

The ATREF curves for Examples 1b and 2a and for Comparative Example C-3a are set forth in FIG. 7a. Because the overall densities of these copolymers were relatively low, most of the copolymer eluted with the purge, i.e., the copolymer did not crystallize from the solvent (trichlorobenzene). In fact, 100 percent of the copolymer of Comparative Example C-3a eluted with the purge. The ATREF data showed that both Catalysts One and Two produced copolymers which were bimodal in short chain branching distribution. More specifically, the bulk of the copolymer produced from these catalysts was a low density copolymer which eluted with the purge, but there was also a higher density copolymer which produced a peak in the ATREF chromatograms shown in FIG. 7a. Comparing the copolymers of Catalyst One with that of Catalyst Two, Catalyst Two produced a smaller amount of the higher density copolymer. As shown in Table Four, the copolymer densities calculated from ATREF were similar to the DSC estimate. For example, although the copolymer of Example 2a had a density of 0.861 g/cm³, the ATREF peak corresponded to what one would typically see for a substantially linear ethylene/1-octene copolymer prepared using Catalyst Three and having a density of 0.895 g/cm³. This is consistent with the finding above that the copolymer of Example 1a, having a density of 0.871 g/cm³ exhibited a DSC endotherm which corresponded to what one would typically see for a substantially linear ethylene/1-octene copolymer prepared using Catalyst Three having a density of 0.897 g/cm³. See, for example, FIG. 7b, which compares the ATREF of a copolymer produced with Catalyst Three having a density of 0.895 g/cm³, and $I_2$ of 1.6 g/10 min. and an $I_{10}/I_2$ of 9.9 with the copolymer of Example 2a.

Similarly, although the copolymer of Example 1b had a density of 0.870 g/cm³, the ATREF peak corresponded to what one would typically see for a substantially linear ethylene/1-octene copolymer prepared using Catalyst Three and having a density of 0.886 g/cm³, which is consistent with the finding above that the copolymer of Example 1b exhibited a DSC endotherm which corresponded to what one would typically see for a substantially linear ethylene/1-octene copolymer prepared using Catalyst Three having a density of 0.884 g/cm³.

Figure 7C:
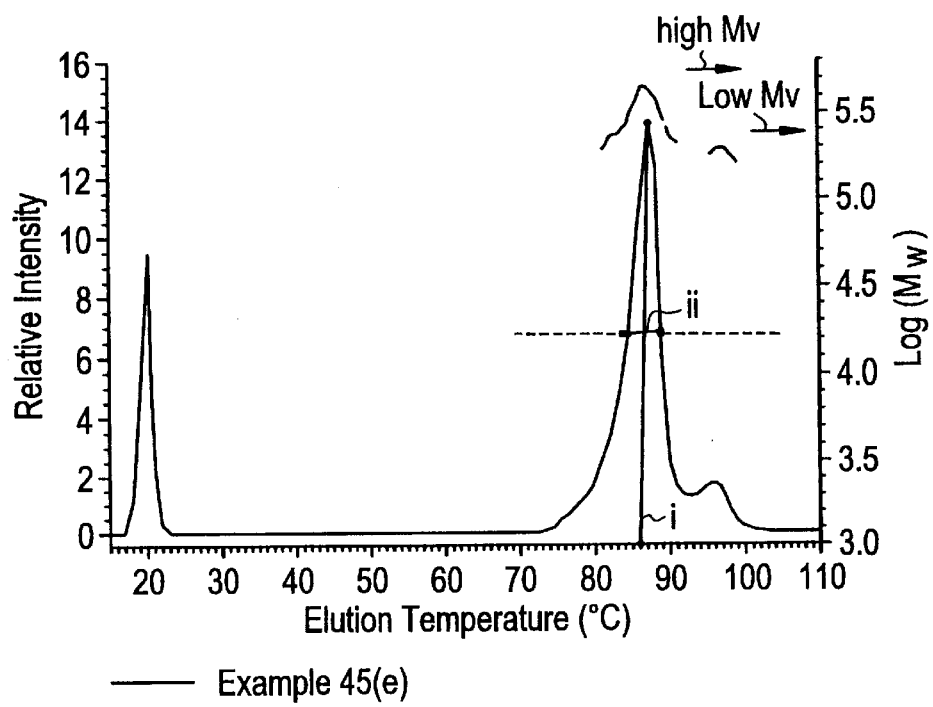
FIG. 7c are ATREF and differential viscosity curves of the ethylene/octene interpolymer of Example 45(e) prepared with Catalyst Two.

ATREF/DV may be further used to illustrate the fact that the copolymers of the invention are characterized as having a bimodal molecular weight distribution. For instance, as set forth in FIG. 7c, the ATREF refractive index detector shows the unique short chain branching distribution of the copolymer of Example 45e produced by Catalyst Two. In addition, the ATREF differential viscometer detector (right hand verticle axis) shows that the copolymer comprises 92 weight percent of a lower density component which elutes at about 71° C. and has a weight average molecular weight of 417000 daltons, and about 8 weight percent of a higher density component which elutes at about 85° C. and has a weight average molecular weight of 174000 daltons. Thus the ATREF $M_{w1}M_{n2}$ ratio was 2.40, which was similar to the value determined by GPC deconvolution, shown in Table Six, i.e., 2.41.

Figure 7D:
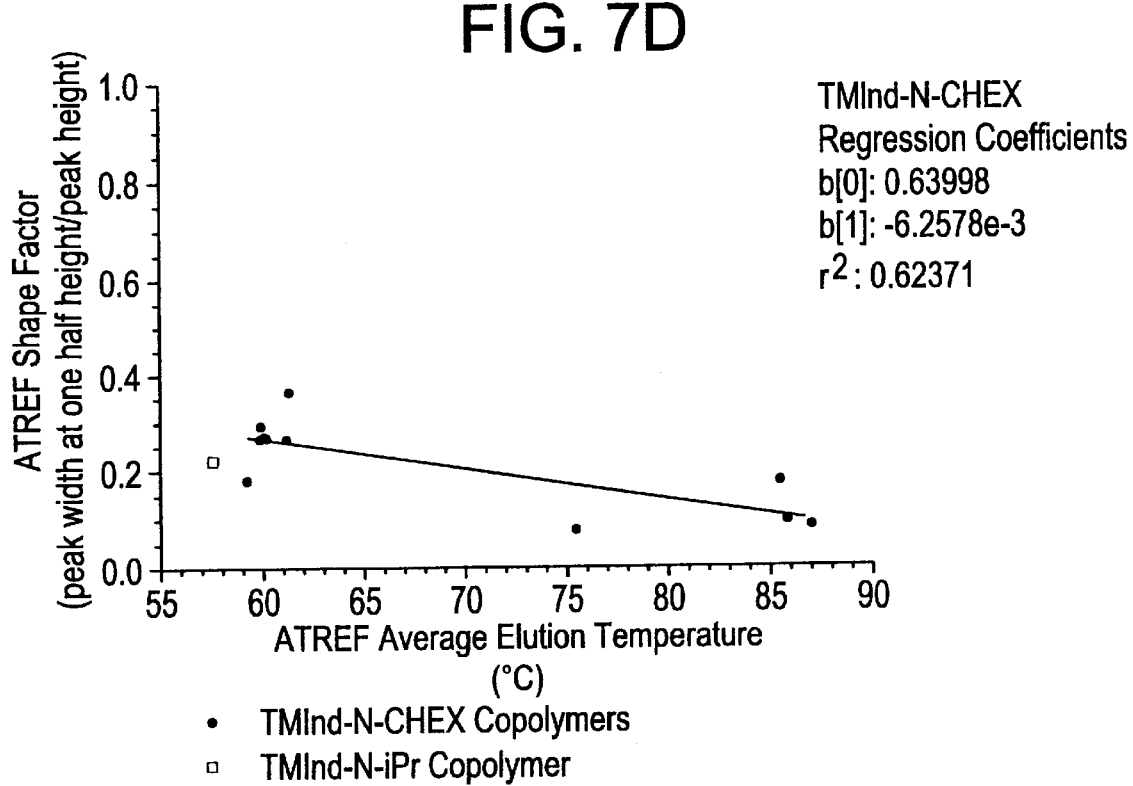
FIG. 7d is a plot of the Atref shape factor versus the average ATREF elution temperature.

The following FIG. 7d is a plot of the ATREF shape factor versus the average ATREF elution temperature. This data in this plot was generated from ATREF curves. Specifically, (i) the maximum ATREF peak height was measured, (ii) the width of the total ATREF peak at ½ the maximum peak height was measured, the ATREF shape factor was calculated, i.e., the ratio (ii)/(i), and the average ATREF elution temperature was determined, i.e., (minimum ATREF elution temp+maximum ATREF elution temp)/2. In the case of the copolymers of the invention produced with Catalyst Two, the ATREF shape factor was described by the line ATREP shape factor=0.64−0.00626 (average ATREF elution temperature), which indicates an ATREF shape factor of 0.165 at an average elution temperature of 75.94° C.

The polymers of the invention will be characterized as having an ATREF curve which satisfies the, following inequality:

ATREF Shape Factor≦0.90−0.00626 (Average Elution Temperature)

which preferably satisfies the following inequality:

ATREF Shape Factor≦0.75−0.00626 (Average Elution Temperature).

and which most preferably satisfies the following inequality:

ATREF Shape Factor≦0.70−0.00626 (Average Elution Temperature).

As the above DSC and ATREF information illustrates, the polymer compositions of the invention are characterized as having a fraction which has a higher crystallinity than the other fraction. The presence of the higher crystallinity fraction translates to an enhancement in the upper service temperature of the polymer compositions of the invention, with respect to the comparative compositions prepared with Catalyst Three. In particular, dynamic mechanical data for the copolymers of Examples 1a and 2a, and for Comparative Example C-3c are compared in FIG. 8. FIG. 8a compares the storage modulus (G') and tan d (G"/G') as a function of temperature. At high temperatures, the copolymers of Examples 1a and 2a, produced with Catalyst One and Two, respectively, were more elastic, relative to the copolymer of Comparative Example C-3c, produced with Catalyst Three. Higher elasticity is a desirable attribute in applications such as thermoforming. The upper service temperature may be defined as the intersection of a line drawn across the upper non-melted plateau region and the descending melting transition region of the log G1 versus. temperature plot, as indicated by the intersecting dashed lines on FIG. 8b. The upper service temperature of the copolymer of Example 1a was 75° C., which was 21° C. higher that of the Comparative Example C-3a which had an upper service temperature of 54° C. The upper service temperatures of the copolymer of Example 2a was 76° C., which was about 22° C. higher than that of the copolymer of Comparative Example C-3c, which was especially surprising in view of the fact that the copolymer of Example 2a had a lower density than that of copolymer C-3c.

Moreover, it is important to note that the enhancement in upper service temperature exceeds that which is achieved by blending discreet substantially linear ethylene/1-octene copolymers having densities corresponding to each of the fractions of the copolymers of the invention. FIG. 9a compares the upper service temperatures of the copolymers produced using Catalyst Two with copolymers produced using Catalyst Three, as a function of density. The curves in FIG. 9a were simple polynomial fits through the data. The copolymers prepared with Catalyst Two which are used in FIG. 9a include Example 2a, and examples prepared using a batch polymerization process set forth above utilizing Catalyst Two and the following reactor conditions:

| Example | Catalyst[1] (μmoles) | Octene (g) | Ethylene (g) | H2 (mmole) | Temp (° C.) | Efficiency | Melt Index I2 dg/min | Melt Flow Ratio I10/I2 | ASTM Density (g/cc) |
|---|---|---|---|---|---|---|---|---|---|
| 45a | 15 | 37.5 | 117 | 20 | 170 | 0.042 | 0.31 | 6.56 | 0.9131 |
| 45j | 7.5 | 253.7 | 132.7 | 5 | 155 | 0.168 | 1.36 | 6.94 | 0.8655 |
| 45n | 7.5 | 140.5 | 125 | 20 | 155 | 0.181 | 0.36 | 22.87 | 0.8823 |

[1](2,3,4,6-tetramethyl-indenyl)dimethyl(cyclohexylamido)silane titanium dimethyl For copolymers having a density of 0.87 g/cm³, the upper service temperature of copolymers produced using Catalyst Two was 33° C. higher than that of comparative polymers prepared using Catalyst Three.

FIG. 9b compares the increase in upper service temperature (UST) which can be achieved via blending copolymers prepared with Catalyst Three with the increase in UST achievable with the copolymers of the invention prepared with Catalyst Two. Studies show that approximately 20 wt % of the higher density component produced the maximum increase in UST in the case of blends. More specifically, when the blend comprised below 20 wt % of the higher density component, the UST decreased due to the decreasing concentration of the higher melting material, while when the blend comprised more than 20 wt % of the higher melting material, the UST decreased because it was necessary to decrease the density of the higher melting material (to keep the overall density of the blend constant at 0.875 g/cm$^3$). In sharp contrast with the behavior of blends, the copolymers of the invention exhibited unique behavior. For example, relative to a blend containing about 10 wt % of a higher density copolymer (which corresponds to the relative proportion of the high density component in the copolymer produced by Catalyst Two. As illustrated in FIG. 9a, the copolymer produced using Catalyst Two exhibited a 24° C. higher upper service temperature than the copolymer of the comparative blend.

The molecular weight ($M_w$ and $M_n$) and the polydispersity ($M_w/M_n$) for the copolymers of Examples 1a–1c, and 2a–2d, as well as for Comparative Examples C-3a and C-2a were determined, and are set forth in the following Table Five:

$$\ln(10)\frac{M_i}{M_n}\exp\left(\left(-\frac{M_i(1+\zeta)}{M_n}\right)\right)\times\left(\frac{2+\zeta}{\zeta}\right)^{1/2}\times I_1\left(\frac{M_i\zeta^{1/2}(2+\zeta)^{1/2}}{M_n}\right)$$

where $I_1(x)$ is the modified Bessel function of the first kind of order one, defined by $$I_1(x) = \sum_b \frac{x^{2b+1}}{2^{2b+1}b!(b+1)!} \quad [3]$$

and $\zeta$ is an adjustable parameter which broadens the molecular weight distribution, as shown in Eq.[4].

$$\frac{M_w}{M_n} = 2+\zeta \quad [4]$$

As defined by Bamford and Tompa, $\zeta$ is related to the level of long chain branching via, $$LCB/10000C = \frac{10000M\zeta}{M_n} \quad [5]$$

where M is the average molecular weight of the repeating unit. The b individual terms of the expanded Bessel function represent the molecular weight distributions of the polymer chains carrying b long chain branches per molecule. Bam- TABLE Five

| | | Gel permeation chromatography (GPC) data | | | | | |
|---|---|---|---|---|---|---|---|
| | | GPC | | | Fit | | |
| Example | Catalyst | $M_w$ | $M_n$ | $M_w/M_n$ | $M_w$ | $M_n$ | $M_2/M_n$ |
| C-3a | Three | 146500 | 68700 | 2.132 | 142748 | 60643 | 2.354 |
| 1a | One | 122400 | 43100 | 2.840 | 121075 | 43348 | 2.793 |
| 1b | One | 132500 | 52900 | 2.505 | 127299 | 47828 | 2.662 |
| 1c | One | 125300 | 51100 | 2.452 | 119533 | 44934 | 2.660 |
| 2a | Two | 143400 | 65400 | 2.193 | 139869 | 56994 | 2.454 |
| 2b | Two | 136300 | 54100 | 2.519 | 136096 | 53206 | 2.558 |
| 2c | Two | 142900 | 64300 | 2.222 | 138895 | 55961 | 2.482 |
| 2d | Two | 146200 | 62400 | 2.343 | 143378 | 57570 | 2.491 |
| C-3b | Three | 37300 | 17000 | 2.194 | 36878 | 15846 | 2.327 |
| C-2a* | Two | 159700 | 77000 | 2.074 | 155539 | 67900 | 2.291 |

*Comparative Example C-2a was produced in a batch reactor.

As illustrated in Table Five, the copolymers of the Comparative Examples C-3a and C-3b had GPC polydispersities ($M_w/M_n$'s) of 2.16, while copolymers produced with Catalysts One and Two had polydispersities of 2.60 (Catalyst One) and 2.32 (Catalyst Two).

The raw GPC chromatograms were also fit to the Bamford-Tompa distribution from which one can calculate an overall $M_n$, $M_w$ and $M_w/M_n$. This fitting procedure assumed a unimodal molecular weight distribution where the level of long chain branching was varied to fit raw GPC chromatograms.

The Bamford-Tompa molecular weight distribution is calculated via Eq.[2], $$w_i(M_i) = \quad [2]$$

ford and Tompa also provide equations to calculate the average number of branch points in a molecule as a function of chain length. See, e.g. ,C. H. Bamford and H. Tompa "The Calculation of Molecular Weight Distributions from Kinetic Schemes" Trans. Faraday Soc., 50, 1097(1954).

The "fit" $M_w/M_n$'s provided a more consistent polydispersity estimate. The "fit" polydispersities for the copolymers of Comparative Examples C-3a and C-3b, Examples 1a–1C and Examples 2a –2d, were 2.34, 2.50 and 2.71, respectively.

In the case of the copolymers of Examples 2a–2d, which were produced in a continuous solution polymerization process and Comparative Example C-2a, which was produced in a batch solution polymerization process, the former have an increased polydispersity over the lafter. In particular, Comparative Example C-2a exhibited a polydispersity of 2.07, while Examples 2a–2d exhibited a mean polydispersity of 2.32±0.15; similarly, "fit" polydispersities of 2.29 and 2.50±0.04, respectively, were observed for copolymers of Comparative Example C-2a and Examples 2a–2d, respectively.

The increased polydispersity, as one moves from the batch to the continuous process, correlates with the increase in melt flow ratio. For example, the average $I_{10}/I_2$ of the copolymers of Examples 2a–2d was 13.3, while the copolymer of Comparative Example C-2a exhibited an $I_{10}/I_2$ of 6.5. Both of these observations, i.e., the higher $M_w/M_n$ and $I_{10}/I_2$, suggest that the continuous process copolymers contained a higher concentration of long chain branches than the corresponding batch polymerized polymers. It is well known that long chain branching dramatically increases the shear thinning behavior of a copolymer.

were determined following a visual inspection of the experimental GPC chromatogram. Converged parameter estimates were remarkably insensitive to the initial parameter values.

Assuming that the copolymers produced by the Catalysts One and Two were bimodal in molecular weight distribution, Table Six summarizes GPC deconvolution results. In this procedure, as described above, the molecular weight distributions of the two components were assumed to follow a Bamford-Tompa distribution. Thus, GPC deconvolution involved a five parameter fit; $M_{n1}, \zeta_1, M_{n2}, \zeta_2$, and the weight fraction of the higher molecular weight copolymer ($M_{n1}$). The GPC deconvolution data are set forth in the following Table Six:

TABLE Six

GPC deconvolution results for the ethylene/octene copolymers produced using Catalysts One and Two

| Example | Catalyst | High Mw Low Density Component | | | | Low Mn High Density Component | | | Mn Ratio |
| --- | --- | --- | --- | --- | --- | --- | --- | --- | --- |
| | | Mw1 | Mn1 | Mw/Mn | wt % | Mw2 | Mn2 | Mw/Mn | Mn1/Mn2 |
| 1a | One | 165383 | 72285 | 2.2879 | 62.6 | 56827 | 28272 | 2.0100 | 2.56 |
| 1b | One | 176274 | 78776 | 2.2377 | 60.0 | 64304 | 32152 | 2.0000 | 2.45 |
| 1c | One | 166456 | 72573 | 2.2936 | 60.3 | 61713 | 30855 | 2.0001 | 2.35 |
| Average TMInd-N-iPr → | | 169371 | 74545 | 2.2731 | 61.0 | 60948 | 30426 | 2.0034 | 2.45 |
| 2a | Two | 155074 | 65311 | 2.3744 | 84.1 | 79312 | 39654 | 2.0001 | 1.65 |
| 2b | Two | 155959 | 65455 | 2.3827 | 81.5 | 62924 | 31459 | 2.0002 | 2.08 |
| 2c | Two | 155235 | 65205 | 2.3807 | 83.0 | 76699 | 38348 | 2.0001 | 1.70 |
| 2d | Two | 168193 | 73727 | 2.2813 | 77.1 | 67357 | 33678 | 2.0000 | 2.19 |
| Average TMInd-N-CHEX → | | 158615 | 67425 | 2.3548 | 81.4 | 71573 | 35785 | 2.0001 | 1.88 |
| 5r[1] | Two | 296460 | 68670 | 2.3172 | 95.5 | 95134 | 47558 | 2.0004 | 1.44 |
| 10a[1,2] | TMCp-N-CHEX | 77124 | 36015 | 2.1414 | 85.5 | 48108 | 24054 | 2.0000 | 1.50 |
| 10c[1,2] | 2-Me-5,6,5-Ind-N-CHEX | 164432 | 71648 | 2.2950 | 84.2 | 60634 | 30316 | 2.0001 | 2.36 |
| 10e[1,2] | 3-Pyrol-Inc-N-CHEX | 258038 | 114543 | 2.2528 | 89.1 | 142678 | 71339 | 2.0000 | 1.61 |
| 10j[1,2] | One | 220854 | 98430 | 2.2438 | 68.5 | 105325 | 52662 | 2.0000 | 1.87 |
| 45e[1,3] | Two | 321517 | 143333 | 2.2432 | 89.7 | 118855 | 59424 | 2.0001 | 2.41 |
| 45f[1,3] | Two | 133488 | 58611 | 2.2775 | 86.6 | 64027 | 32009 | 2.0003 | 1.83 |
| 45h[1,3] | Two | 121666 | 53434 | 2.2769 | 89.6 | 57857 | 28926 | 2.0002 | 1.85 |
| 45i[1,3] | Two | 72715 | 32997 | 2.2037 | 98.9 | 39552 | 19776 | 2.0000 | 1.67 |

[1]Batch reactor

Deconvolution of Bimodal Molecular Weight Distributions

The molecular weight distributions of copolymers produced by Catalyst One and Two were assumed bimodal. In addition it was assumed the $M_w/M_n$ of each component could be described by Eq.[2]. Thus, the GPC deconvolution procedure involved a five parameter fit, i.e., $M_{n1}, z_1, M_{n2}, z_2$ and split (S); where the subscripts 1 and 2 refer to the primary and secondary copolymer components, respectively, and split was defined as the weight fraction of the higher molecular weight copolymer. The non-linear curve-fitting subroutine within SigmaPlot+(v2.01) was used to estimate the parameters, This subroutine used the Marquardt-Levenberg algorithm to determine parameter values that minimized the sum of squares of differences between the distribution defined by the dependent variable values and the observed GPC data. The non-linear curve fitting algorithm required initial parameter values, which As shown in Table Six, 61 percent of the copolymer produced by Catalyst One was of 169000 daltons, with the remainder 61000 daltons. Similarly, approximately 81.4% of the copolymer produced by Catalyst Two was of 159000 daltons, with the balance 72000 daltons. FIGS. 10 and 11 illustrate these deconvolution results in a graphical format. GPC deconvolution results for batch reactor samples were also summarized in Table Six.

The copolymers of this invention were analyzed for indicia of long chain branching. In particular, Theological data were generated using a Rheometrics RMS-800 dynamic mechanical spectrometer with 25 mm diameter parallel plates in the oscillatory shear mode. Frequency sweeps were performed over the shear rate range of 0.1–100 rad/s at 15% strain in a nitrogen atmosphere. Rheological data are set forth in the following Table Seven.

TABLE Seven

Viscosity data for Copolymers of the Invention and for Copolymers of the Comparative Examples

| Example | Catalyst | Melt Index (dg/ml) | Melt Flow Ratio $I_{10}/I_2$ | $h_1$ viscosity (poise) | | $h_{0.1Hz}/h_{100Hz}$ | tan δ at 0.1 Hz |
|---|---|---|---|---|---|---|---|
| | | | | $h_{0.1Hz}$ | $h_{100Hz}$ | | |
| C-3a | Three | 0.48 | 9.38 | 186030 | 20889 | 8.91 | 4.83 |
| 1a | One | 0.71 | 11.58 | 216860 | 15510 | 13.98 | 2.72 |
| 1b | One | 0.63 | 12.29 | 195830 | 14486 | 13.52 | 2.83 |
| 1c | One | 0.82 | 10.91 | 164620 | 14097 | 11.68 | 3.24 |
| 2a | Two | 0.5 | 15.22 | 293030 | 17363 | 16.88 | 2.37 |
| 2b | Two | 0.43 | 13.58 | 344890 | 18370 | 18.77 | 2.13 |
| 2c | Two | 0.38 | 14.39 | 346910 | 18053 | 19.22 | 2.10 |
| 2d | Two | 0.38 | 10.11 | 400840 | 18965 | 21.14 | 1.91 |
| C-3b | Three | 116 | 6.00 | 854 | 696 | 1.23 | 102.8[1] |
| C-2a* | Two | 0.49 | 6.53 | 171940 | 22021 | 7.81 | 6.06 |

[1] at 0.631 Hz (rather than 0.1 Hz)
[2] could not measure
*Copolymer C-2a was produced in a batch reactor.

FIG. 13 provides a plot of the log viscosity versus log frequency for the copolymers of in the invention and of the comparative examples as determined by RMS 800 rheometer in accordance with the procedure set forth above. As illustrated in FIG. 13, the copolymer of Examples 2a exhibited enhanced shear thinning behavior over the copolymer of Comparative Example C-2a, both of which were produced with Catalyst Two. In addition, FIG. 13 illustrates that the copolymer of Example 2a, prepared by a continuous process, was more elastic that the copolymer of Comparative Example C-2a, which was produced in a batch reactor, as indicated by the lower tan d value of the former. These behaviors are indicative of the higher level of long chain branching characteristic of copolymers produced in a continuous solution polymerization process.

The melt fracture behavior of selected resins were also evaluated on the gas extrusion rheometer (GER). The shear stress (MPa) and shear rate (s-1) values where each resin lost surface gloss (LSG) and at the onset of gross melt fracture (OGMF) are set forth in the following Table Eight:

As demonstrated by the shear rate at the onset of gross melt fracture (OGMF), the copolymers produced with Catalyst One and Two were more resistant to melt fracture than the copolymer of Comparative Example C-2a, which was produced using Catalyst Two in a continuous reactor. Since shear rate is directly proportional to output (e.g., lb/hr or parts/hr), the copolymer of Example 2a, prepared with Catalyst Two, can be processed at higher rates relative to copolymer C-3c, prepared with Catalyst Three.

The advantage in using a continuous solution polymerization process over a batch solution polymerization process is illustrated in a comparison of the copolymer of Example 2a, prepared in a continuous solution polymerization reaction, with that of Comparative Example C-2a, prepared in a batch solution polymerization reaction. Although the copolymers had a similar melt index, the copolymer of Comparative Example C-2a exhibited a lower OGMF shear rate (89 s$^{-1}$) than the copolymer of Example 2a (432 s$^{-1}$).

Infrared analysis (FTIR) was performed on representative copolymers of the Examples and of the Comparative TABLE Eight Gas extrusion rheometer (GER) data for Copolymers of the Examples and of the Comparative Examples

| Example | Catalyst | Density (g/cc) | Melt Index (dg/min) | Melt Flow Ratio I10/I2 | LSG[1] Shear Stress (MPa) | LSG[1] Shear Rate (s$^{-1}$) | OGMF[2] Shear Stress (MPa) | OGMF[2] Shear Rate (s$^{-1}$) |
|---|---|---|---|---|---|---|---|---|
| 2a | Two | 0.8606 | 0.50 | 15.22 | 0.151 | 56 | 0.302 | 432 |
| C-3c[3] | Three | 0.8680 | 0.51 | 8.01 | <0.086 | <24 | 0.237 | 280 |
| 1c | One | 0.8703 | 0.82 | 10.91 | <0.086 | <35 | 0.259 | 479 |
| C-2a | Two Batch Reactor | 0.8635 | 0.49 | 6.53 | 0.129 | 19 | 0.237 | 89 |

[1] LSG = loss of surface gloss
[2] OGMF = onset of gross melt fracture
[3] Substantially linear ethylene/1-octene interpolymer prepared with Catalyst Three in a continuous solution polymerization process
*Comparative Example C-2a was produced in a batch reactor Examples, the results of which is set forth in the following Table Nine:

TABLE Nine

Fourier transform infrared (FTIR) data for Copolymers of the Examples and of the Comparative Examples

| Example | Catalyst | Density (g/cc) | Melt Index (dg/min) | Melt Flow Ratio I10/I2 | Vinyls | Trans + Vinylidene | Vinyl Ratio[1] | Trans + Vinylidene Ratio |
|---|---|---|---|---|---|---|---|---|
| C-3a | Three | 0.8667 | 0.48 | 9.38 | 0.025 | 0.220 | 1.000 | 1.000 |
| 1a | One | 0.8710 | 0.71 | 11.58 | 0.042 | 0.293 | 1.680 | 1.332 |
| 1b | One | 0.8700 | 0.63 | 12.29 | 0.046 | 0.298 | 1.840 | 1.355 |
| 1c | One | 0.8703 | 0.82 | 10.91 | 0.080 | 0.320 | 3.200 | 1.455 |
| 2a | Two | 0.8606 | 0.50 | 15.22 | 0.052 | 0.602 | 2.080 | 2.736 |
| 2b | Two | 0.8612 | 0.43 | 13.58 | 0.037 | 0.580 | 1.480 | 2.636 |
| 2c | Two | 0.8612 | 0.38 | 14.39 | 0.051 | 0.556 | 2.040 | 2.527 |
| 2d | Two | 0.8615 | 0.38 | 10.11 | 0.043 | 0.566 | 1.720 | 2.573 |
| C-3b | Three | 0.8712 | 116 | 6.00 | 0.130 | 0.311 | 5.200 | 1.414 |

[1]normalized vinyl concentration (relative to the vinyl concentration of sample 4a)

The data set forth in Table Nine illustrates that the copolymers of Examples 1a–1c and 2a–2d exhibited higher vinyl concentrations than the copolymer of Comparative Examples C-3a. Given the higher level of vinyl termination characteristic of the copolymers of the invention, it is believed that they exhibit higher levels of long chain branching, due to the re-incorporation of vinyl-terminated macromolecules into propagating polymer chains. While not wishing to be bound by theory, it is believed that the higher levels of vinyl termination characteristic of the polymers of the invention are due to the higher reaction temperatures made possible by use of catalysts such as Catalysts One and Two described herein. For instance, a comparison of Comparative Examples C-3b and C-3a indicates that as the reaction temperature increases, the amount of vinyl termination likewise increases. It is noted that the copolymers of the Examples were produced at reaction temperatures of about 120° C., as compared to 80° C. for the copolymer of Comparative Example C-3a.

Copolymers of the Examples and Comparative Examples were further tested for compression set in accordance with the following procedure. Compression set buttons were prepared for each sample by cutting 2.86 cm diameter (1.125-in.) disks from 1.52 mm thick compression molded plaques. Disks were stacked (total stack height approximately 1.37 cm (0.54-in.)) in a compression set mold (at room temperature) and the disks were fused at 176.7° C. (350° F.) and 10,000 psi (69 MPa) over 10 minutes. The buttons were removed from the mold, equilibrated at ASTM conditions for 24 hours, and the thickness of each button was measured with a micrometer. The 1.27 cm thick (0.5-in.) buttons were placed in a compression set clamp and compressed to 0.953 cm (0.375-in.) by tightening the nuts until the top platten made contact with the 0.953 cm spacers. The cold compression set clamp was placed in an oven at 70° C. (158° F.) for 24 hours. The buttons were removed from the compression set clamp and equilibrated at ASTM conditions for 24 hours prior to the measurement of button thickness. Compression set was expressed as the percentage of the deformation which was not recovered. Additional information on the compression set test can be found in ASTM D-395-89 method B.

The compression set of copolymers of the invention produced with Catalyst One and Catalyst Two, and a comparative copolymer produced with Catalyst Three are summarized in FIG. 14. Relative to the copolymer C-3c produced with Catalyst Three, the compression set at 70° C. was lower for copolymers produced by Catalyst One and Catalyst Two, inspite of the similar crystallinity of the copolymers. Lower compression sets are desirable, in that, compression set represents the percentage of the deformation which was not recovered. Ideally, the compression set of perfect elastomers would be 0%, i.e., the deformation would be completely recovered. The lower compression set of the copolymers of the invention produced via Catalyst One and Catalyst Two was attributed to the bimodal short chain branching distribution.

Polymerization of Ethylene/Propylene Interpolymers and Ethylene/Propylene/Diene Interopolymers Ethylene/propylene interpolymers are prepared in accordance with the following procedure utilizing the reactor conditions set forth in the following Table.

Terpolymerization of ethylene, propylene, and ethylidene norbornene was carried out using a 3.8 L stainless steel reactor charged with 1450 Isopar E* (mixed alkanes, available from Exxon Chemicals, Inc.), 207.3 g of propylene, 17.6 g of ethylidene norbornene, and 13.8 mmol of hydrogen. The reactor was heated to 100° C. and then saturated with ethylene to 460 psig (3.2 MPa). The catalyst was prepared in a dry box by springing together 5.0 micromol (0.005 M solution) of the metal complex (isopropylamido) dimethyl(π5-2,3,4,6-tetramethylindenyl)silanetitanium (IV) dimethyl, 5 micromol (0.0075 M solution) of the cocatalyst di(hydrogenated-tallowalkyl)methylammonium tetrakis (pentafluorophenyl)borate, 50.0 micromol (0.050 M solution) of the scavenger (diisopropylamido) diethylaluminum, and additional Isopar E* to give a total volume of 18 mL. The catalyst solution was then transferred via syringe to a catalyst addition loop and injected into the reactor over approximately 4 minutes using a flow of high pressure solvent. The polymerization was allowed to proceed for 10 minutes while feeding ethylene on demand to maintain a pressure of 460 psig. The amount of ethylene consumed during the reaction was monitored using a mass flow meter. The polymer solution was then poured from the reactor into a nitrogen-purged glass kettle and stabilizer (Irganox 1076) were added and mixed well with the solution. The polymer solution was poured into a tray, air dried overnight, then thoroughly dried in a vacuum oven for one day. The yield of polymer was 37.0 g, and the catalyst efficiency calculated as grams of polymer per gram of transition metal was 0.15 million. The obtained terpolymer had a composition of 54.7 wt percent ethylene, 42.7 wt percent propylene, 2.6 wt percent ethylidene norbornene. The molecular weight was 147,200 with a molecular weight distribution of 2.18. The elastomer had a measured glass transition temperature of −53.90° C. and was 0.9 percent crystalline.

Using the apparatus and procedure above, with the exception of omitting the addition of ethylidene norbornene, sixteen ethylene/propylene copolymers are prepared using the ingredient amounts shown in Table below. The polymer physical properties are shown in the subsequent table. The catalyst of Examples 1a–1e is (cyclohexylamido)dimethyl($\pi$5-2,3,4,6-tetramethylindenyl)silanetitanium (IV) dimethyl. The catalyst of Examples 2a–2f is (isopropylamido)dimethyl($\pi$5-2,3,4,6-tetramethylindenyl)silanetitanium (IV) dimethyl. The catalyst of the comparative examples is is (tetramethylcyclopentadienyl)dimethyl(t-butylamido)silanetitanium 1,3-pentadiene. The cocatalyst of all Examples is di(hydrogenated-tallowalkyl)methylammonium tetrakis(pentafluorophenyl)borate. The scavenger of all Examples is a derivative of diisobutyl aluminum.

| Example No. | Ti µmole | Co-cat µmole | Al/Ti Ratio | Temp, C. | Exotherm, C. | C3 grams loaded | IPE mass | H2 delta P |
|---|---|---|---|---|---|---|---|---|
| Comp. EP 3a | 1.5 | 2.25 | 10 | 100 | 1.6 | 357 | 1462.9 | 30 |
| EP 2a | 1.25 | 1.88 | 10 | 70 | 0.6 | 355 | 1482 | 40.2 |
| EP 2b | 1.25 | 1.88 | 10 | 80 | 0.6 | 331 | 1475.9 | 40.4 |
| EP 2c | 1.5 | 2.25 | 10 | 90 | 1.1 | 376 | 1446.4 | 30 |
| EP 2d | 1.25 | 1.88 | 10 | 90 | 2 | 306 | 1441.2 | 40.7 |
| EP 2e | 1.5 | 2.25 | 10 | 100 | 2 | 280 | 1441 | 40.7 |
| EP 2f | 1.5 | 1.5 | 25 | 100 | 0.6 | 135.3 | 1461 | 292 |
| Comp. EP 3b | 1 | 1.5 | 10 | 100 | 7 | 303 | 1441.6 | 30.8 |
| Comp. EP 3c | 1.25 | 1.88 | 10 | 100 | 1.2 | 356 | 1449.5 | 41.2 |
| Comp. EP 3d | 1.25 | 1.88 | 10 | 90 | 1.6 | 376 | 1451.5 | 40.4 |
| Comp. EP 3e | 1.5 | 2.25 | 10 | 80 | 1.6 | 389 | 1451.1 | 40.4 |
| Comp. EP 3f | 1.5 | 2.25 | 10 | 70 | 3.4 | 407 | 1443 | 45.3 |
| Comp. EP 3g | 1 | 1.5 | 10 | 100 | 0.9 | 305 | 1454.2 | 30.3 |
| EP 1a | 1 | 1.5 | 10 | 100 | 1.3 | 306 | 1457.8 | 40.7 |
| EP 1b | 1 | 1.5 | 10 | 90 | 1.5 | 325.1 | 1455.2 | 40.2 |
| EP 1c | 1.5 | 2.25 | 10 | 80 | 2.8 | 340.6 | 1430.9 | 40.7 |
| EP 1d | 1.5 | 2.25 | 10 | 70 | 2.5 | 356.6 | 1436.3 | 50.9 |
| EP 1e | 2.5 | 2.5 | 25 | 100 | 0.5 | 137 | 1450.4 | 291 |

| Example No. | H2 mmol | C2 load, grams | C2 partial pressure | Length of Run, Min | C2 Consumed, g | Total Pressure, psig | Dry Weight, g | Efficiency MM g polymer/g · Ti |
|---|---|---|---|---|---|---|---|---|
| Comp. EP 3a | 2.7 | 128.3 | 250.9 | 10 | 100.3 | 467.2 | 227 | 3.16 |
| EP 2a | 3.6 | 222.5 | 320.2 | 13.6 | 30 | 463.2 | 43 | 0.72 |
| EP 2b | 3.7 | 186 | 302.5 | 12.1 | 45.1 | 461.9 | 75 | 1.25 |
| EP 2c | 2.7 | 152 | 265.5 | 5.2 | 45.5 | 464.8 | 113 | 1.57 |
| EP 2d | 3.7 | 159.8 | 293 | 5.1 | 45.3 | 464.7 | 88 | 1.47 |
| EP 2e | 3.7 | 141.6 | 286.2 | 3.9 | 45.5 | 463.5 | 94 | 1.31 |
| EP 2f | 27.6 | 153.6 | 351.5 | 10 | 37 | 458 | 59 | 1.2 |
| Comp. EP 3b | 2.82 | 133.8 | 271.6 | 10 | 90.4 | 463.3 | 266 | 5.55 |
| Comp. EP 3c | 3.8 | 125.5 | 253.9 | 6.8 | 55.2 | 463.5 | 102.2 | 1.71 |
| Comp. EP 3d | 3.68 | 147.53 | 269.3 | 5.3 | 50.4 | 462.6 | 123 | 2.05 |
| Comp. EP 3e | 3.7 | 174.5 | 275.3 | 4.5 | 42.3 | 462.7 | 112 | 1.56 |
| Comp. EP 3f | 4.1 | 215.1 | 305.9 | 3.6 | 32.3 | 464.7 | 131.5 | 1.83 |
| Comp. EP 3g | 2.8 | 130 | 273.9 | 10 | 79.2 | 465.1 | 147.4 | 3.08 |
| EP 1a | 3.76 | 133 | 274.2 | 7.8 | 55.2 | 464.1 | 104 | 2.17 |
| EP 1b | 3.7 | 155.44 | 287 | 8.1 | 55.2 | 464.3 | 99 | 2.07 |
| EP 1c | 3.74 | 184.8 | 299.3 | 2.4 | 43 | 463.6 | 99.8 | 1.39 |
| EP 1d | 4.7 | 221.8 | 322.5 | 3.5 | 29.9 | 464.1 | 92.7 | 1.29 |
| EP 1e | 27.5 | 152.8 | 350.5 | 10 | 24.8 | 458.3 | 39.2 | |

| Example No. | Temp. deg. C | Wt. % $C_2H_4$ | Wt. % $C_3H_6$ | $M_w$ GPC-dv | $M_n$ GPC-dv | $M_w/M_n$ | Mooney ML 1 + 4 at 125 C. | DSC Tc ° C. | DSC Cool Peak ° C. | DSC Tg ° C. | DSC Heat of Fusion (J/g) | DSC Melt Peak ° C. | DSC % Cryst (HF/292) *100 |
|---|---|---|---|---|---|---|---|---|---|---|---|---|---|
| Comp. EP 3a | 100 | 45.8 | 54.2 | 141,800 | 80,100 | 1.77 | 39.3 | −11.9 | −22.6 | −48.7 | 5.0 | −21.3 | 1.7 |
| EP 2a | 70 | 45.4 | 54.6 | 313,300 | 135,500 | 2.31 | 144.6 | — | — | −52.8 | 0.0 | — | 0.0 |
| EP 2b | 80 | 45.2 | 54.8 | 286,600 | 131,200 | 2.18 | 137.3 | — | — | −53.2 | 0.0 | — | 0.0 |
| EP 2c | 90 | 40.9 | 59.1 | 258,400 | 130,400 | 1.98 | 115.3 | — | — | −52.7 | 0.0 | — | 0.0 |
| EP 2d | 90 | 44.2 | 55.8 | 263,800 | 136,300 | 1.94 | 125.7 | — | — | −55.4 | 0.0 | — | 0.0 |
| EP 2e | 100 | 44.6 | 55.4 | 231,300 | 120,200 | 1.92 | 107.4 | — | — | −54.0 | 0.0 | 0.0 | 0.0 |
| EP 2f | 100 | 67.4 | 32.6 | 142,700 | 74,700 | 1.91 | | 51.28 14.24 | | −49.17 | 13.88 | 2.38 | 4.75 |
| Comp. EP 3b | 100 | 50.8 | 49.2 | 140,700 | 64,000 | 2.20 | 30.2 | −2.4 | −11.2 | −53.1 | 10.8 | −16.2 | 3.7 |
| Comp. EP 3c | 100 | 44.1 | 55.9 | 123,700 | 64,100 | 1.93 | 25.9 | −16.9 | −23.4 | −52.1 | 3.0 | −24.0 | 1.0 |
| Comp. EP 3d | 90 | 44.3 | 55.6 | 154,000 | 81,500 | 1.89 | 43.3 | −18.7 | −27.2 | −52.9 | 3.5 | −26.3 | 1.2 |
| Comp. EP 3e | 80 | 41.9 | 58.2 | 198,900 | 97,300 | 2.04 | 78.3 | — | — | −53.5 | 0.8 | −25.6 | 0.3 |
| Comp. EP 3f | 70 | 44.0 | 56.1 | 214,300 | 113,200 | 1.89 | 90.6 | — | — | −51.5 | 2.7 | −24.5 | 0.9 |
| Comp. EP 3g | 100 | 51.6 | 48.4 | 146,400 | 76,700 | 1.91 | 44.8 | −2.5 | −11.72 | −54.15 | 14.52 | −17.03 | 5.0 |
| EP 1a | 100 | 45.5 | 54.5 | 221,800 | 108,500 | 2.04 | 87.2 | 3.4 | −16.22 | −55.88 | 1.713 | −18.65 | 0.6 |
| EP 1b | 90 | 44.7 | 55.3 | 253,000 | 116,600 | 2.17 | 116.5 | 5.01 | −16.59 | −55.49 | 0.9782 | −19.07 | 0.3 |
| EP 1c | 80 | 43.5 | 56.5 | 297,000 | 151,500 | 1.96 | 137.3 | 12.16 | −19.49 | −56.49 | 0 | 0 | 0.0 |
| EP 1d | 70 | 45.2 | 54.8 | 333,400 | 178,600 | 1.87 | 137.6 | 10.28 | −16.36 | −56.41 | 0 | 0 | 0.0 |
| Ep 1e | 100 | 67.5 | 32.5 | 149,200 | 78,500 | 1.90 | | 83.56 55.37 8.19 | | −49.1 | 8.44 3.13 | 2.1 62.9 | 2.89 1.07 |

Polymerization of Ethylene/Propylene/Diene Interpolymer

An ethylenelpropyleneldiene interpolymer is prepared using the general polymerization procedure set forth above using the reactor conditions set forth below.

Al/Ti ratio: 10
Temp: 101.6° C.
C3 grams loaded: 207.3
H2 delta pressure: 150.6
Isopar™ mass, grams: 1455.9
Octene mass, gram: 0
Diene mass, grams: 17.6
C2 load, grams: 141.54
Total pressure (psi (MPa)): 460.4 (3.174)
$C_2$ partial pressure (psi (MPa)): 309.4 (2.133)
Ethylene rate max: 8.8
Ethylene consumed: 27.5
Length of run: 10
Ti umole: 5
Dry weight: 37
Efficiency: 0.15

The resultant polymer had 54.7 weight percent ethylene, 42.7 weight percent propylene, 2.6 weight percent ENB. GPC-dv results indicate that the polymer had an Mw of 147200, an Mn of 67500, an $M_w/M_n$ of 2.18. Differential scanning calorimetry indicated a Tc of 14.09° C., a DSC cooling peak at −22.80° C., a DSC heat of fusion of 2.685 J/g, a DSC melting peak at −30.58° C., and a percent crystallinity of 0.9 percent.

With respect to the ethylene/propylene and the ethylene/propylene/diene copolymer examples the examples show that semi-crystalline EP and EPDM interpolymers with ethylene content greater than 45 weight percent (EP 2f and EP 1e) display the DSC characteristics observed for other copolymers. Further, amorphous materials with less than 45 weight percent ethylene prepared with the catalysts of this invention have lower Tg and higher molecular weight than polymers prepared under the same conditions with (tetramethylcyclopentadienyl)dimethyl(t-butylamido) silanetitanium 1,3-pentadiene.

The following sets forth procedures for preparing additional catalysts useful in the preparation of the polymers of the invention, as well as details of polymerizations made employing such catalysts.

Example A

Preparation of (2,3-dimethylindenyl)dimethyl(cyclododecylamido)silanetitanium Dichloride Preparation of $Li_2$[(2,3-dimethylindenyl)(cyclododecylamido)dimethyl-silane] 0.75 $Et_2O$ (2,3-dimethylindenyl) (cyclododecamido) dimethylsilane (5.47 g, 0.0142 moles) was stirred in diethylether (25 mL) as n-BuLi (0.030 moles, 11.94 mL of 2.5 M solution in hexane) was added slowly. This mixture was then allowed to stir for 16 hours. After the reaction period the volatiles were removed and the residue washed with hexane and then collected as a solid via filtration which was used without further purification or analysis (5.47 g, 85.2 percent).

Preparation of (2,3-dimethylindenyl)dimethyl (cyclododecylamido)-silanetitanium Dichloride $Li_2$[(2,3-dimethylindenyl)(cyclododecylamido) dimethylsilane]. ¾ $Et_2O$ (5.47 g, 0.0121 moles) was slowly added as a solid to a slurry of $TiCl_3(THF)_3$ (4.48 g, 0.0121 moles) in THF (75 mL). This mixture was allowed to stir for 45 minutes. $PbCl_2$ (1.68 g, 0.00604 moles) was then added to the mixture which was then allowed to stir for an additional 45 minutes. After the reaction period the volatiles were removed and the residue extracted and filtered using toluene. The toluene was then removed and the residue slurried in hexane and then collected as a red-brown crystalline solid by filtration. A second crop was obtained by concentrating and cooling the filtrate followed by a second filtration. The crops were then combined and determined to be the desired product (0.457 g, 7.6 percent).

$^1$H NMR (300 MHz, $C_6D_6$): δ 8 0.52 (s, 3 H), 0.63 (s, 3 H), 1.15–1.91 (m, 23 H), 2.11 (s, 3 H), 2.23 (s, 3 H), 5.31 (m, 1 H), 6.83–7.12 (m, 2 H), 7.29 (d, 1 H), 7.63 (d, 3 H).

Example B

Preparation of (2,3-dimethylindenyl)dimethyl(cyclododecylamido)silanetitanium Dimethyl (2,3-dimethylindenyl)dimethyl(cyclododecylamido) silane $TiCl_2$ (0.200 g, 0.000400 moles) was stirred in diethylether (50 mL) as methylMgI (0.00084 moles, 0.28 mL 3.0 M solution in diethylether) was added dropwise. This mixture was then allowed to stir for 30 minutes. After the reaction period the volatiles were removed and the residue extracted and filtered using hexane. Removal of the volatiles followed by a repeat of the filtration again using hexane resulted in the isolation of the desired product as an orange crystalline solid after the removal of the hexane (0.134 g, 73.2 percent).

$^1$H NMR (300 MHz, $C_6D_6$): δ 0.11 (s, 3 H), 0.53 (s, 3 H), 0.61 (s, 3 H), 0.65 (s, 3 H), 1.10–1.90 (m, 23 H), 1.98 (s, 3 H), 2.26 (s, 3 H), 5.12–5.25 (m, 1 H), 6.91 (t, 1 H), 7.09 (t, 1 H), 7.45 (d, 1 H), 7.58 (d, 1 H).

Example C

Preparation of [(N-cyclohexylamido)(dimethyl)(2,3,4,6-tetramethylindenyl)-silane]titanium Dimethyl Preparation of dimethylsilyl(2,3,4,6-tetramethylindenyl)(cyclohexylamine)

Dimethylsilyl(2,3,4,6-tetramethylindenyl)Cl (9.95 g, 37.8 mmol) was stirred in hexane (200 mL) as $NET_3$ (4.1 g, 40.6 mmol) was added followed by cyclohexylamine (4.05 g, 40.8 mmol). This mixture was allowed to stir for 24 hours at 20° C. After the reaction period the mixture was filtered and the desired product isolated as a pale yellow oil following the removal of the volatiles (10.98 g, 89.3 percent yield).

Preparation of Dilitium (N-cyclohexylamido)(dimethyl)(2,3,4,6-tetramethylindenyl)silane In the drybox 4.0 g (12.6 mmol) of (N-cyclohexylamino)(dimethyl) (2,3,4,6-tetramethylindenyl) silane was dissolved in 300 ml of hexane. To this solution 12.6 ml (25.2 mmol) of nBuLi (2.00 M) was added dropwise at 20° C. Upon complete addition of the nBuLi the solution was stirred for 12 hours after which the solvent was removed under reduced pressure to give 4.12 g (96 percent yield) of a yellow-orange powder.

Preparation of [(N-cyclohexylamido)(dimethyl)(2,3,4,6-tetramethylindenyl)silane]Titanium Dichloride In the drybox 4.63 g (12.5 mmol) of $TiCl_3(THF)_3$ was dissolved in 75 ml of THF. To this solution 4.12 g (12.5 mmol) of dilithium (N-cyclohexylamido) (dimethyl)(2,3,4,6-tetramethylindenyl)silane was added as a solid while stirring at 20° C. The solution was then stirred for 45 minutes. After this time period 1.73 g of $PbCl_2$ (6.25 mmol) was added and the solution stirred for 45 minutes. The THF was then removed under reduced pressure. The residue was then extracted with toluene, the solution filtered, and the toluene removed under reduced pressure. The residue was then triturated with hexane and the solution volume reduced whereupon a red precipitate was formed and collected via filtration and washed with cold (0° C.) hexane. The solid product was dried under vacuum to yield 1.70 g (31 percent yield) of product.

Example D

Preparation of [(N-cyclohexylamido)(dimethyl)(2,3,4,6-tetramethylindenyl)silane]titanium Dimethyl In the drybox 0.300 g of [(N-t-cyclohexylamino)(dimethyl)(2,3,4,6-tetramethylindenyl) silane]titanium dichloride (0.675 mmol) was suspended in 50 ml of $ET_2O$ at 20° C. To this suspension 0.45 ml of MeMgI (3.0 M) was added dropwise while stirring over a 20 minute period. After the addition MeMgI was completed, the solution was stirred for 40 minutes. Then the $ET_2O$ was removed under reduced pressure and the residue extracted with hexane, the solution filtered, the filtrate evaporated to dryness under reduced pressure to give 0.27 g (100 percent yield) of product.

Example E

Preparation of [(N-cyclohexylamido)(dimethyl)(2,3-methylindenyl)silane]-titanium(II)(1,4-diphenyl-1,3-butadiene)

In a 100 ml flask 0.300 g of (N-cyclohexylamido)(dimethyl)(2,3-methylindenyl)silane]titanium dichloride (0.720 mmol, from Example 23) was stirred with 0.149 g of 1,4-diphenyl-1,3-butadiene (0.720 mmol) in 70 ml of hexane at 0° C. To this solution 0.577 ml of 2.5M nBuLi (in hexane) was added and the mixture refluxed for 2h. After cooling the solution to 20° C., the solution was filtered. The filter residue was then washed with hexane. The hexane was then removed from the filtrate under reduced pressure to give 0.109 g (27 percent yield) of product.

Polymerization Runs

A two-liter Parr reactor was charged with 740 g of mixed alkanes solvent (Isopar™-E) and 118 g of 1-octene comonomer. Hydrogen was added as a molecular weight control agent by differential pressure expansion from an 75 ml addition tank at 25 psi (2070 Kpa). The reactor was heated to the polymerization temperature of 140° C. and saturated with ethylene at 500 psig (3.4 Mpa). 2.0 mmol each of catalyst and cocatalyst at 0.005M solutions in toluene were premixed in the drybox. After the desired premix time, the solution was transferred to a catalyst addition tank and injected into the reactor. The polymerization conditions were maintained for 15 minutes with ethylene on demand. The resulting solution was removed from the reactor, and a hindered phenol anti-oxidant (Irganox™ 1010 from Ciba Geigy Corp.) was added to the resulting solution. Polymers formed were dried in a vacuum oven set at 120° C. for about 20 hours.

Example F

Preparation of [(N-isopropylamido)(dimethyl)(2,3,4,6-tetramethylindenyl)silane] Titanium Dimethyl Preparation of Dimethylsilyl(2,3,4,6-tetramethylindenyl)(isopropylamine)

Dimethylsilyl(2,3,4,6-tetramethylindenyl)Cl (22.29 grams, 84.17 mmol) was stirred in THF as i-$PrNH_2$ (28.68 mL, 336.7 mmol) was added. The mixture was stirred for 16 hours. The volatiles were removed under reduced pressure. The residue was extracted with hexane and filtered through a diatomaceous earth filter aid on a 10–15 mm glass frit. The hexane was removed under reduced pressure to afford the product as a yellow oil. Yield; 17.23 grams, 71 percent.

Preparation of [(N-isopropylamido)(dimethyl)(2,3,4,6-tetramethylindenyl)silane]titanium Dichloride In the drybox, 17.23 grams (59.93 mmol) of dimethylsilyl (2,3,4,6-tetramethylindenyl)(isopropylamine) was dissolved in 350 mL of hexane in a 500 mL round-bottom schienk flask. Two equivalents of n-BuLi (47.94 mL, 2.5 M in hexanes) were then added via syringe. The reaction was stirred for twelve hours. The solvent was removed under reduced pressure to afford a orange powder. The powder was dissolved in 250 mL of THF. TiCl$_3$(THF)$_3$ (22.2 grams, 59.93 mmol) was added as a solid. After 15 minutes, CH$_2$Cl$_2$ (2.48 mL, 29.97 mmol) was added. After two hours, the solvent was removed under reduced pressure. The residue was extracted with toluene and filtered through a diatomaceous earth filter aid on a 10–15 mm glass frit. The toluene was removed under reduced pressure. The residue was slurried in hexane and filtered over a 10–15 mm glass frit. The residue was dried under reduced pressure to afford a red powder. Yield; 12.3 grams, 51 percent.

Preparation of [(N-isopropylamido)(dimethyl)(2,3,4,6-tetramethylindenyl)silane]titanium Dimethyl In the drybox, [(N-isopropylamido)(dimethyl)(2,3,4,6-tetramethylindenyl)silane]titanium dichloride (6.92 grams, 17.12 mmol) was suspended in 150 mL of Et$_2$O in a 250 mL round bottom flask. Two equivalents of a 3.0 M THF solution of MeMgCl (11.41 mL, 34.23 mmol) were added. The mixture was stirred for one hour. The volatiles were removed under reduced pressure. The residue was extracted with hexane and filtered through a diatomaceous earth filter aid on a 10–15 mm glass frit. The hexane was removed under reduced pressure to afford a orange powder. Yield; 5.8 grams, 93 percent.

Example G

Preparation of [(N-isopropylamido)(dimethyl)(2,3,4, 6-tetramethylindenyl)silane]-titanium (1,4-diphenyl-1,3-butadiene)

In the drybox, 0.50 grams (1.24 mmol) of [(N-isopropylamido)(dimethyl)(2,3,4,6-tetramethylindenyl)silane] titanium dichloride was slurried in 60 mL of cyclohexane in a 100 mL round-bottom schlenk flask. 1,4-Diphenyl-1,3-butadiene (0.255 grams, 1.24 mmol) was added as a solid. Two equivalents of n-BuLi (0.989 mL, 2.5 M in hexanes) were then added via syringe. The flask was fitted with a condenser and heated to reflux for one hour. Upon cooling, the reaction was filtered through a diatomaceous earth filter aid (Celite ™) on a 10–15 mm glass frit. The salts and filter aid were washed with 50 mL of pentane. The solvent was removed under reduced pressure to afford a red/brown powder. Yield; 300 mg, 45 percent.

Polymerization experiments were performed using a 3.8 liter stirred reactor charged with 1440 g of Isopar E™ (mixed alkanes; available from Exxon Chemicals Inc.), 132 g of 1-octene, and 10 mmol of hydrogen. The reactor was heated to 130° C. and saturated with ethylene to 450 psig (4.5 Mpa). The catalyst was prepared in a drybox by springing together 5.0 mmol (1.0 mL, 0.005 M) of the metal complex, 15.0 mmol (1.0 mL, 0.015 M) of cocatalyst, trispentafluorophenylborane (TPFPB), and 50.0 mmol (1.0 mL, 0.05 M) of scavenger, modified methylaluminoxane (from Akzo-Nobel), with additional Isopar E™ to give a total volume of 17 mL. The catalyst solution was then transferred by syringe to a catalyst addition loop and injected into the reactor over approximately 4 minutes using a flow of high pressure solvent. The polymerization was allowed to proceed for 10 minutes while feeding ethylene on demand to maintain a pressure of 445 psig (4.5 Mpa). The polymer solution was then poured from the reactor into a nitrogen-purged glass kettle containing approximately 15 mL of isopropanol. A 20 mL aliquot of a stabilizer solution prepared by dissolving 6.66 g of Irgaphos™ 168 and 3.33 g of Irganox™ 1010 in 500 mL of toluene was added. The polymer solution was poured into a tray, air dried overnight, then thoroughly dried in a vacuum oven for two days.

Example H

Synthesis of: dichloro[N-(cyclohexyl)-1,1-dimethyl-[1,2,3,4,5-π)-1,5,6,7-tetrahydro-2-methyl-s-indacen-1-yl]silanaminto(2-)-N] titanium (also referred to as dimethylsilyl(2-methyl-s-indacenyl)(cyclohexyl-amido)TiCl$_2$

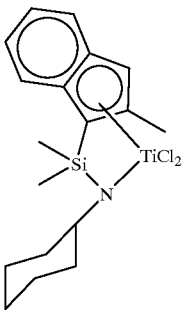

Preparation of chlorodimethyl(1,5,6,7-tetrahydro-2-methyl-s-indacen-1-yl)silane 1,5,6,7-tetrahydro-2-methyl-s-indacen-1-yl)lithium (1c)) (24.369 g, 0.13831 moles) in THF (100 mL) was added dropwise to a solution of Me$_2$SiCl$_2$ (89.252 g, 0.69155 moles) in THF (150 mL). This mixture was then allowed to stir at 20 to 25° C. for 5 hours. After the reaction period the volatiles were removed and the residue extracted and filtered using hexane. The removal of the hexane resulted in the isolation of the desired product as an off-white crystalline solid (31.1451 g, 85.7 percent).

Preparation of N-(cyclohexyl)-1,1-dimethyl-1-(1,5,6,7-tetrahydro-2-methyl-s-indacen-1-yl)silanamine Chlorodimethyl(1,5,6,7-tetrahydro-2-methyl-s-indacen-1-yl) silane (5.67 g, 0.0216 moles) was stirred in hexane (50 mL) as NEt$_3$ (2.18 g, 0.0216 moles) and cyclohexylamine (2.13 g, 0.0216 moles) were added. This mixture was allowed to stir 16 hours. After the reaction period the mixture was filtered and the volatiles removed resulting in the isolation of the desired product as a yellow oil (6.62 g, 94.3 percent).

Preparation of [N-(cyclohexyl)-1,1-dimethyl-[1,2,3,4,5-π)-1,5,6,7-tetrahydro-2-methyl-s-indacen-1-yl]silanaminto (2-)-N]dilithium N-(cyclohexyl)-1,1-dimethyl-1-(1,5,6,7-tetrahydro-2-methyl-s-indacen-1 -yl)silanamine (6.67 g, 0.02048 moles) was stirred in hexane (100 mL) as nBuLi (0.04302 moles, 21.51 mL of 2.0 M solution in cyclohexane) was added slowly. This mixture was then allowed to stir 16 hours. After the reaction period the desired product was isolated as a solid which was used without further purification or analysis (7.23 g, product still contained residual hexane).

Preparation of dichloro[N-(cyclohexyl)-1,1-dimethyl-[1,2,3,4,5-η)-1,5,6,7-tetrahydro-2-methyl-s-indacen-1-yl]silanaminto(2-)-N] titanium

[N-(cyclohexyl)-1,1-dimethyl-[1,2,3,4,5-π)-1,5,6,7-tetrahydro-2-methyl-s-indacen-1-yl]silanaminto(2-)-N] dilithium (7.23 g, 0.0214 moles) was slowly added as a solid to a slurry of $TiCl_3(THF)_3$ (7.93 g, 0.0214 moles) in THF (50 mL). This mixture was allowed to stir for 30 minutes. $PbCl_2$ (3.80 g, 0.0136 moles) was then added and the mixture allowed to stir for an additional hour. After the reaction period the volatiles were removed and the residue extracted and filtered using toluene. Removal of the toluene resulted in the isolation of a dark residue. This residue was then slurried in hexane and the desired product isolated via filtration as a solid (3.71 g, 39.2 percent).

Example H

Synthesis of dimethyl[N-(cyclohexyl)-1,1-dimethyl-[1,2,3,4,5-n)-1,5,6,7-tetrahydro-2-methyl-s-indacen-1-yl]silanaminto(2-)-N] titanium (also referred to as dimethylsilyl(2-methyl-s-indacenyl)(cyclohexyl-amido)TiMe$_2$ Dichloro[N-(cyclohexyl)-1,1-dimethyl-[1,2,3,4,5π)-1,5,6,7-tetrahydro-2-methyl-s-indacen-1-yl]silanaminto(2-)-N] titanium (0.400 g, 0.00904 moles) was stirred in diethylether (50 mL) as MeMgBr (0.0181 moles, 0.60 mL of 3.0 M solution in diethylether) was added slowly. This mixture was then stirred for 1 hour. After the reaction period the volatiles were removed and the residue extracted and filtered using hexane. Removal of the hexane resulted in the isolation of the desired product as a solid (0.309 g, 85.1 percent).

Example I

Synthesis of: dichloro[N-(cyclohexyl)-1,1-dimethyl-[1,2,3,4,5-π)-1,5,6,7-tetrahydro-2,3-dimethyl-s-indacen-1-yl]silanaminto(2-)-N]titanium (also referred to as dimethylsilyl(2,3-dimethyl-s-indacenyl)(cyclohexylamido)TiCl$_2$

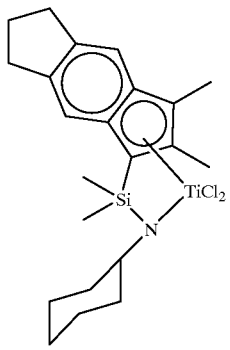

Preparation of N-(cyclohexyl)-1,1-dimethyl-1-(1,5,6,7-tetrahydro-2,3-dimethyl-s-indacen-1-yl) silanamine Chlorodimethyl(1,5,6,7-tetrahydro-2,3-dimethyl-s-indacen-1-yl)silane (5.00 g, 0.01806 moles) was stirred in hexane (80 mL) as $NEt_3$ (3.29 g, 0.03251 moles) and t-butylamine (1.81 g, 0.01824 moles) were added. This mixture was allowed to stir 16 hours. After the reaction period the mixture was filtered and the volatiles removed resulting in the isolation of the desired product as a yellow oil (5.55 g, 90.9 percent).

Preparation of [N-(cyclohexyl)-1,1-dimethyl-[1,2,3.4.5-π)-1,5,6,7-tetrahydro-2.3-dimethyl-s-indacen-1-yllsilanaminto (2-)-N]dilithium N-(cyclohexyl)-1,1-dimethyl-1-(1,5,6,7-tetrahydro-2,3-dimethyl-s-indacen-1-yl)silanamine (5.30 g, 0.01570 moles) was stirred in hexane (75 mL) as n-BuLi (0.03454 moles, 13.8 mL of 2.5 M solution in hexane) was added slowly. This mixture was then allowed to stir for 72 hours. After the reaction period the hexane was decanted away and the volatiles were removed resulting in the isolation of the desired product as an orange glassy solid which was used without further purification or analysis (5.56 g, 99.9 percent).

Preparation of dichloro[N-(cyclohexyl)-1,1-dimethyl-[1,2,3,4,5-π)-1,5,6,7-tetrahydro-2,3-dimethyl-s-indacen-1-yl]silanaminto(2-)-N]titanium

[N-(cyclohexyl)-1,1-dimethyl-[1,2,3,4,5-π)-1,5,6,7-tetrahydro-2,3-dimethyl-s-indacen1-yl]silanaminto(2-)-N] dilithium (0.500 g, 0.01428 moles) was slowly added as a solid to a slurry of $TiCl_3(THF)_3$ (0.529 g, 0.001428 moles) in THF 50 mL. This mixture was allowed to stir for 2 hours. $PbCl_2$ (0.317 g, 0.001142 moles) was then added and the mixture allowed to stir for an additional hour. After the reaction period the volatiles were removed and the residue extracted and filtered using toluene. Removal of the toluene resulted in the isolation of a dark residue. This residue was then slurried in hexane and cooled in a refrigerator for 72 hours. The desired product was then isolated via filtration as a solid (0.259 g, 43.8 percent).

Example J

Synthesis of: dimethyl[N-(cyclohexyl)-1,1-dimethyl-[1,2,3,4,5-π)-1,5,6,7-tetrahydro-2,3-dimethyl-s-indacen-1 -yl]silanaminto(2-)-N]titanium (also referred to as dimethylsilyl(2,3-dimethyl-s-indacenyl)(cyclohexylamido)TiMe$_2$ Dichloro[N-(cyclohexyl)-1,1-dimethyl-[1,2,3,4,5-.eta.)-1,5,6,7-tetrahydro-2,3-dimethyl-s-indacen-1-yl]silanaminto (2-)-N] titanium (0.300 g, 0.0006588 moles) was stirred in diethylether (50 mL) as MeMgBr (0.001447 moles, 0.48 mL of 3.0 M solution in diethylether) was added slowly. This mixture was then stirred for 1 hour. After the reaction period the volatiles were removed and the residue extracted and filtered using hexane. Removal of the hexane resulted in the isolation of the desired product as an orange solid (0.249 g, 91.2 percent).

Example K

Synthesis of: dichloro[N-(cyclohexyl)-1,1-dimethyl-[1,2,3,4,5-η)-1,5,6,7-tetrahydro-2-methyl-3-phenyl-s-indacen-1-yl]silanaminto(2-)-N]titanium (also referred to as dimethylsilyl(2-methyl-3-phenyl-s-indacenyl)(cyclohexylamido)TiCl$_2$

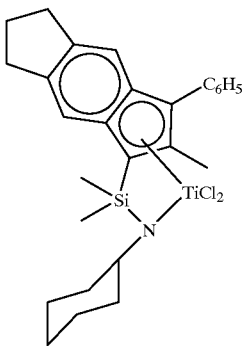

Preparation of N-(cyclohexyl)-1,1-dimethyl-1-(1,5,6,7-tetrahydro-2-methyl-3-phenyl-s-indacen-1-yl)silanamine Chlorodimethyl(1,5,6,7-tetrahydro-2-methyl-3-phenyl-s-indacen-1-yl) silane (9c)) (5.6340 g, 0.01633 moles) was stirred in hexane (100 mL) as NEt$_3$ (2.9673 g, 0.02932 moles) and cyclohexylamine (1.6373 g, 0.01651 moles) were added. This mixture was allowed to stir for 24 hours. After the reaction period the mixture was filtered and the volatiles removed resulting in the isolation of the desired product as a yellow oil (5.8969 g, 89.9 percent).

Preparation of [N-(cyclohexyl)-1,1-dimethyl-[1,2,3,4,5-η)-1,5,6,7-tetrahydro-2-methyl-3-phenyl-s-indacen-1-yl]silanaminto(2-)-N]dilithium N-(cyclohexyl)-1,1-dimethyl-1-(1,5,6,7-tetrahydro-2-methyl-3-phenyl-s-indacen-1-yl)silanamine (5.8969 g, 0.01468 moles) was stirred in hexane (100 mL) as nBuLi (0.032 moles, 16.00 mL of 2.0 M solution in cyclohexane) was added slowly. This mixture was then allowed to stir 16 hours during which time a sticky precipitate formed. The volatiles were then removed and the resulting pale yellow solid slurried in cold hexane. After the reaction period the solid was collected via suction filtration as a yellow powder which was used without further purification or analysis (5.3101 g, 87.5 percent).

Preparation of dichloro[N-(cyclohexyl)-1,1-dimethyl-[1,2,3,4,5-η)-1,5,6,7-tetrahydro-2-methyl-3-phenyl-s-indacen-1-yl]silanaminto(2-)-N]titanium

[N-(cyclohexyl)-1,1-dimethyl-[1,2,3,4,5-η)-1,5,6,7-tetrahydro-2-methyl-3-phenyl-s-indacen-1-yl]silanaminto(2-)-N]dilithium (5.3103 g, 0.01284 moles) in THF (50 mL) was added dropwise to a slurry of TiCl$_3$(THF)$_3$ (4.7570 g, 0.01284 moles) in THF 100 mL). This mixture was allowed to stir for 2 hours. PbCl$_2$ (1.8896 g, 0.006795 moles) was then added and the mixture allowed to stir for an additional hour. After the reaction period the volatiles were removed and the residue extracted and filtered using toluene. Removal of the toluene resulted in the isolation of a dark residue. This residue was then slurried in hexane and cooled to −10° C. The desired product was then isolated via filtration as a red crystalline solid (3.0765 g, 46.2 percent).

Example L

Synthesis of: dimethyl[N-(cyclohexyl)-1,1-dimethyl-[1,2,3,4,5-η)-1,5,6,7-tetrahydro-2-methyl-3-phenyl-s-indacen-1-yl]silanaminto(2-)-N]titanium (also referred to as dimethylsilyl(2-methyl-3-Phenyl-s-indacenyl)(cyclohexylamido)TiMe$_2$

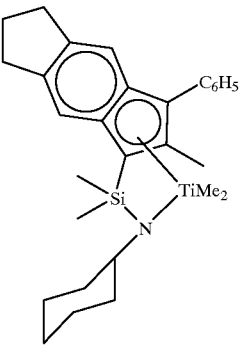

Dichloro[N-(cyclohexyl)-1,1-dimethyl-[1,2,3,4,5-η)-1,5,6,7-tetrahydro-2-methyl-3-phenyl-s-indacen-1-yl]silanaminto(2-)-N]titanium (0.7164 g, 0.001382 moles) was stirred in diethylether (50 mL) as MeMgBr (0.002760 moles, 0.92 mL of 3.0 M solution in diethylether) was added slowly. This mixture was then stirred for 1 hour. After the reaction period the volatiles were removed and the residue extracted and filtered using hexane. Removal of the hexane resulted in the isolation of the desired product as a sticky yellow-red residue (0.5102 g, 77.3 percent).

Example M

Synthesis of dichloro[N-(cyclohexyl)-1,1-dimethyl-[1,2,3,4,5-η)-1,5,6,7-tetrahydro-3-phenyl-s-indacen-1-yl]silanaminto(2-)-N]titanium (also referred to as dimethylsilyl(3-phenyl-s-indacen-1-yl)(cyclohexylamido)TiCl$_2$

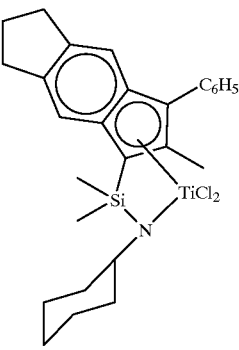

Preparation of N-(cyclohexyl)-1,1-dimethyl-1-(1,5,6,7-tetrahydro-3-Dhenyl-s-indacen-1-yl)silanamine Chlorodimethyl(1,5,6,7-tetrahydro-3-phenyl-s-indacen-1-yl) silane (3.8523 g, 0.01182 moles) was stirred in hexane (100 mL) as NEt$_3$ (1.5136 g, 0.01496 moles) and cyclohexylamine (1.2107 g, 0.01221 moles) were added. This mixture was allowed to stir for 24 hours. After the reaction period the mixture was filtered and the volatiles removed resulting in the isolation of the desired product as a yellow oil (4.3313 g, 94.5 percent).

Preparation of [N-(cyclohexyl)-1,1-dimethyl-[1,2,3,4,5-η)-1,5,6,7-tetrahydro-3-phenyl-s-indacen-1-yl]silanaminto(2-)-N]dilithium N-(cyclohexyl)-1,1-dimethyl-1-(1,5,6,7-tetrahydro-3-phenyl-s-indacen-1-yl)silanamine (4.3313 g, 0.01117 moles) was stirred in hexane (100 mL) as nBuLi (0.024 moles, 12.00 mL of 2.0 M solution in cyclohexane) was added slowly. This mixture was then allowed to stir 16 hours during which time a sticky precipitate formed. The volatiles were then removed and the resulting pale yellow solid slurried in cold hexane. After the reaction period the solid was collected via suction filtration as a red crystalline powder which was used without further purification or analysis (5.3101 g, 87.5 percent).

Preparation of dichloro[N-(cyclohexyl)-1,1-dimethyl-1-[(1 2,3,4,5-η)-1,5,6,7-tetrahydro-3-phenyl-s-indacen-1-yl] silanaminato(2-)-N]titanium

[N-(cyclohexyl)-1,1-dimethyl-[1,2,3,4,5-η)-1,5,6,7-tetrahydro-3-phenyl-s-indacen-1-yl]silanaminto(2-)-N] dilithium (4.2135 g, 0.01055 moles) in THF (50 mL) was added dropwise to a slurry of $TiCl_3(THF)_3$ (3.9085 g, 0.01055 moles) in THF (100 mL). This mixture was allowed to stir for 2 hours. $PbCl_2$ (1.5373 g, 0.005529 moles) was then added and the mixture allowed to stir for an additional hour. After the reaction period the volatiles were removed and the residue extracted and filtered using toluene. Removal of the toluene resulted in the isolation of a dark residue. This residue was then slurried in hexane and cooled to 0° C. The desired product was then isolated via filtration as a red-brown crystalline solid (2.7655 g, 52.0 percent).

Example N

Synthesis of dimethyl[N-(cyclohexyl)-1,1-dimethyl-[(1,2,3,4,5-η)-1,5,6,7-tetrahydro-3-phenyl-s-indacen-1-yl]silanaminto(2-)-N]titanium (also referred to as dimethylsilyl(3-phenyl-s-indacen-1-yl)(cyclohexylamido)TiMe$_2$ Dichloro[N-(cyclohexyl)-1,1-dimethyl-1-[(1,2,3,4,5-η)-1,5,6,7-tetrahydro-3-phenyl-s-indacen-1-yl]silanaminato (2-)-N]titanium (0.5581 g, 0.001106 moles) was stirred in diethylether (50 mL) as MeMgBr (0.0022 moles, 0.74 mL of 3.0 M solution in diethylether) was added slowly. This mixture was then stirred for 1 hour. After the reaction period the volatiles were removed and the residue extracted and filtered using hexane. Removal of the hexane resulted in the isolation of the desired product as a yellow-red residue (0.2118 g, 41.3 percent).

2-ethylene/1-octene copolymerization

A stirred 3.8 liter reactor was charged with 1440 g of Isopar-E™ mixed alkanes solvent (available from Exxon Chemicals Inc.) and 126 g of 1-octene comonomer. Hydrogen was added as a molecular weight control agent by differential pressure expansion from a 75 mL addition tank at 25 psid (2070 kPa). The reactor was heated to the polymerization temperature of 130° C. and saturated with ethylene at 450 psig (3.1 MPa). Approximately 2.0 μmol each of the Catalyst of Example H and trispentafluorophenylborane cocatalyst as 0.005 M solutions in toluene were premixed in a drybox, transferred to a catalyst addition tank and injected into the reactor over approximately a four minute period. The polymerization conditions were maintained for 10 minutes with ethylene on demand. The resulting solution was removed from the reactor, and a hindered phenol antioxidant (Irganox™ 1010 from Ciba Geigy Corporation) was added to the resulting solution. Polymers formed were dried in a vacuum oven set at 120° C. for about 20 hours. The catalyst efficiency was 700 kilograms polymer per gram Ti. The melt index ($I_2$) of the polymer was 0.43 g/10 min.

What is claimed is:

1. An olefin polymer having a density of less than 0.910 g/cm3, bimodal short chain branching distribution and a bimodal molecular weight produced by a polymerization process in which a catalyst and at least one α-olefin are supplied to a reaction zone maintained at a temperature between about 75 and about 170° C., the catalyst comprising a metal complex corresponding to formula:

wherein:

M is titanium, zirconium or hafnium in the +2, +3 or +4 formal oxidation state;

A' is a substituted indenyl group substituted in at least the 2 or 3 position with a group selected from the group consisting of hydrocarbyl, fluoro-substituted hydrocarbyl, hydrocarbyloxy-substituted hydrocarbyl, dialkylamino-substituted hydrocarbyl, silyl, germyl and mixtures thereof, said group containing up to 40 nonhydrogen atoms, and said A' further being covalently bonded to M by means of a divalent Z group;

Z is a divalent moiety bound to both A' and M via σ-bonds, said Z comprising boron, or a member of Group 14 of the Periodic Table of the Elements, and also comprising nitrogen or phosphorus, wherein an aliphatic or alicyclic hydrocarbyl group is covalently bonded to the nitrogen or phosphorus via a primary or secondary carbon;

X is an anionic or dianionic ligand group having up to 60 atoms exclusive of the class of ligands that are cyclic, delocalized, σ-bound ligand groups;

X' independently each occurrence is a neutral ligating compound, having up to 20 atoms;

p is 0, 1 or 2, and is two less than the formal oxidation state of M, with the proviso that when X is a dianionic ligand group, p is 1; and q is 0, 1 or 2.

2. The polymer of claim 1, wherein the metal complex corresponds to the formula:

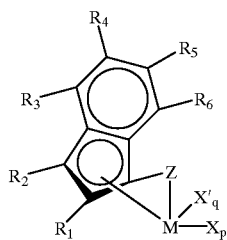

wherein:

$R_1$ and $R_2$, independently are groups selected from hydrogen, hydrocarbyl, perfluoro substituted hydrocarbyl, silyl, germyl and mixtures thereof, said group containing up to 20 nonhydrogen atoms, with the proviso that at least one of $R_1$ or $R_2$ is not hydrogen;

$R_3$, $R_4$, $R_6$, and $R_6$ independently are groups selected from hydrogen, hydrocarbyl, perfluoro substituted hydrocarbyl, silyi, germyl and mixtures thereof, said group containing up to 20 nonhydrogen atoms;

M is titanium, zirconium or hafnium;

Z is a divalent moiety comprising boron, or a member of Group 14 of the Periodic Table of the Elements, and also comprising nitrogen or phosphorus, said moiety having up to 60 non-hydrogen atoms, wherein an aliphatic or alicyclic hydrocarbyl group is covalently bonded to the nitrogen or phosphorus via a primary or secondary carbon;

p is 0, 1 or 2;

q is zero or one;

with the proviso that:
when p is 2, q is zero, M is in the +4 formal oxidation state, and X is an anionic ligand selected from the group consisting of halide, hydrocarbyl, hydrocarbyloxy, di(hydrocarbyl)amido, di(hydrocarbyl)phosphido, hydrocarbylsulfido, and silyl groups, as well as halo-, di(hydrocarbyl)amino-, hydrocarbyloxy- and di(hydrocarbyl)phosphino-substituted derivatives thereof, said X group having up to 20 nonhydrogen atoms, when p is 1, q is zero, M is in the +3 formal oxidation state, and X is a stabilizing anionic ligand group selected from the group consisting of allyl, 2-(N,N-dimethylaminomethyl)phenyl, and 2-(N,N-dimethyl)-aminobenzyl, or M is in the +4 formal oxidation state, and X is a divalent derivative of a conjugated diene, M and X together forming a metallocyclopentene group, and when p is 0, q is 1, M is in the +2 formal oxidation state, and X' is a neutral, conjugated or nonconjugated diene, optionally substituted with one or more hydrocarbyl groups, said X' having up to 40 carbon atoms and forming a η-complex with M.

3. The olefin polymer of claim 1, wherein the metal complex corresponds to the formula:

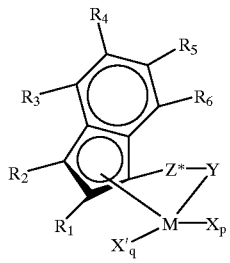

wherein:
R$_1$ and R$_2$ independently are hydrogen or C$_1$ alkyl, with the proviso that both R$_1$ and R$_2$ are not hydrogen;

R$_3$, R$_4$, R$_5$, and R$_6$ are independently hydrogen or C$_1$ alkyl;

M is titanium;

Y is —NR—, or —PR—;

Z* is SiR*$_2$, CR*$_2$, SiR*$_2$SiR*$_2$, CR*$_2$CR*$_2$, CR*=CR*, CR*$_2$SiR*$_2$, or GeR*$_2$;

R* each occurrence is independently hydrogen, or a member selected from hydrocarbyl, hydrocarbyloxy, silyl, halogenated alkyl, halogenated aryl, and combinations thereof, said R* having up to 20 non-hydrogen atoms, and optionally, two R* groups from Z (when R* is not hydrogen, or an R* group from Z and an R* group from Y form a ring system, and wherein, when Y is —NR* or —PR*—, the R* is covalently bonded to the N or P through a primary or secondary carbon;

R** is a aliphatic or alicyclic hydrocarbyl group covalently bonded to the nitrogen or phosphorus of Y via a primary or secondary carbon;

p is 0, 1 or 2;

q is zero or one;

with the proviso that:
when p is 2, q is zero, M is in the +4 formal oxidation state, and X is independently each occurrence methyl or benzyl, when p is 1, q is zero, M is in the +3 formal oxidation state, and X is 2-(N,N-dimethyl)aminobenzyl; or M is in the +4 formal oxidation state and X is 1,4-butadienyl, and when p is 0, q is 1, M is in the +2 formal oxidation state, and X' is 1,4-diphenyl-1,3-butadiene or 1,3-pentadiene.

4. An olefin polymer having a density of less than 0.910 g/cm$^3$, a bimodal short chain branching distribution and a bimodal molecular weight produced by a process in which a catalyst and one or more α-olefins are continuously supplied to a reaction zone maintained at a temperature between about 75 and about 170° C., the catalyst comprising a metal complex of formula (I):

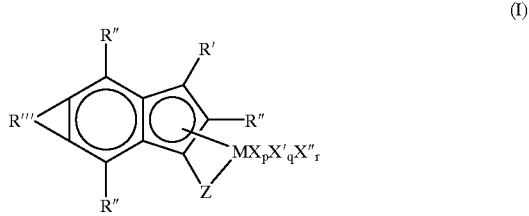

(I)

where M is titanium, zirconium or hafnium in the +2, +3 or +4 formal oxidation state;

R' and R" are independently each occurrence hydride, hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylene-phosphino-substituted hydrocarbyl, or hydrocarbylsulfido-substituted hydrocarbyl, said R' or R" group having up to 40 nonhydrogen atoms, and optionally two or more of the foregoing groups may together form a divalent derivative;

R''' is a divalent hydrocarbylene- or substituted hydrocarbylene group forming a fused system with the remainder of the metal complex, said R''' containing from 1 to 30 nonhydrogen atoms;

Z is a divalent moiety, or a moiety comprising one σ-bond and a neutral two electron pair able to form a coordinate-covalent bond to M, said Z comprising boron, or a member of Group 14 of the Periodic Table of the Elements, and also comprising nitrogen or phosphorus, wherein an aliphatic or alicyclic hydrocarbyl group is covalently bonded to the nitrogen or phosphorus via a primary or secondary carbon;

X is a monovalent anionic ligand group having up to 60 atoms exclusive of the class of ligands that are cyclic, delocalized, π-bound ligand groups;

X' independently each occurrence is a neutral ligating compound having up to 20 atoms;

X" is a divalent anionic ligand group having up to 60 atoms;

p is zero, 1,2, or 3;

q is zero, 1 or 2, and r is zero or 1; and 2) an activating cocatalyst the molar ratio of 1) to 2) being from 1:10,000 to 100:1, or the reaction product formed by converting 1) to an active catalyst by use of an activating technique.

5. The olefin polymer of claim 1, wherein the α-olefin is polymerized in the presence of the catalyst comprising the metal complex and an activating cocatalyst.

6. The olefin polymer of claim 5 wherein the activating cocatalyst comprises trispentafluorophenyl-borane or a cocatalyst corresponding to formula:

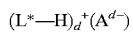

wherein:

L* is a neutral Lewis base;

(L*–H)+ is a Bronsted acid;

$A^{d-}$ is a noncoordinating, compatible anion having charge d–, and d is an integer from 1 to 3.

7. The olefin polymer of claim 6, wherein the anion $A^{d-}$ is selected from the group consisting of: a) sterically shielded diboron anions corresponding to formula:

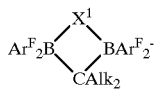

wherein:

Alk is alkyl, fluoroalkyl, aryl, or fluoroaryl and where two Alk groups are presents additionally hydrogen, $Ar^F$ is fluoroaryl, and $X^1$ is either hydrogen or halide, and b) anions corresponding to the formula:

wherein:

k is an integer from 1 to 3;

n' is an integer from 2 to 6;

n'–k=d;

M' is an element selected from Group 13 of the Periodic Table of the Elements; and Q independently each occurrence is selected from hydride, dialkylamido, halide, alkoxide, aryloxide, hydrocarbyl, and halosubstituted-hydrocarbyl radicals, said Q having up to 20 carbons with the proviso that in not more than one occurrence is Q halide.

8. The olefin polymer of claim 6 wherein the activating cocatalyst comprises a borane or borate selected from the group consisting of trispentafluorophenylborane, di(octadecyl)methylammonium tetrakis(pentafluorophenyl) borate, and di(octadecyl)(n-butyl)ammonium tetrakis (pentafluorophenyl)borate.

9. The olefin polymer of claim 6, wherein the activating cocatalyst further comprises a an aluminum compound selected from the group consisting of tri(hydrocarbyl) aluminum compounds having from 1 to 10 carbons in each hydrocarbyl group, oligomeric or polymeric alumoxane compounds, di(hydrocarbyl)(hydrocarbyloxy)aluminum compounds having from 1 to 20 carbons in each hydrocarbyl or hydrocarbyloxy group, or a mixture of the foregoing compounds.

10. The olefin polymer of claim 9, wherein the aluminum compound corresponds to the formula $T^1{}_2AlOT^2$, wherein $T^1$ is $C_{3-6}$ secondary or tertiary alkyl and $T^2$ is a $C_{12-30}$ alkaryl radical or aralkyl radical.

11. The olefin polymer of claim 10, wherein $T^2$ of the aluminum compound is 2,6-di(t-butyl)-4-methylphenyl, 2,6-di(t-butyl)4-methylphenyl, 2,6-di(i-butyl)4-methylphenyl, or 4-(3',5'-ditertiarybutyltolyl)-2,6-ditertiarybutylphenyl.

12. An olefin interpolymer having a density of less than 0.910 g/cm³, a bimodal short chain branching distribution and a bimodal molecular weight, the olefin interpolymer further characterized as satisfying at least four of the following criteria:

a) an $I_2 \leq 100$ g/10 min, b) an $M_w/M_n$ of from 1.5 to 3.0, c) at least 0.03 vinyls/ 1000 carbons, as determined by FTIR, and d) a deconvoluted DSC melting curve which shows two distinct first and second DSC melting points, and e) an ATREF curve which satisfies the following inequality:

ATREF Shape Factor≦0.90–0.00626 (Average Elution Temperature).

13. The olefin polymer of claim 12, wherein the ATREF curve satisfies the following inequality:

ATREF Shape Factor≦0.75–0.00626 (Average Elution Temperature).

14. An olefin interpolymer having a density of less than 0.910 g/cm³, a bimodal short chain branching distribution and a bimodal molecular weight, the olefin interpolymer further characterized as satisfying at least four of the following criteria:

a) an $I_2 \leq 100$ g/10 min, b) an $M_w/M_n$ of from 1.5 to 3.0, c) at least 0.03 vinyls/1000 carbons, as determined by FTIR, d) a deconvoluted DSC melting curve which shows two distinct first and second DSC melting points, and e) a deconvoluted gel permeation chromatogram which shows two distinct first and second component fractions, wherein the first component fraction has a first density, a first $I_2$, and is provided in a first weight percent, and wherein the second component fraction has a second density, a second $I_2$, and is provided in a second weight percent.

15. The olefin interpolymer of claim 12, which is further characterized as being an interpolymer of ethylene and at least one $C_3$–$C_{20}$ α-olefin.

16. The olefin interpolymer of claim 12, which is further characterized as having an $I_{10}/_2$ of at least 10.

17. The olefin interpolymer of any of claim 12, which is further characterized as having from 0.01 to 3 long chain branches/1000 carbons.

18. The olefin interpolymer of any of claim 12, which is further characterized as exhibiting a critical shear rate at the onset of surface melt fracture which is at least 50 percent greater than the critical shear rate at the onset of surface melt fracture for a linear interpolymer, wherein the olefin interpolymer and the linear interpolymer comprise the same comonomer or comonomers, the linear interpolymer has an $I_2$, and density within ten percent of that of the olefin interpolymer, and wherein the respective critical shear rates of the olefin interpolymer and the linear interpolymer are measured at the same melt temperature using a gas extrusion rheometer.

19. The olefin interpolymer of any of claim 12 which is further characterized as having a density of no more than 0.840 g/cm³.

20. The olefin interpolymer of claim 14, which is further characterized as being an interpolymer of ethylene and at least one $C_3$–$C_{20}$ α-olefin.

21. The olefin interpolymer of claim 14, which is further characterized as having an $I_{10}/I_2$ of at least 10.

22. The olefin interpolymer of any of claim 14, which is further characterized as having from 0.01 to 3 long chain branches/1000 carbons.

23. The olefin interpolymer of any of claim 14, which is further characterized as exhibiting a critical shear rate at the onset of surface melt fracture which is at least 50 percent greater than the critical shear rate at the onset of surface melt fracture for a linear interpolymer, wherein the olefin interpolymer and the linear interpolymer comprise the same comonomer or comonomers, the linear interpolymer has an $I_2$, and density within ten percent of that of the olefin interpolymer, and wherein the respective critical shear rates of the olefin interpolymer and the linear interpolymer are measured at the same melt temperature using a gas extrusion rheometer.

24. The olefin interpolymer of any of claim 14 which is further characterized as having a density of no more than 0.840 g/cm³.

25. The olefin polymer of claim 3, wherein the metal complex is (cyclohexylamido)dimethyl(η5-2,3,4,6-tetramethylindenyl)silanetitanium (IV) dimethyl or (isopropylamido)dimethyl(η5-2,3,4,6-tetramethylindenyl)silanetitanium (IV) dimethyl.

26. The olefin polymer of any of claim 12, wherein the olefin polymer is an interpolymer of ethylene, a $C_3$–$C_{20}$ α-olefin, and an optional diene.

27. The olefin polymer of any of claim 14, wherein the olefin polymer is an interpolymer of ethylene, a $C_3$–$C_{20}$ α-olefin, and an optional diene.

28. The olefin polymer of claim 22, wherein the olefin polymer is an interpolymer of ethylene, propylene and a diene.

29. The olefin polymer of claim 12, which satisfies each of the criteria (a)–(e).

30. The olefin polymer of claim 14, which satisfies each of the criteria (a)–(e).

31. An olefin polymer produced by polymerizing at least one α-olefin in the presence of a catalyst further comprising a metal complex corresponding to the formula:

wherein:

M is titanium, zirconium or hafnium in the +2, +3 or +4 formal oxidation state;

A' is a substituted indenyl group substituted in at least the 2 or 3 position with a group selected from hydrocarbyl, fluoro-substituted hydrocarbyl, hydrocarbyloxy-substituted hydrocarbyl, dialkylamino- substituted hydrocarbyl, silyl, germyl and mixtures thereof, said group containing up to 40 nonhydrogen atoms, and said A' further being covalently bonded to M by means of a divalent Z group;

Z is a divalent moiety bound to both A' and M via σ-bonds, said Z comprising boron, or a member of Group 14 of the Periodic Table of the Elements, and also comprising nitrogen or phosphorus, wherein an aliphatic or alicyclic hydrocarbyl group is covalently bonded -to the nitrogen or phosphorus via a primary or secondary carbon;

X is an anionic or dianionic ligand group having up to 60 atoms exclusive of the class of ligands that are cyclic, delocalized, η-bound ligand groups;

X' independently each occurrence is a neutral ligating compound, having up to 20 atoms;

p is 0, 1 or 2, and is two less than the formal oxidation state of M, with the proviso that when X is a dianionic ligand group, p is 1; q is 0, 1 or 2; and wherein the olefin polymer is characterized as having 0.01 to 3 long chain branches per 1000 carbons.

32. The polymer of claim 1 produced by a continuous solution polymerization process in which the catalyst, a solvent and the at least one α-olefin are continuously supplied to the reaction zone and the olefin polymer is continuously removed from the reaction zone.

33. The polymer of claim 4 produced by a continuous solution polymerization process in which the catalyst, a solvent and the at least one α-olefin are continuously supplied to the reaction zone and the olefin polymer is continuously removed from the reaction zone.

* * * * *

UNITED STATES PATENT AND TRADEMARK OFFICE
CERTIFICATE OF CORRECTION

PATENT NO. : 6,420,507 B1
DATED : July 16, 2002
INVENTOR(S) : Lawrence T. Kale et al.

It is certified that error appears in the above-identified patent and that said Letters Patent is hereby corrected as shown below:

Column 78,
Line 3, replace "g/cm3" with -- $g/cm^3$ --.
Line 65, replace "silyi" with -- silyl --.

Column 79,
Line 31, replace "η-complex" with -- π-complex --.
Lines 47 and 49, replace "$C_1$" with -- $C_{1-16}$ --.

Column 81,
Line 38, replace "presents" with -- present --.

Column 82,
Line 58, replace "$I_{10/2}$" with -- $I_{10}/I_2$ --.

Column 83,
Lines 9 and 32, replace "0.840 $g/cm^3$" with -- 0.890 $g/cm^3$ --.

Signed and Sealed this

Sixteenth Day of March, 2004

JON W. DUDAS
*Acting Director of the United States Patent and Trademark Office*